(12) United States Patent
Hurley

(10) Patent No.: US 12,185,796 B2
(45) Date of Patent: Jan. 7, 2025

(54) TOOL OPERATED ADJUSTMENT DEVICES, FIT SYSTEMS, AND LINE TENSIONING SYSTEMS

(71) Applicant: Garrett Ray Hurley, San Francisco, CA (US)

(72) Inventor: Garrett Ray Hurley, San Francisco, CA (US)

( * ) Notice: Subject to any disclaimer, the term of this patent is extended or adjusted under 35 U.S.C. 154(b) by 336 days.

(21) Appl. No.: 17/615,781

(22) PCT Filed: Jun. 4, 2020

(86) PCT No.: PCT/US2020/036128
§ 371 (c)(1),
(2) Date: Dec. 1, 2021

(87) PCT Pub. No.: WO2020/247636
PCT Pub. Date: Dec. 10, 2020

(65) Prior Publication Data
US 2022/0234862 A1    Jul. 28, 2022

Related U.S. Application Data

(60) Provisional application No. 62/937,808, filed on Nov. 20, 2019, provisional application No. 62/857,320, filed on Jun. 5, 2019.

(51) Int. Cl.
*A44B 11/12* (2006.01)
*A41F 9/02* (2006.01)
(Continued)

(52) U.S. Cl.
CPC ............. *A44B 11/125* (2013.01); *A41F 9/02* (2013.01); *A43C 11/165* (2013.01); *A44B 11/02* (2013.01);
(Continued)

(58) Field of Classification Search
CPC ..... A44B 11/02; A44B 11/165; A44B 11/125; B65H 75/406; B65H 75/4471;
(Continued)

(56) References Cited

U.S. PATENT DOCUMENTS 843,979 A    2/1907  Wantz
956,328 A    4/1910  Forshee
(Continued)

FOREIGN PATENT DOCUMENTS

WO    2018145802    8/2018

OTHER PUBLICATIONS

PCT Search Report and Written Opinion dated Aug. 18, 2020 of Application No. PCT/US 2020/036128.
(Continued)

*Primary Examiner* — Robert Sandy
(74) *Attorney, Agent, or Firm* — Gordon & Jacobson, P.C.

(57) ABSTRACT

A tool-operated adjustment device includes a housing supporting a rotatable spool that is operably coupled to a tension line. The spool is configured to rotate about a first axis in a first direction to wind the tension line, and to rotate in a second direction opposite the first direction to unwind the tension line. The device includes a socket pivotally coupled to the housing and configured to rotate about a second axis. The socket is selectively coupled to the spool to drive rotation of the spool in the first direction. The socket is configured to removably connect and disconnect to a tool configured to rotate the socket about the second axis. The device includes a release mechanism that is configured to selectively release the spool such that the spool is free to rotate in either the first or second direction in response to manual forces applied to the release mechanism.

22 Claims, 30 Drawing Sheets

(51) Int. Cl.
  *A43C 11/16* (2006.01)
  *A44B 11/02* (2006.01)
  *B65H 75/40* (2006.01)
  *B65H 75/44* (2006.01)

(52) U.S. Cl.
  CPC ....... *B65H 75/406* (2013.01); *B65H 75/4431* (2013.01); *B65H 75/4471* (2013.01); *B65H 75/4492* (2013.01); *B65H 2403/47* (2013.01); *B65H 2515/31* (2013.01)

(58) Field of Classification Search
  CPC ............ B65H 75/4431; B65H 75/4492; B65H 2403/47; Y10T 24/2187; B25B 25/00
  See application file for complete search history.

(56) References Cited

U.S. PATENT DOCUMENTS

| | | | |
|---|---|---|---|
| 1,107,934 A | 8/1914 | Hagan | |
| 2,191,228 A | 2/1940 | Dowd | |
| 2,604,098 A | 7/1952 | Kranc | |
| 2,699,918 A | 1/1955 | Bush | |
| 2,754,825 A | 7/1956 | Richmond | |
| 2,889,136 A | 6/1959 | Prete, Jr. | |
| 2,969,221 A | 1/1961 | Harmes | |
| 3,175,806 A | 3/1965 | Prete, Jr. | |
| 3,180,623 A | 4/1965 | Huber | |
| 3,279,760 A | 10/1966 | Bathum, Jr. | |
| 3,315,913 A | 4/1967 | Grieten | |
| 3,667,698 A | 6/1972 | Fisher | |
| 3,749,366 A | 7/1973 | Brucker | |
| 3,825,979 A | 7/1974 | Jakob | |
| 4,044,400 A | 8/1977 | Lewicki | |
| 4,154,427 A | 5/1979 | Hofmann | |
| 4,155,537 A | 5/1979 | Bronson | |
| 4,199,182 A | 4/1980 | Sunesson | |
| 4,278,002 A | 7/1981 | Siminoff | |
| 4,345,726 A | 8/1982 | Noda | |
| 4,414,713 A | 11/1983 | Prete, Jr. | |
| 4,436,254 A | 3/1984 | Normann | |
| 4,507,829 A | 4/1985 | Looker | |
| 4,542,883 A | 9/1985 | Rutzki | |
| 4,612,686 A | 9/1986 | Bowers | |
| 4,613,273 A * | 9/1986 | Wagner | B62D 43/045 |
| | | | 254/362 |
| 4,703,917 A | 11/1987 | Tomlinson | |
| 4,738,410 A | 4/1988 | Yamaguchi | |
| 4,823,443 A | 4/1989 | Waters | |
| 5,203,541 A | 4/1993 | Nix | |
| 5,271,606 A | 12/1993 | Kämper | |
| 5,295,664 A | 3/1994 | Kämper | |
| 5,325,613 A | 7/1994 | Sussmann | |
| 5,426,827 A | 6/1995 | Tracy | |
| 5,495,683 A | 3/1996 | Miotto | |
| 5,542,798 A | 8/1996 | Rawdon | |
| 5,606,779 A | 3/1997 | Lu | |
| 5,720,084 A | 2/1998 | Chen | |
| 5,800,105 A | 9/1998 | Stump | |
| 5,904,341 A | 5/1999 | Norrby | |
| 5,909,850 A | 6/1999 | Cavasin | |
| 6,003,578 A | 12/1999 | Chang | |
| 6,007,053 A | 12/1999 | Huang | |
| 6,095,450 A | 8/2000 | Jang | |
| 6,547,218 B2 | 4/2003 | Landy | |
| 6,654,987 B1 | 12/2003 | Wu | |
| 6,772,485 B2 | 8/2004 | Alpert | |
| 6,824,121 B2 * | 11/2004 | Boice | B60P 3/075 |
| | | | 24/69 ST |
| 6,880,810 B1 | 4/2005 | Hu | |
| 7,207,089 B2 | 4/2007 | Hanson | |
| 7,503,546 B1 | 3/2009 | Seager | |
| 7,503,736 B1 | 3/2009 | Chen | |
| 7,510,168 B1 | 3/2009 | Lin | |
| 7,644,906 B2 | 1/2010 | Rodrigue | |
| 7,877,845 B2 | 2/2011 | Signori | |
| 8,099,836 B2 | 1/2012 | Breeden | |
| 8,109,015 B2 | 2/2012 | Signori | |
| 8,277,401 B2 | 10/2012 | Hammerslag | |
| 8,308,410 B2 * | 11/2012 | Foryan | B60P 7/083 |
| | | | 410/103 |
| 8,434,200 B2 | 5/2013 | Chen | |
| 8,434,979 B1 | 5/2013 | Genge | |
| 8,516,662 B2 | 8/2013 | Goodman | |
| 8,680,997 B2 * | 3/2014 | Gallagher | H01H 3/02 |
| | | | 200/61.93 |
| 8,794,378 B2 | 8/2014 | Wolner | |
| 8,904,672 B1 | 12/2014 | Johnson | |
| 8,919,293 B2 | 12/2014 | Cromwell | |
| 8,967,332 B2 | 3/2015 | Wolner | |
| 9,138,030 B2 | 9/2015 | Soderberg | |
| 9,179,729 B2 | 11/2015 | Cotterman | |
| 9,185,942 B2 | 11/2015 | Rowland | |
| 9,277,776 B2 | 3/2016 | Laatz | |
| 9,285,776 B1 | 3/2016 | Custer | |
| 9,296,534 B2 | 3/2016 | Gerhardt | |
| 9,351,539 B2 | 5/2016 | Briggs | |
| 9,572,405 B2 | 2/2017 | Saris | |
| 9,597,786 B2 | 3/2017 | Romo | |
| 9,635,906 B2 | 5/2017 | Midorikawa | |
| 9,656,591 B1 | 5/2017 | Dumenigo | |
| 9,657,485 B2 | 5/2017 | Meyers | |
| 9,706,814 B2 | 7/2017 | Converse | |
| 9,725,029 B2 | 8/2017 | Chou | |
| 9,770,069 B2 | 9/2017 | Munns | |
| 9,770,070 B2 | 9/2017 | Cotterman | |
| 9,788,613 B2 | 10/2017 | Steffenhagen | |
| 9,855,055 B2 | 1/2018 | Kosiorek | |
| 9,867,430 B2 | 1/2018 | Hammerslag | |
| 9,918,865 B2 | 3/2018 | Nickel | |
| 9,956,094 B2 | 5/2018 | Mahon | |
| 9,968,473 B2 | 5/2018 | Mason | |
| 9,993,048 B2 | 6/2018 | Casebolt | |
| 10,016,203 B2 | 7/2018 | Esposito | |
| 10,070,695 B2 | 9/2018 | Burns | |
| 10,076,160 B2 | 9/2018 | Burns | |
| 10,077,570 B2 | 9/2018 | Underwood | |
| 10,085,502 B1 | 10/2018 | Trepanier | |
| 10,088,016 B2 | 10/2018 | Bujold | |
| 10,160,419 B2 | 12/2018 | Wedeking | |
| 10,227,030 B2 | 3/2019 | Kingery | |
| 10,251,451 B2 | 4/2019 | Converse | |
| 10,264,852 B2 | 4/2019 | Kim | |
| 10,266,364 B2 | 4/2019 | Hitsman | |
| 10,308,163 B2 | 6/2019 | Helline | |
| 10,363,046 B2 | 7/2019 | Hopman | |
| 10,413,019 B2 | 9/2019 | Soderberg | |
| 10,414,323 B2 | 9/2019 | Willodson | |
| 10,492,568 B2 | 12/2019 | Burns | |
| 10,543,630 B2 | 1/2020 | Hipwood | |
| 10,558,052 B2 | 2/2020 | Chang | |
| 10,575,591 B2 | 3/2020 | Schum | |
| 10,575,592 B1 | 3/2020 | Jones | |
| 10,576,015 B2 | 3/2020 | Wang | |
| 10,772,389 B2 | 9/2020 | Rossi | |
| 11,470,921 B2 | 10/2022 | Hurley | |
| 11,751,641 B2 | 9/2023 | Hurley | |
| 2003/0097736 A1 | 5/2003 | Blankenship | |
| 2003/0145434 A1 | 8/2003 | Lin | |
| 2004/0155230 A1 | 8/2004 | Fortin | |
| 2005/0087115 A1 | 4/2005 | Martin | |
| 2005/0177984 A1 | 8/2005 | Huang | |
| 2005/0267518 A1 | 12/2005 | Wright | |
| 2006/0156517 A1 | 7/2006 | Hammerslag | |
| 2007/0101615 A1 | 5/2007 | Munns | |
| 2008/0104811 A1 | 5/2008 | Burrows | |
| 2008/0184451 A1 | 8/2008 | Lemke | |
| 2008/0216213 A1 | 9/2008 | Lin | |
| 2008/0216291 A1 | 9/2008 | Lin | |
| 2008/0232922 A1 | 9/2008 | Chang | |
| 2009/0271976 A1 | 11/2009 | Huang | |
| 2009/0283729 A1 | 11/2009 | Carlson | |
| 2009/0300889 A1 | 12/2009 | Shiu | |
| 2010/0071174 A1 | 3/2010 | Adcock | |

(56) References Cited

U.S. PATENT DOCUMENTS

| | | |
|---|---|---|
| 2010/0137900 A1 | 6/2010 | Chao |
| 2010/0244543 A1 | 9/2010 | Fine |
| 2010/0293765 A1 | 11/2010 | Huang |
| 2012/0138883 A1 | 6/2012 | Gallagher |
| 2012/0205601 A1 | 8/2012 | Joubert |
| 2012/0227223 A1 | 9/2012 | Knox |
| 2013/0025100 A1 | 1/2013 | Ha |
| 2013/0092780 A1 | 4/2013 | Soderberg |
| 2013/0161365 A1 | 6/2013 | Shih |
| 2013/0269628 A1 | 10/2013 | Holt, Jr. |
| 2013/0318827 A1 | 12/2013 | Ringholz |
| 2013/0326847 A1 | 12/2013 | Zheng |
| 2013/0340292 A1 | 12/2013 | Cook |
| 2014/0061556 A1 | 3/2014 | Knox |
| 2014/0221889 A1 | 8/2014 | Burns |
| 2014/0338161 A1 | 11/2014 | Armour |
| 2015/0038889 A1 | 2/2015 | Mason |
| 2015/0040359 A1 | 2/2015 | Brown |
| 2015/0051638 A1 | 2/2015 | Dickinson |
| 2015/0053806 A1 | 2/2015 | Geisel |
| 2015/0121669 A1 | 5/2015 | Jungkind |
| 2015/0158615 A1 | 6/2015 | Downs |
| 2015/0191326 A1 | 7/2015 | Hall |
| 2015/0230560 A1 | 8/2015 | Chen |
| 2015/0257767 A1 | 9/2015 | Henderson |
| 2015/0289609 A1 | 10/2015 | Gittens |
| 2015/0359542 A1 | 12/2015 | Steinbaugh |
| 2016/0199206 A1 | 7/2016 | Lim |
| 2016/0206937 A1 | 7/2016 | Hanson |
| 2016/0207440 A1 | 7/2016 | Kingery |
| 2017/0100131 A1 | 4/2017 | Olbu |
| 2017/0295888 A1 | 10/2017 | Chen |
| 2017/0355298 A1 | 12/2017 | Cahall |
| 2018/0154862 A1 | 6/2018 | Wedeking |
| 2018/0334075 A1 | 11/2018 | Frank |
| 2019/0150569 A1 | 5/2019 | Chen |
| 2019/0216176 A1 | 7/2019 | Converse |

OTHER PUBLICATIONS

PCT Search Report and Written Opinion dated Aug. 18, 2020 of Application No. PCT/US 2020/036140.
PCT Search Report and Written Opinion dated Sep. 9, 2020 of Application No. PCT/US 20/36324.
U.S. Appl. No. 62/857,320, filed Jun. 5, 2019.
U.S. Appl. No. 62/937,808, filed Nov. 20, 2019.
U.S. Pat. No. 0,048,121; Issued June 6, 1865; Warner.

* cited by examiner

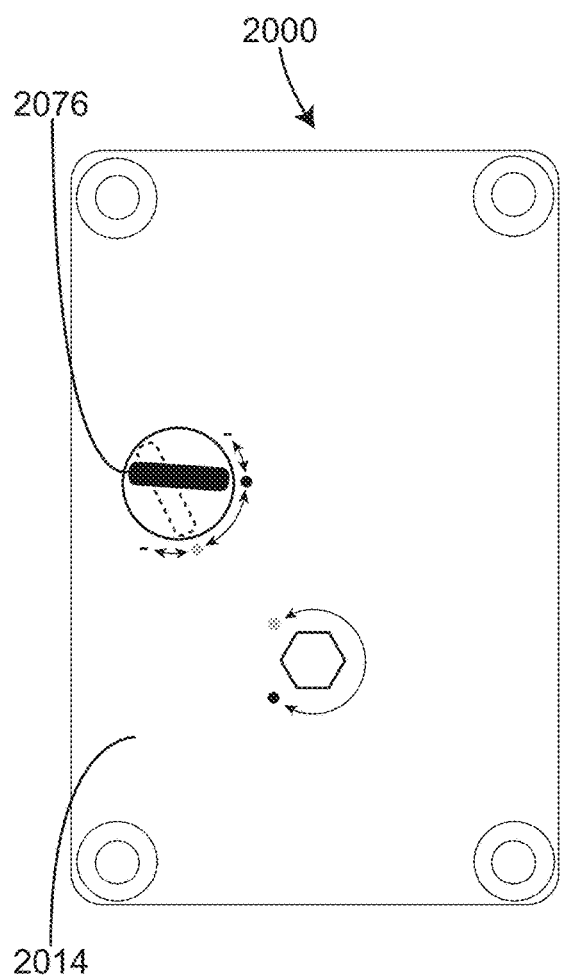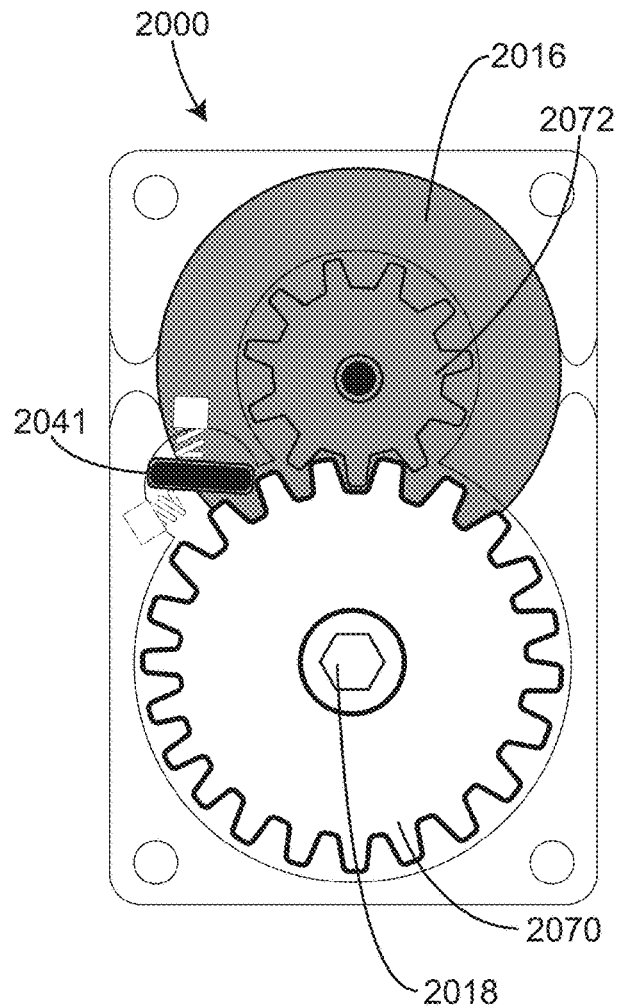
Fig. 23A      Fig. 23B
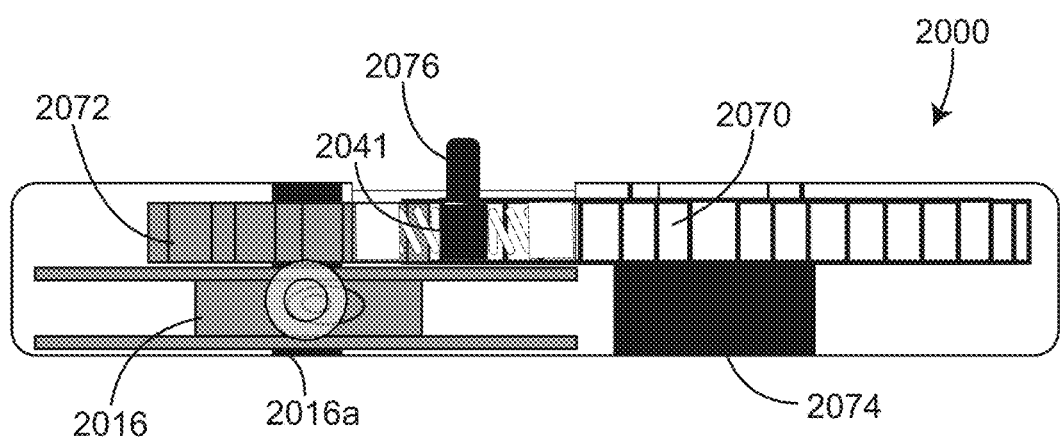
Fig. 23C

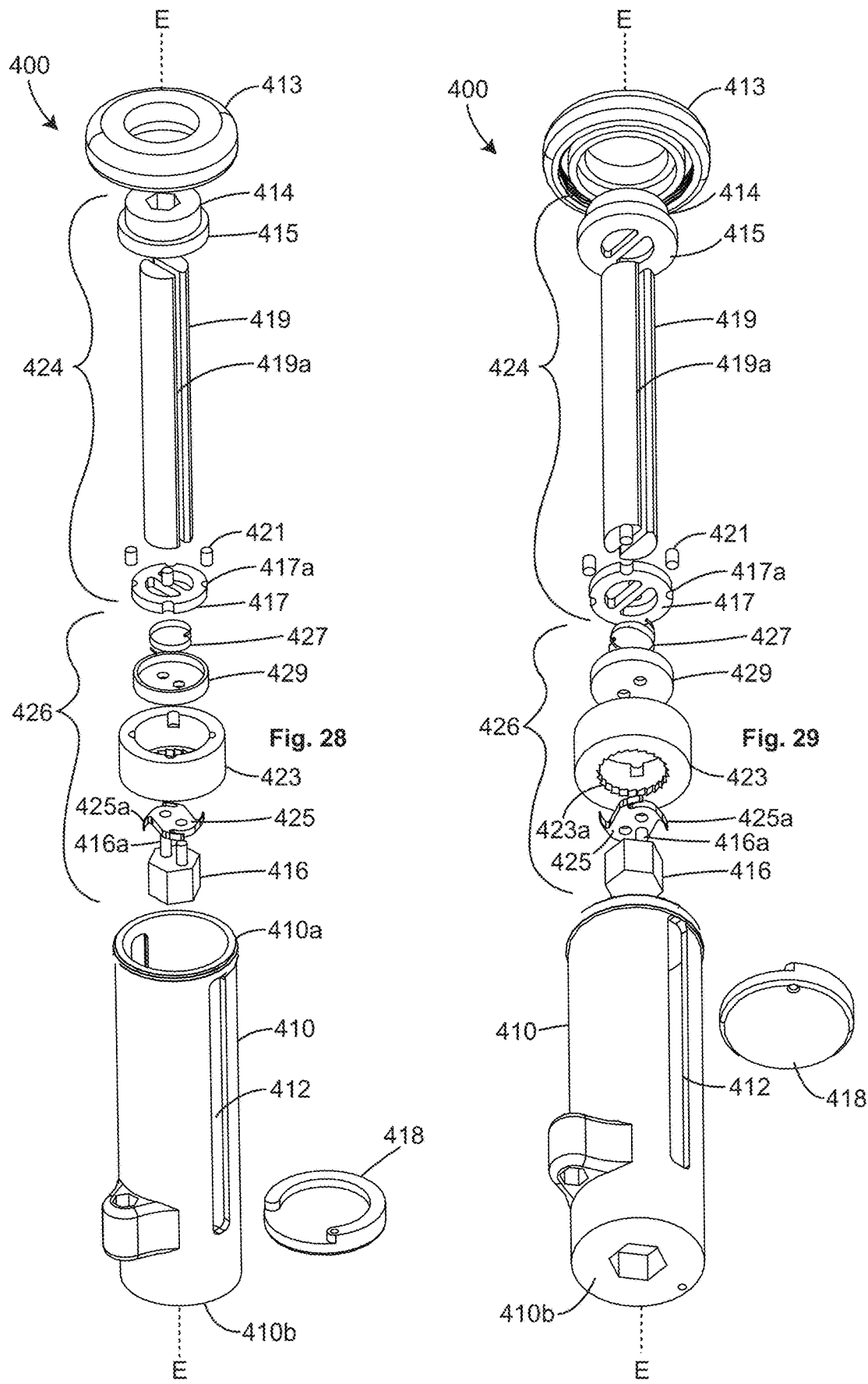

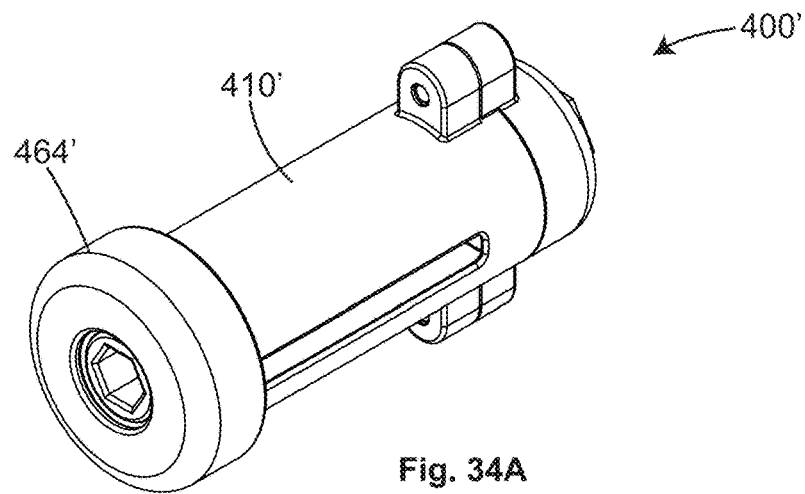
Fig. 34A
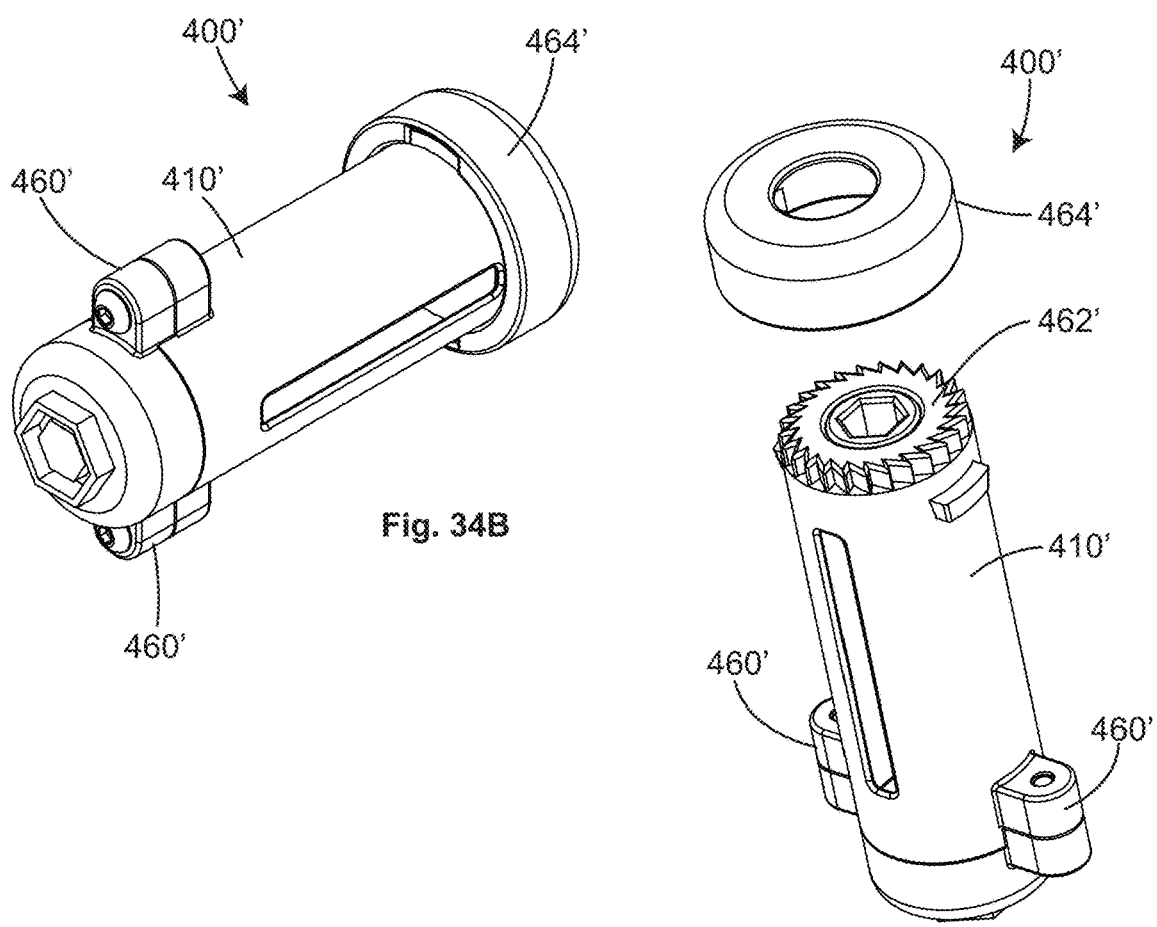
Fig. 34B
Fig. 34C

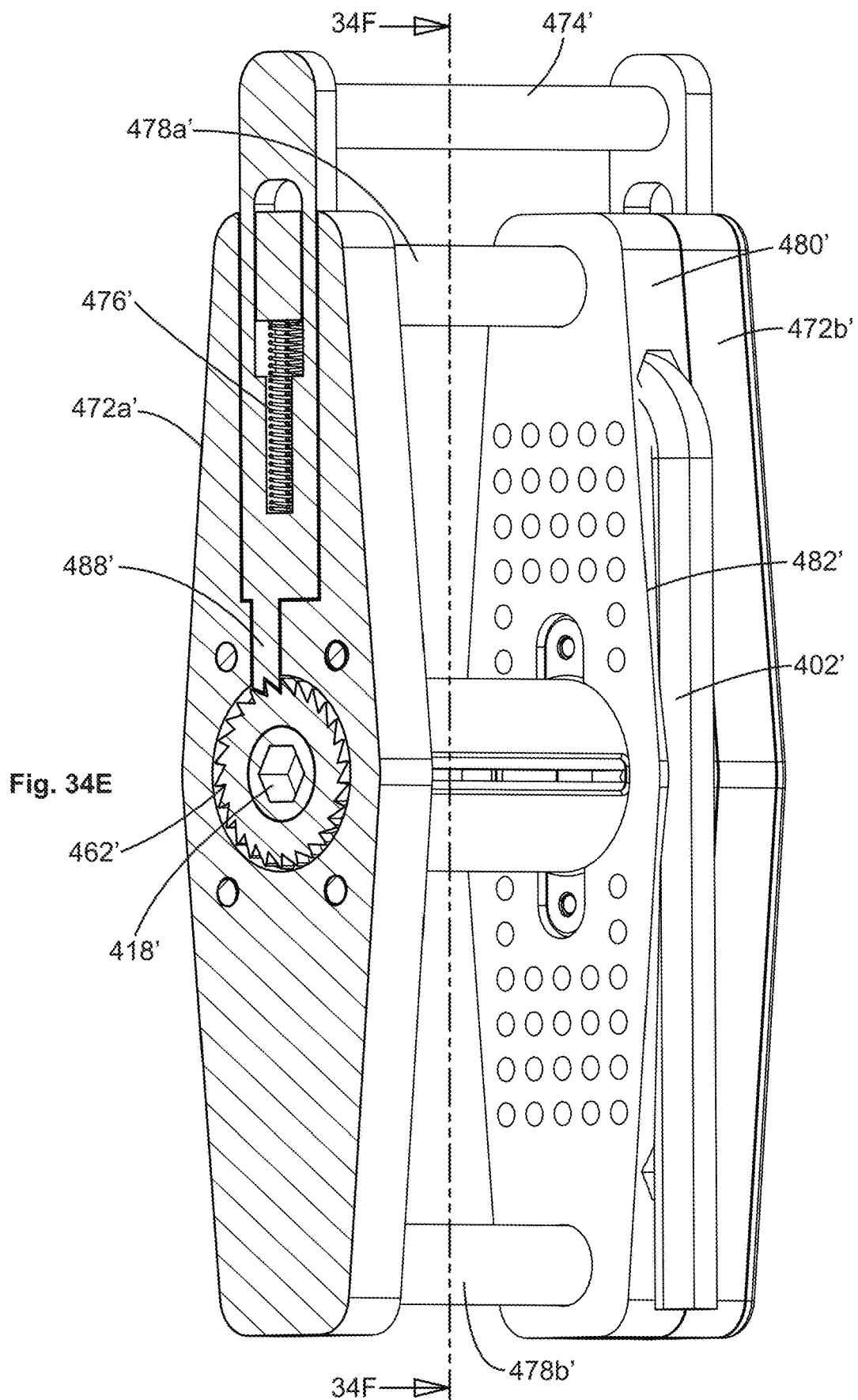

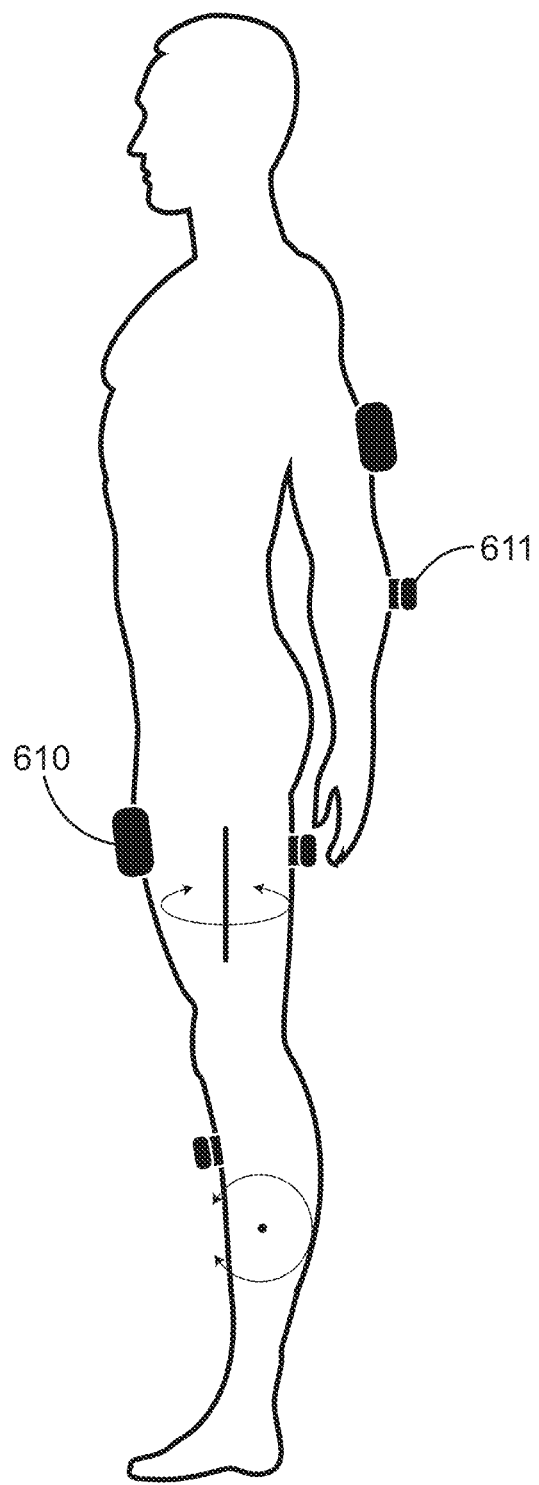
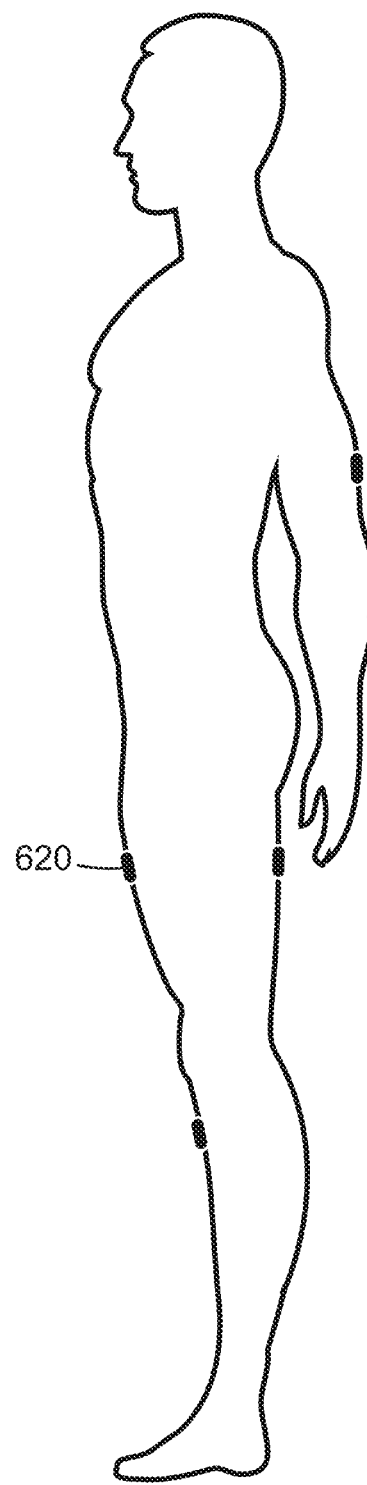
Fig. 39A
(PRIOR ART)
Fig. 39B

TOOL OPERATED ADJUSTMENT DEVICES, FIT SYSTEMS, AND LINE TENSIONING SYSTEMS

CROSS-REFERENCE TO RELATED APPLICATIONS

This application is the National Stage of International Patent Application No. PCT/US2020/036128 filed on Jun. 4, 2020, which claims priority to U.S. Provisional Application 62/857,320 filed Jun. 5, 2019, and to U.S. Provisional Application 62/937,808 filed Nov. 20, 2019, the entire contents of both of which are hereby incorporated herein in their entireties.

BACKGROUND

1. Field

The present disclosure relates to low profile adjustment devices for use with various for articles, fit system, and line tensioning systems.

2. State of the Art

How well a wearable article or device fits the body is highly important in the daily function of humans or even for animals. For example, wearable articles and devices can include, by way of example, garments, shoes, backpacks, sporting gear, wearable protective devices, sporting braces, orthosis, and/or prosthesis. Several factors can be weighed in how appropriate or satisfactory a wearable article or device fits the body, including whether the fit system transmits satisfactory load, provides satisfactory stability, suspends on the body, provides efficient congruency of the article or device during motion, provides sufficient mobility, is easily fitted, and/or is comfortable. These factors can be considered determinates in how appropriate or effective the fit of the article or device is on the body and they are directly related to how the article or device is secured or fastened to the body. Generally, the wearable articles or devices are secured to the body by tightening around the body. The mechanisms and associated methods of how articles or devices are secured to the body are hereby referred to as fit systems.

Fit systems and related devices and methods generally are operably attached to one or more flexible elongate members or tension lines (such as straps, cables, laces, etc.) with one or more attachment points or interfaces to the article or device. The attachment points or interfaces may decrease in distance relative to one another or relative to the fit system, which can be referred to as contraction or shortening. Such contraction can involve decreasing the effective length of the flexible elongate member(s) of the fit system and possibly increasing the amount of tension (or tensile loading) experienced by the flexible elongate member(s) of the fit system. Such contraction can occur when tightening or closing or other movement of the article or device with respect to the body. Alternatively, the attachment points or interfaces may increase in distance relative to one another or relative to the fit system, which can be referred to as extension or lengthening. Such extension can involve increasing the effective length of the flexible elongate member(s) of the fit system and possibly deceasing the amount of tension (or tensile loading) experienced by the flexible elongate member(s) of the fit system. Such extension can occur when loosening or other movement of the article or device with respect to the body.

The determinates of the appropriateness and effectiveness of a fit system may be associated with design elements of the fit system including: the mechanisms and associated methods for contraction and extension, the inherent mechanical advantage of a given fit system, mechanical reliability of the overall system and toughness of individual components, maximum load and tension, distance between the attachment points or interfaces in the maximum contracted and maximum extended positions, profile height of the fit system, width and length of the fit system, rigidity of the fit system and its components, whether the contraction and extension is incremental or analog in nature, how smooth or abrupt is the contraction and extension, attachment requirements of the fit system, system weight and suspension forces provided by the fit system, and pressure distribution of the fit system.

The mechanism/s and associated methods of use weigh heavily on the user experience of the fit system and is the driving factor for many of the other determinates of the fit system. For example, a mechanism may be mechanically effective but may have poor ergonomics. The mechanism may also affect the speed and direction of the contraction and extension. For example, the gear ratio mechanism within a fit system may provide high mechanical advantage, but a slow speed of contraction, which may be ideal for some applications and too slow for others. In another applications, the speeds of contraction and extension may be key for some applications. For example, certain military applications such as a fit system for a military aid pack or backpack may need to have a high speed of contraction and very high speed of extension such that the operator can quickly remove the pack if they need to quickly become mobile to avoid harm. In this application, a high mechanical advantage for contraction or extension may be less important because most users would have a relatively high level of strength. In still other applications, the direction of pull of the contraction or extension may be important. For example, contracting in a single direction could cause misalignment of a knee joint in an orthosis as the user tightens the brace onto their body. In these cases, a balanced, dual direction fit system would be more appropriate. How easily a fit system performs contraction and extension is paramount in its ability to deliver optimal fit and user experience. Many users of orthopedic devices have compromised strength and/or dexterity so mechanisms and methods that make the fit system easy for them to contract to the desired amount and easily extend for release is a huge need and large benefit. Conversely, if a fit system is so easily engaged for contraction or extension that it is accidentally triggered, that can be a serious functional problem as well. Mechanism and methods drive other factors such as the inherent mechanical advantage of the system and the increments of tightening. Some applications may require small increments of contraction or extension whereas others may be optimized by larger and therefore faster increments of change.

In addition, some mechanisms and methods of fit systems may allow for an opening or separation between attachment points or interfaces whereas others may be better suited or even require the fit system to remain as a single unit between attachment points or interfaces. Some applications may require that a fit system opens up in order to don and doff the device while others may not. For example, a leg brace may require that users open up the device in order to place their leg into the device whereas protective pants for motorcycle riders may allow for a waist fit system stay in one piece and loosen only while they pull it up to their waist.

The inherent mechanical advantage of a fit system is a byproduct of the mechanisms and the methods associated with the fit system. Such fit system can provide a quantifiable mechanical advantage ratio which is the amount of output force over the amount of input force. The speed or time needed to contract or extend the fit system a given distance is usually inversely correlated with mechanical advantage such that when mechanical advantage is high, speed is low and vice versa. Many applications differ in the mechanical advantage requirement, but most applications have a specific ratio or range of ratios that is optimal for function. If the mechanical advantage is too high or more than required for a given application, it may unnecessarily sacrifice speed. Mechanical advantage within a fit system directly relates to the maximum tension and load of the system. The maximum tension and load of a fit system is described in detail below.

The mechanical reliability and toughness of the fit system relates to the materials utilized by parts therein, geometry, dimensions, and manufacturing methods. Specifically, the overall fit system may only be as strong as its weakest link. Some parts can fail and cause catastrophic failure while others may not. Failure of some fit systems could lead to the users getting trapped or stuck in their device or with their device. In other situations, the user may be highly dependent on the device. Failure of a fit system could potentially even contribute to a fatal accident. Reliability is therefore extremely important especially in certain circumstances and applications.

Maximum tension of a fit system is typically dependent on the maximum tensile loading of the flexible elongate member(s) of the fit system. In many applications, the maximum tensile loading relates directly to the maximum input force multiplied by the mechanical advantage. The input force is most often the manual force of the user but may be the force imposed by another person or an electronic or other automated system. The input force is transferred to the fit system members via the mechanisms within the fit system which may or may not include mechanical advantage. The tensile loading of the flexible elongate member(s) of the fit system can transfer load or force onto the user's body. Generally, the load is directed into the body or, in other words, towards the center of the body's long axis or the long axis of a limb but may also be slightly oblique to the direction directly towards the long axis. If such loading forces are directed in an angle that is too oblique to the long axis they will likely cause the device to shift proximally or distally on the body unless counterbalanced by a geometric feature of the body or other feature. The amount of load transferred onto the body can also related to other factors. For example, the amount of body exposure from the device seen by the fit system will affect the how much of the tension force is transferred directly onto the body or into the device.

The loading directed into the body can apply pressure to the body. Generally, the pressure distribution applied to the body is dependent on the amount of loading applied by the fit system to the body divided by the surface area of the applied loading. Pressure distribution of the fit system is explained in further detail below. In many cases, the fit system can transfer some tension forces onto the device (for example, by the device changing shape or reducing in volume), thereby reducing load applied to the body. The amount of desired load or optimal load delivered onto the body by the fit system may differ per application, as the body changes, during activity changes, within certain movements, in certain positions, and/or over time. Although the optimal loads may vary per application and other variables, optimal performance is generally seen within a definitive range. The humans and animals generally prefer a similar range of load and associated pressure onto the body and within specific segments of the body. Beyond the level of preference, loads and pressures that are beyond a recommended range may cause a reduction in blood flow and/or other damage, discomfort, or pain. Conversely, if loads and pressures are too low, the device may fall down on the body or be loose on the body which may lead to damage, discomfort, or pain.

The maximum effective length of the flexible elongate members of the fit system can be referred to as the travel within a fit system. Travel within a fit system may relate to the amount of space available for a flexible elongate member to collect into the fit system or the distance of linear teeth in a ratchet ladder. The available amount of travel within a fit system may limit the amount of load that a fit system can deliver onto the body in that the maximum travel may be reached before the user gets to their desired amount of load onto the body. Travel may also directly affect device sizing in that a fit system with greater travel is likely to accommodate a wider range of body sizes and vice versa. These factors might suggest that fit systems should always include a maximum or large amount of travel. However, while increased travel may be beneficial, it often has a negative or inverse correlation on other determinates of the fit system such as the size, profile, weight, and other factors discussed below.

The profile height of the fit system is extremely important to product developers and end users. Profile height refers to the distance that the fit system protrudes away from the body or, in other words, how much it sticks out. Developers and end users have a strong preference or requirement for the fit system to have a low-profile for the aesthetic look and finish quality that they demand. Moreover, the profile height also plays a role in function and safety. If a fit system has a large profile height it will have a higher risk of catching on things or it may make it difficult or impossible to wear clothing over the fit system. Beyond these undesirable attributes, a fit system with a large profile can be a significant risk of injury due to the fact that if the user falls or bumps into something, the bulk of the fit system can be pushed into the body and can cause injury.

Similar to the profile height, the width and length of a fit system may also be important for applications of use. Width or length can limit applicability in some cases that may have a limited surface area of application. For example, shoes have a limited surface area that is acceptable for a fit system. Fit systems may be limited in their applicability to shoes if their width or length is over 45 mm or even 35 mm in some cases. However, beyond surface area limitations, larger width and length are far more acceptable for most applications fitting the body as compared to profile height.

In some cases, fit requirements can be very specific and a distance of one millimeter can be the difference in too loose and just right. In these cases, an analog fit system that can adjust in a continuous and controlled manor may be ideal. In other applications, incremental tightening provides the appropriate amount of fidelity while enabling for a wider array of fit system mechanisms. Incremental systems are often faster than analog systems that provide a control at a micro level. All incremental systems are not created equal. Some incremental fit system may offer small increments like 1.5 millimeters whereas others may offer large steps of 6 millimeters. Requirements for the distance between increments are specific per application but in general the range is between 0.5 mm and 8 mm. Regardless of whether a system is incremental or analog, the mechanism or method of use may provide a smooth transition as it is used to adjust fit or it may provide an abrupt experience. In general, the experience is understandably more favorable if it is more controlled and smooth. However, some cases require fast release or removal of a device.

Various fit systems have been proposed. An example of one such device is described in U.S. Pat. No. 9,867,430 (Boa Technologies). This prior art stacks fit system mechanisms and members vertically and thereby has a large profile height. The profile height of the high mechanical advantage (approximately 6 to 1 mechanical advantage) version of the commercial embodiment of this technology is approximately 33 mm high. The profile height of the mid-power mechanical advantage (approximately 2 to 1 mechanical advantage) of the commercial embodiment of this technology is approximately 23 mm high. The profile heights for this technology are excessive for many applications. This commercial technology is also limited in mechanical reliability. The system utilizes cables or laces that are approximately 0.8 to 1.0 mm thick and can fail during use of many applications. Additionally, release is abrupt and may be shocking and jarring to the user. Moreover, users with poor hand dexterity lack the capacity to wind or release the tension line of the fit system.

Ratchet ladders have sufficient mechanical advantage for many applications, but the ladder strap teeth often cannot accommodate angles greater than 30 degrees without skipping. Additionally, release is abrupt and may be shocking and jarring to the user. Also, these systems are generally between 25 mm and 45 mm and are thereby excessively bulky in profile for many applications.

Ratchet straps offer large mechanical advantage and high mechanical reliability, however their profile height, difficulty and abruptness in releasing mechanisms, and challenge of donning wherein one needs to feed a strap through a split axis and hold the strap in tension in order to start it: all make for these systems to be inapplicable as a fit system.

Over-center cam buckles serve as fit systems for ski boots and other similar products. These fit systems and other similar products effectively provide mechanical advantage when they are attached to rigid plastic structures on both sides but they do not include fastening mechanism that allow them to mount to a strap and the base of the over-center cam would create high peak pressures if it were used on a loose strap due to its small base of support. The catch mechanisms for these devices are also not designed to work with a loose strap and create difficult ergonomics if they are used with loose straps. Moreover, these systems offer no security latch mechanisms to maintain the strap in the closed position, do not offer macro tightening and loosening, and are highly dependent on the specific geometry (angles and contours) of the application. All of these factors amount to over-center systems not being applicable to products fitting the body with the exception of products that include hard plastic rigid shells like ski boots.

Webbing straps with hook and loop fasteners (sold under the tradename VELCRO) is often used as a fit system in almost all devices that fit the body ranging from shoes to neck braces. The ubiquitous use of hook and loop systems may relate to its low cost, accessibility, low-profile, and ease in integration into product development; all fit system factors that affect a company's motivation to integrate a fit system into their product beyond the end user attributes discussed in detail above. Buckles, fasteners, and chafes are often utilized in combination with hook and loop fasteners in order to add some mechanical advantage and/or provide greater ease of use. Although hook and loop fasteners are widely used, end users often complain of the noise it makes during removal, how it often attaches to unintended materials and surfaces, how it collects lint, how it is difficult to tighten and loosen especially for those with low strength capacity, and how it tends to wear out with prolonged cycle use.

The most common fit system utilized for shoes is traditional laces. Laces offer minimal mechanical advantage but that is all that is needed in most shoes since the dorsum of the foot offers a large surface area to suspend on. Even though the need for mechanical advantage and suspension are low, fast, and ergonomic methods to tighten and loosen shoes is still desired.

Line tensioning systems and related methods can generally include one or more flexible elongate members (such as straps, cables, wires, etc.) with one or more attachment points or interfaces to an article, device, or structure. Similar to fit systems, the attachment points or interfaces may decrease in distance relative to one another or relative to the line tensioning system, which can be referred to as contraction or shortening. Such contraction can involve decreasing the effective length of the flexible elongate member(s) of the line tensioning system and possibly increasing the amount of tension (or tensile loading) experienced by the flexible elongate member(s) of the line tensioning system. Alternatively, the attachment points or interfaces may increase in distance relative to one another or relative to the line tensioning system, which can be referred to as extension or lengthening. Such extension can involve increasing the effective length of the flexible elongate member(s) of the line tensioning system and possibly deceasing the amount of tension (or tensile loading) experienced by the flexible elongate member(s) of the line tensioning system.

The determinates of the appropriateness and effectiveness of a line tensioning system may be associated with design elements of the line tensioning system including: the mechanisms and associated methods for contraction and extension, the inherent mechanical advantage of a given line tensioning system, mechanical reliability of the overall system and toughness of individual components, maximum load and tension, distance between the attachment points or interfaces in the maximum contracted and maximum extended positions, profile height of the line tensioning system, width and length of the line tensioning system, rigidity of the line tensioning system and its components, whether the contraction and extension is incremental or analog in nature, how smooth or abrupt is the contraction and extension, attachment requirements of the line tensioning system, system weight and suspension forces provided by the line tensioning system, and pressure distribution and loading provided by the line tensioning system.

SUMMARY

In accordance with a first aspect, adjustment devices are described herein that may be useful in a variety of applications, including for wearable articles and tension systems. The adjustment devices described herein include a tool-operated mechanism that drives a spool for winding a tension line.

According to a first embodiment, a low-profile tension adjustment device is provided for winding and unwinding a flexible elongate member (i.e., a tension line cable or lace). The adjustment device may include a housing comprised of a base and a cover, and a spool surrounded and housed by the housing. The spool is rotatable relative to the housing using an adjustment tool, such as a standard and readily available hex shaped key (i.e., an "Allen wrench" or "Allen key"), ratcheting wrench, or power tool. The hex shaped key can be in the appropriate size to apply the necessary force for an application. A driving portion of the adjustment tool and a control port or socket of the adjustment device are configured for mating engagement. In an example of a tension adjustment device adapted to mate with a hex-shaped wrench, the control port includes a hexagonal port that mates with the hexagonal driving end of the tool. The control port alternatively may be provided with other non-circular shapes (besides hexagonal) by way of which a torqueable mating engagement can be made with an adjustment tool that is pushed into or otherwise inserted into the port. When the flexible elongate member is connected to the spool, the tool may be used to rotate the spool to draw the flexible elongate member into the housing and onto the spool, which may impart tension to the flexible elongate member.

Retention of flexible elongate member wound onto the spool can be controlled by a retainer (e.g., a mating hex-shaped retainer), which is biased into engagement with the control port and may be configured to be rotationally fixed with respect to the housing. For example, the base of the housing may include a post configured to be received by the retainer. In such an example, the post and the retainer may have a mating connection that prevents relative rotation between the retainer and the housing.

The control port, the spool, and the retainer may be coaxially aligned along a central longitudinal axis. The retainer may be configured for relative translation with the spool and the housing along the longitudinal axis.

In embodiments, insertion of the tool into the control port may cause the retainer to translate along the longitudinal axis against the bias of the spring, which may release the spool to permit the spool to rotate relative to the housing. Any tension in the elongate member is transmitted to the tool and the hand of the user, who is free to wind or unwind the elongate member by rotating the tool relative to the housing. The user holding the tool can feel the amount of tension they are inputting to the device. Some prior art ratcheting devices block or otherwise do not provide tactile feedback to the user.

In embodiments, snap fit indicating features (e.g., tabs) may be provided between the housing and spool which can provide auditory and haptic feedback to the user as the spool rotates relative to the housing to indicate when the retainer is aligned with the spool. When the spool and the retainer are aligned at an indicating snap fit feature, the operator can remove the tool and the retainer will seamlessly engage with the hex shaped control port. In one exemplar embodiment where the retainer and the tool port are hexagonal, there are six indicating features. Thus, in that example, the minimum increment of rotational adjustment of the spool relative to the housing is sixty (60) degrees.

The adjustment device may be configured to allow the user to choose their preferred direction of tightening and loosening. For example, the spool defines holes for receiving the elongate element. The holes are surrounded by symmetrically filleted surfaces that have a large enough radius of curvature to avoid weakening the elongate member if wound in either rotational direction. This permits the user to rotate the spool clockwise or counterclockwise to collect the elongate member.

The elongate member wound around the spool, and any tension developed in the elongate member, can be fully or partially released by rotating the spool in a second direction opposite the first direction used to wind the elongate member. Rotating the spool in the reverse direction can be accomplished by the user rotating the tool in the second direction or by the user allowing the tool spin freely as tension in the elongate member drives the tool and the spool in the reverse direction.

In embodiments, the housing may include a flange or lip with anti-rotation features, such as notches, holes, or grooves. The device may be mountable to an article by connecting the flange or lip to a mounting surface of the article. This mounting option may be useful for integrating the device into the lamination of a prosthetic socket or 3D print of a prosthetic socket. Alternatively, a receiving feature (e.g., a receiving socket) configured to receive the flange or lip, can be part of a molded or machined into a part for integration into a mass manufactured product or garment. Such receiving feature may have anti-rotation features that align or mate with the anti-rotation features of the flange or lip to prevent relative rotation between the housing of the device and the receiving feature.

In embodiments, a plurality of exit ports or holes may be defined in the base of the housing for passage of the tension line through the housing to the spool. In one embodiment, four (4) exit ports are provided spaced ninety degrees apart with respect to the longitudinal axis. The plurality of exit holes allows a user to select holes for appropriate orientation of the elongate member for the specific application. In embodiments, the exit holes may include a blind hole to receive a cable or lace housing to control routing of the cable.

In embodiments, access to the spool for assembly or replacement of the elongate member is made possible by way of the removable housing cap, which can be removed and replaced by way of an adjustment.

In another embodiment, a toothed retainer is substituted for the non-circular port. The retainer may have a plurality of teeth circumferentially spaced near or at an outer diameter of the retainer. This arrangement spaces the teeth radially outward from the control port. The retainer may be biased by a biasing member (e.g., a spring) to engage with mating concentric teeth at or near an inner diameter of the spool. This arrangement of the teeth of the spool and the retainer can reduce the area of mating surfaces of the control port and retainer required for structural engagement directly under and within the control port. As a result, one advantage of this embodiment is that the overall profile height of the housing can be less than the profile height of the housing of earlier embodiments.

Moreover, having a larger number of teeth spaced relatively closer together, can allow for smaller increments (in terms of angular adjustment) of adjustment. In one example embodiment, the retainer has 20 teeth, such that the adjustment increments are 18 degrees, allowing for a finer adjustment than an example where 6 teeth permit a 60 degree adjustment increment.

Embodiments of the adjustment device may also include a mounting flange. The housing may have an external stitching flange that may be constructed for threaded connection to a mounting surface of an article, such as softgoods (e.g., clothing and footwear).

Another embodiment of an adjustment device may include one or more features of embodiments described hereinabove and may also include a ratcheting mechanism to maintain tension in the elongate member during and after collection of the elongate member. The ratcheting mechanism may include a one-way, biased pawl that engages teeth of the spool to prevent the spool from rotating in the second reverse direction, but otherwise permits the spool to rotated in the first direction. For partial or complete release of the spool to permit the spool to freely rotated in the first and second directions, the device may include a tension release port, separate from the winding port. The user may use the tool release port by inserting the tool into the tension release port, whereby the user can rotate the tool to cause the pawl to disengage from the spool. A user may choose to loosen tension in the elongate member by briefly (i.e., for a first period of time) rotating the tool in tension release port in a first direction to disengage the pawl from the spool, followed by (e.g., a second period of time) rotating the tool in a second direction opposite the first direction to re-engage the pawl with the spool for partial or incremental release. Also, a user may insert the tool into the tension release port and rotate the tool in the first direction to disengage the pawl from the spool and leave it disengaged until tension is fully released.

In accordance with another embodiment, the housing is intended to be free standing in-line with the elongate member and not directly mounted to another article. In such an embodiment, the device can slide from side to side on the tension line before tension line is collected. This can allow the user to more easily position the adjustment device at a desired location (e.g., centrally on the elongate member) before winding. Also, the adjustment device may include a direct and rigid coupling of the control port with the spool axle and may include a ratcheting mechanism that allows the user to rotate the spool in the first direction to collect the elongate member around the axle. The ratcheting system may be configured to maintain tension in the elongate member and prevent the elongate member from unwinding from the spool axle. Specifically, in embodiments, torque can be transferred and maintained with respect to the device housing by way of a ratcheting plate surrounded by the housing that is coupled to the spool axle. The ratcheting plate may permit the spool and its axle to be rotated in the first direction, while not allowing the spool and its axle to rotate in the opposite direction with respect to the housing and thereby the strap.

During winding of the elongate member into the housing, it is possible that a channel volume between the housing and the spool can become completely filled with elongate member. If the channel volume becomes completely filled with elongate member, the device can continue to be used to collect additional tension line around the outside surface of the housing by continuing to rotate the tool port with the tool in the same rotational direction used for winding the elongate member into the channel volume.

The free standing line-tensioning adjustment device embodiment may include a release mechanism that includes a release button, which when pressed, can disengage the ratchet plate from the spool to allow the spool to freely rotate in two rotational directions about its axis. The button and the ratchet plate can be displaced in a direction parallel to the axis of the spool and perpendicular to a plane in which normal forces act on the ratchet plate. Since release can be actuated perpendicular to the line of force, the ratchet plate can be released with relatively low force requirement even when tension on the elongate member is relatively high.

In a modification to the free standing tension adjustment device, the device is provided with a gear protruding externally through the housing, and an add-external secondary spool that couples to the housing and rotates with the spool inside the housing. The secondary spool guides the elongate member about the outside of the housing and facilitates additional take up of elongate member should the internal spool become filled.

Another embodiment of an adjustment device may include a dial to collect slack or loose cable or lace before a tool is inserted. A user can slide their finger, palm, or other surface across the dial to collect the loose lace then apply use of the tool to increase the tension.

It is specifically intended that the embodiments are shown as exemplar illustrations of features that are intended to be combined in any suitable combination, provided that it is physically possible to combine the features together.

All the adjustment devices can be used with hand tools, ratcheting tools, power tools, or other tools. Tools can be connected to the adjustment devices for storage or can be stored separately. For increased mechanical advantage, a larger (longer lever arm) tools can be used. Also, to increase mechanical advantage or increase the speed of rotation of the spool, embodiments of the adjustment device can include gears transmissions to increase or decrease the applied mechanical force, specifically to increase mechanical advantage or facilitate fine adjustment, using e.g., planetary gear systems, worm gears, and/or other gear mechanisms.

In other embodiments of the adjustment device, a laterally displaceable wedge or detent protrudes radially or laterally into the tool port. Such wedge or detent may be radially or laterally displaceable outward form the control port by the tool upon insertion of the tool into the tool port. Such action of the wedge or detent can be used to disengage the spool to permit the spool to rotate freely either rotational direction. Also, removal of the tool from the control port can cause the wedge or detent to move inwardly into the control port to reengage and lock the spool.

The tool-operated adjustment devices in accordance with this disclosure can have relatively higher mechanical advantage and lower profile as compared to prior art devices. Given that a tool is used to operate the device to make the adjustments, the devices may be ideally suited for applications where it desirable to prevent unintended adjustment a flexible elongate member under tension in an article.

BRIEF DESCRIPTION OF THE DRAWINGS

FIG. 23A is a top view of another embodiment of an adjustment device.

FIG. 23B is a top view of the adjustment device of FIG. 23A with a cover removed.

FIG. 23C is a transparent side view of the adjustment device of FIGS. 23A and 23B.

FIG. 28 is an exploded first perspective view of the device of FIG. 25.

FIG. 29 is an exploded second perspective view of the device of FIG. 25.

FIG. 34A is front perspective view of a modified version of the adjustment device of FIG. 25-33.

FIG. 34B is rear perspective view of the adjustment device of FIG. 34A.

FIG. 34C is a top perspective view of the adjustment device of FIG. 34A showing a removable cap displaced from over an accessory drive gear.

FIG. 34E is an assembled view of the adjustment device of FIG. 34A with a supplemental ratcheting assembly and the front wall of the ratcheting assembly shown in longitudinal section.

Prior Art FIG. 39A shows schematic prior art tension devices and fit systems connected to a human body.

FIG. 39B shows schematic exemplary fit systems using tension devices in accordance with the disclosure connected to a human body.

DETAILED DESCRIPTION

The present disclosure describes a number of embodiments of adjustment devices that employ a spool that interfaces to and supports at least one tension line. Thus, while some embodiments of the adjustment devices have been shown without connection to a tension line, all of the adjustment devices can be used with one or more tension lines. Note that each one the adjustment devices can be part of a fit system or a line tensioning system as described herein.

As used herein, a "tension line" refers to a flexible elongate member that can be gathered and wound onto a spool and unwound therefrom. The material of the tension line can be inelastic in nature or possibly have some elasticity. The tension line can be a cord, rope, cable, filament, or lace having a generally round profile, as well as flat straps having rectangular or square profiles. The material of the tension line can be any material typically used as a tension line in the same application. Thus, for a footwear application, the tension line used by the adjustment device in accordance with this description may be made from the same material currently in use for shoelaces. Also, the materials used may differ from those typically used for the application. The materials used for the tension line can include metal (e.g., steel) cable, and polyester webbing.

As used herein, a "fit system" refers to an adjustment device connected to a wearable article with at least one tension line (flexible elongate members such as straps, cables, wires, etc.) with one or more attachment points or interfaces to the article or device.

As used herein, a "line tensioning system" refers to an adjustment device connected to a non-wearable article or structure with at least one tension line (flexible elongate members such as straps, cables, wires, etc.) with one or more attachment points or interfaces to the article, device, or structure. Similar to fit systems, the attachment points or interfaces may decrease in distance relative to one another or relative to the line tensioning system, which can be referred to as contraction or shortening. The adjustment devices used in line tensioning systems may operate in space without being directly mounted to an article or structure.

Figure 1:
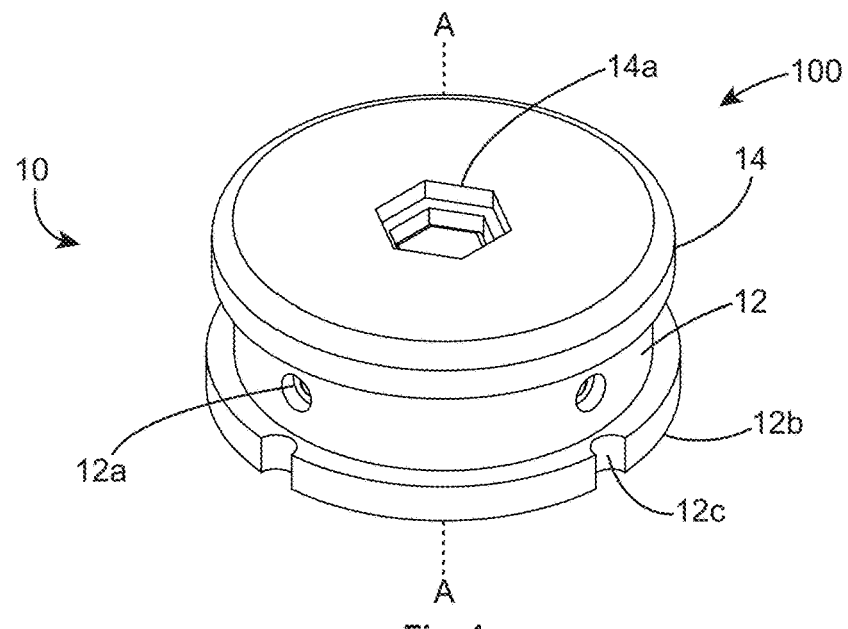
FIG. 1 is a top and side perspective view of an embodiment of an adjustment device in accordance with an aspect of the disclosure.
Figure 2:
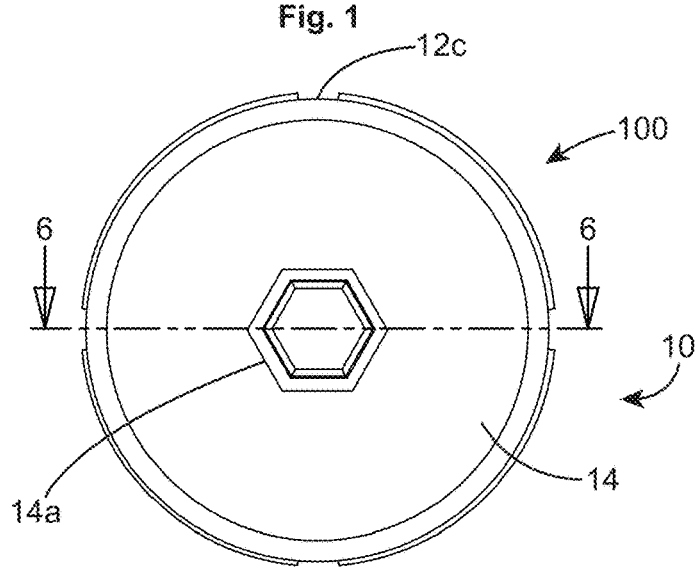
FIG. 2 is a top view of the adjustment device of FIG. 1
Figure 3:
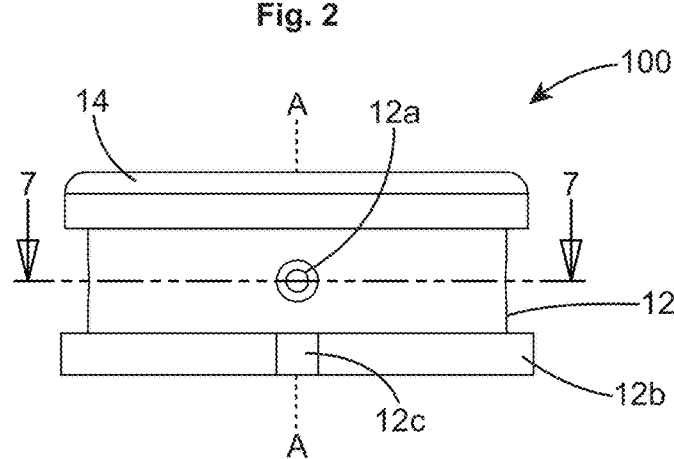
FIG. 3 is a side elevation view of the adjustment device of FIG. 1

FIGS. 1 to 13 show details of a first embodiment of an adjustment device 100 in accordance with an aspect of the disclosure. The device 100 is intended to be used with at least one a tension line that can be wound and collected by the device 100 and unwound and dispensed therefrom. FIGS. 1 to 3 show the device 100 assembled from its component parts shown in exploded views in FIGS. 4 and 5.

The device 100 includes a housing 10 that includes a base 12 and a removable cover 14. The housing 10 surrounds a spool 16, shown in greater detail in FIGS. 4 and 5. The base 12 defines a plurality of holes 12a through which the flexible elongate member 20 (FIGS. 8 and 9) can extend to connect to an axle 16a of the spool 16 on which the spool rotates about a first axis.

The base 12 has a mounting flange 12b that define notches 12c that can provide an anti-rotation feature for the device 10. For example, the mounting flange 12b may be received into a molded or otherwise formed material 702 of a wearable article, such as a prosthetic socket 700 (shown in FIGS. 10-11 and 40-42) such that the formed material secures the mounting flange 12b and protrudes into the notches 12c to prevent rotation of the flange 12b relative to the article.

Figures 4, 5:
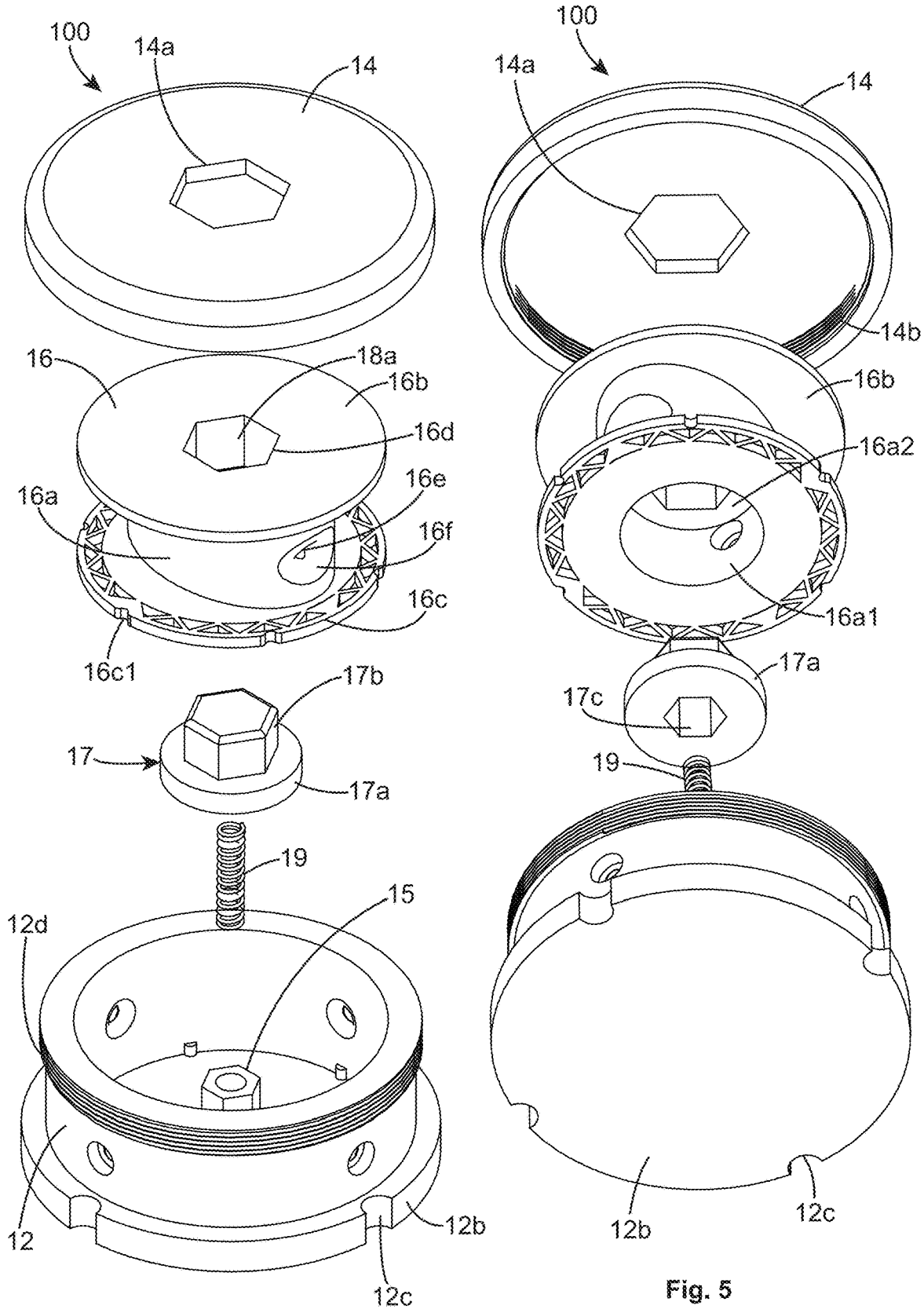
FIG. 4 is an exploded view of the adjustment device of FIG. 1, viewed from the top and side of the device.
FIG. 5 is an exploded view of the adjustment device of FIG. 1, viewed from the side and bottom of the device.

The cover 14 defines a central opening 14a. The opening 14a is coaxial with a central longitudinal axis A-A of the device 100. The central opening is shown as being a hexagonal opening, the shape of the opening defined in cross-section to the longitudinal axis. As shown in FIGS. 4 and 5, the base 12 has threads 12d that mate with threads 14b of the cover 14 to form a removable threaded connection between the cover 14 and the base 12. The cover 14 can be disconnected from the base to permit a user to access the spool 16 and tension line in the housing. A hex tool mating with the hexagonal opening 14a can be used to rotate the cover 14 relative to the base 12 to remove or reattach the cover 14 to the base 12.

Turning to FIGS. 4 and 5, the spool 16 is received and surrounded in the housing 10. The spool is coaxially aligned with the cover 14 and the base 12. The spool has an upper flange 16b and a lower flange 16c connected to ends of the axle 16a, which is hollow in the example to receive a sliding retainer 17, further details of which are described below.

Figure 12:
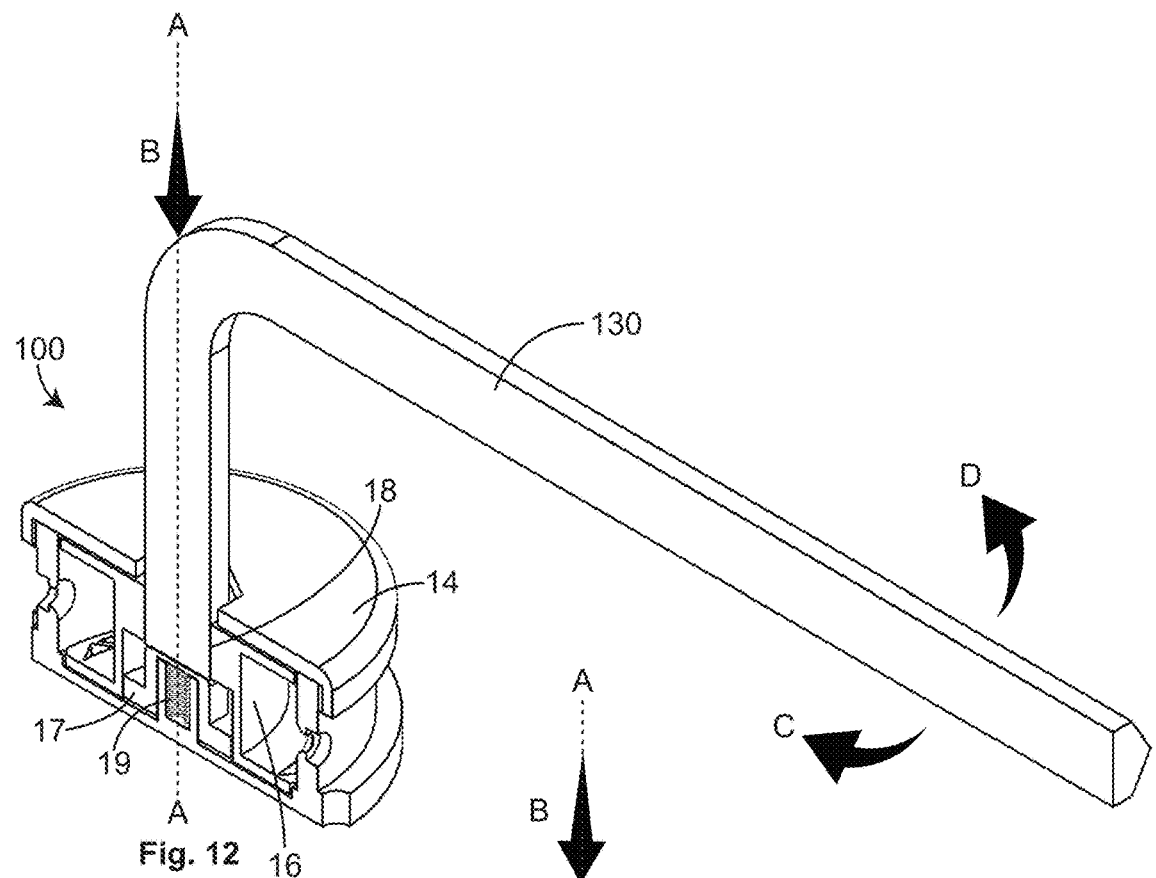
FIG. 12 shows the device in FIG. 6 with a tool inserted into a tool port of the device.

The upper flange 16b defines a central opening 16d aligned with the opening 14a in the cover 14. The central opening 16d is shown as being a hexagonal opening having a smaller diameter than the opening 14a. The central opening 16d leads into an upper end of a tool socket 18 that extends axially about a second axis and along axis A-A from the upper flange 16b to a shoulder 16a2 extending from an inner surface 16a1 of the axle 16a. Second axis is coaxial with first axis on axis A-A. The socket 18 is configured to receive a mating tool 130 (FIG. 12). The socket 18 is configured to prevent relative rotation between the socket 18 and the tool 130 relative to axis A-A. Specifically, in the example shown, the socket 18 is defined as a six-sided bore 18a that is configured to receive a six-sided tool, such as an end of a hex key 130 shown in FIG. 12.

Also, the interior of the axle 16a and the socket 18 are in communication with one another and are configured to receive a retainer 17 and to prevent relative rotation between the retainer 17 and the spool 16. The retainer 17 includes a lower base 17a and an upper protrusion 17b configured to be received in and mate with the bore 18a of the socket 18 from a lower end of the socket 18 to prevent relative rotation between the retainer 17 and the spool 16. In the example shown, the upper protrusion 17b of the retainer 17 has a hexagonal profile that is configured for axial reception along axis A-A into and out of the lower end of the bore 18a of the socket 18. The base 17a of the retainer 17 is configured to engage the shoulder 16a2 which provides a positive stop to axial movement of the retainer 17 into the bore 18a of the socket 18.

The retainer 17 also defines a central bore 17c (FIG. 5) extending axially along axis A-A from a lower side of the base 17a. In the example shown, the central bore 17c has a hexagonal profile to receive and mate with a hexagonal central post 15 (FIG. 4) extending axially along axis A-A and fixed to an upper surface of the mounting flange 12b on the inside of the housing 10. The engagement between the retainer 17 and the post 15 prevent relative rotation therebetween but permits the retainer 17 to translate along axis A-A relative to the post 15.

Figure 6:
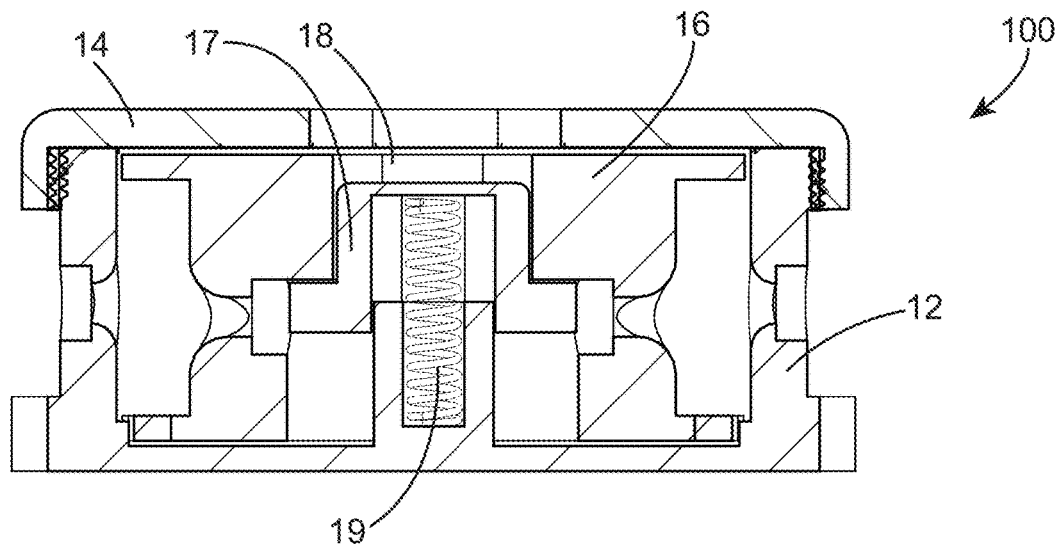
FIG. 6 is a view of the device of FIG. 1 along line 6-6 in FIG. 2.
Figure 10:
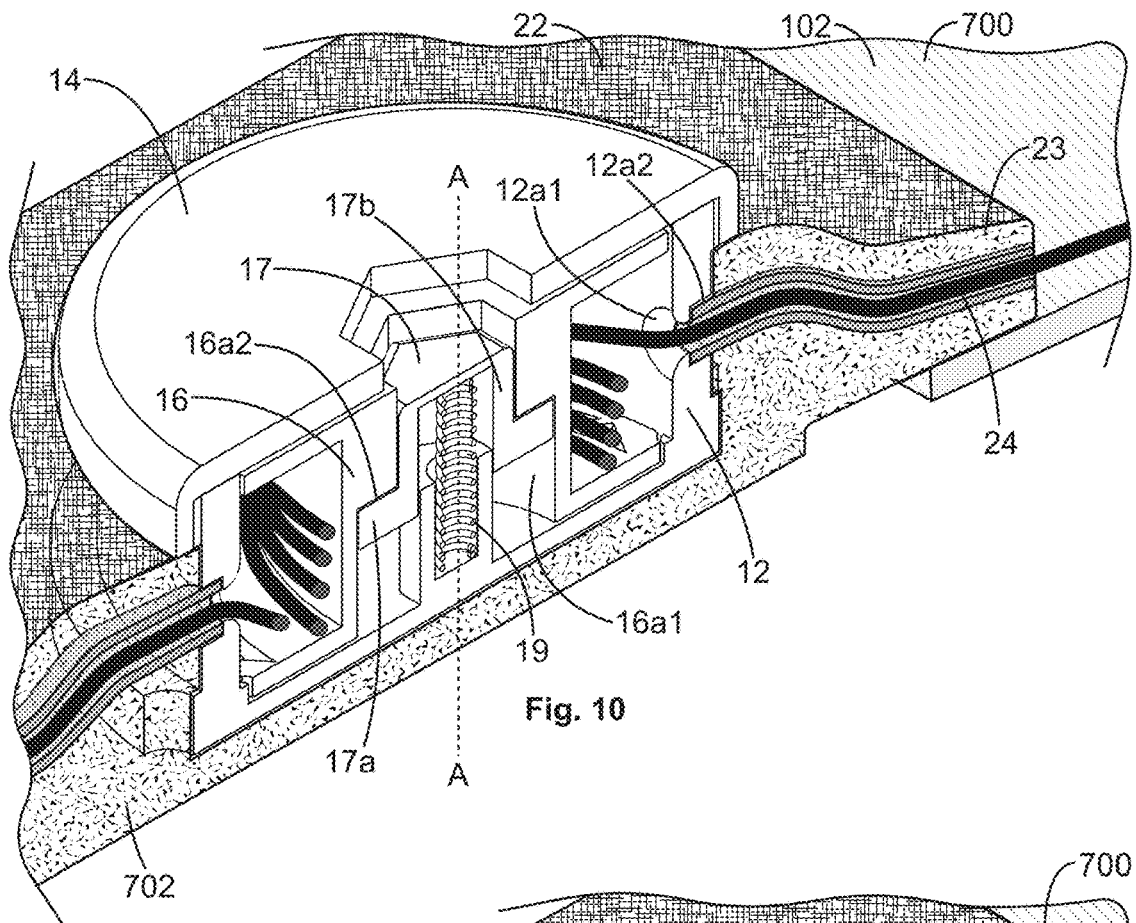
FIG. 10 shows the device of FIG. 9 viewed along line 10-10 in FIG. 9.

The retainer 17 is biased axially along A-A towards the upper flange 16b of the spool 16 with a biasing member 19, shown as a spring. As shown in FIGS. 6 and 10, when the bore 18a aligns with the protrusion 17b of the retainer 17 and no tool is inserted into the bore 18a of the socket 18, the retainer 17 is pushed upward into the bore 18a in an engaged configuration, thereby preventing the spool 16 from rotating relative to the retainer 17. Moreover, when the retainer 17 is in the engaged configuration with the spool 16, the retainer 17 remains rotationally fixed to the post 15. Thus, when the retainer 17 is in the engaged configuration with the socket 18, the spool 16 is rotationally locked relative to the housing 10.

Figure 11:
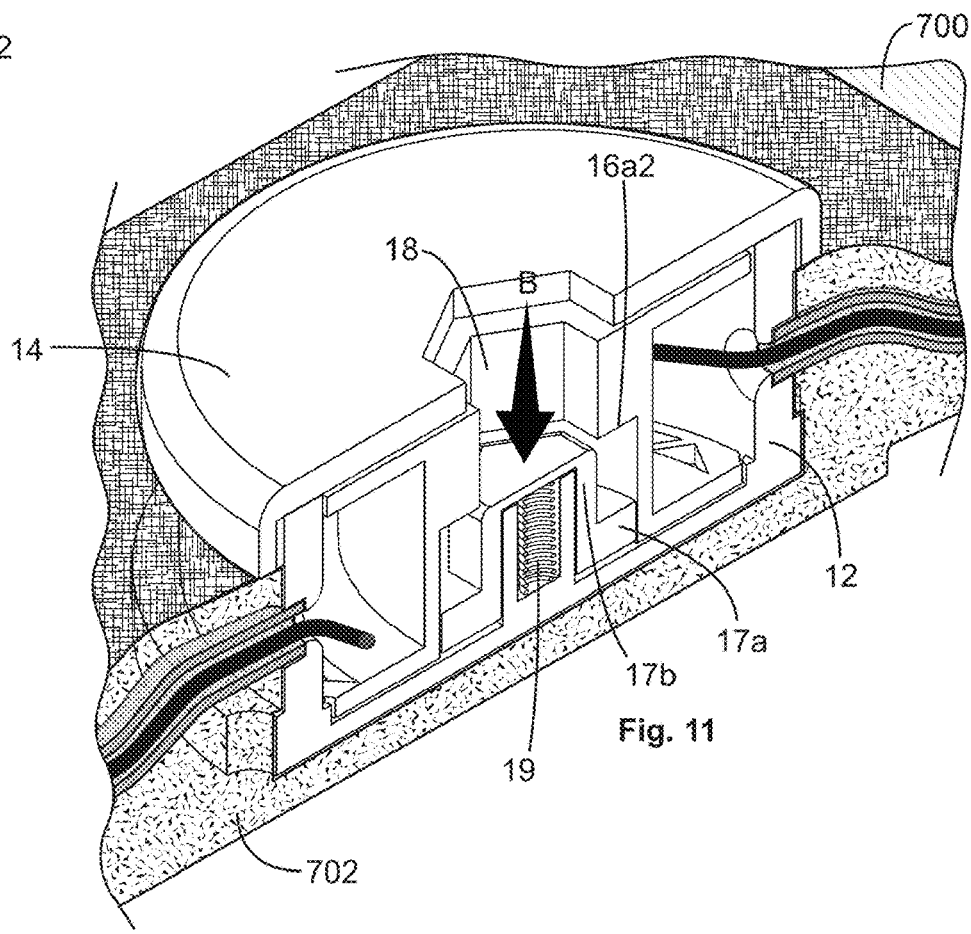
FIG. 11 shows the device of FIG. 10 upon pushing a retainer in a direction of the arrow shown.
Figure 13:
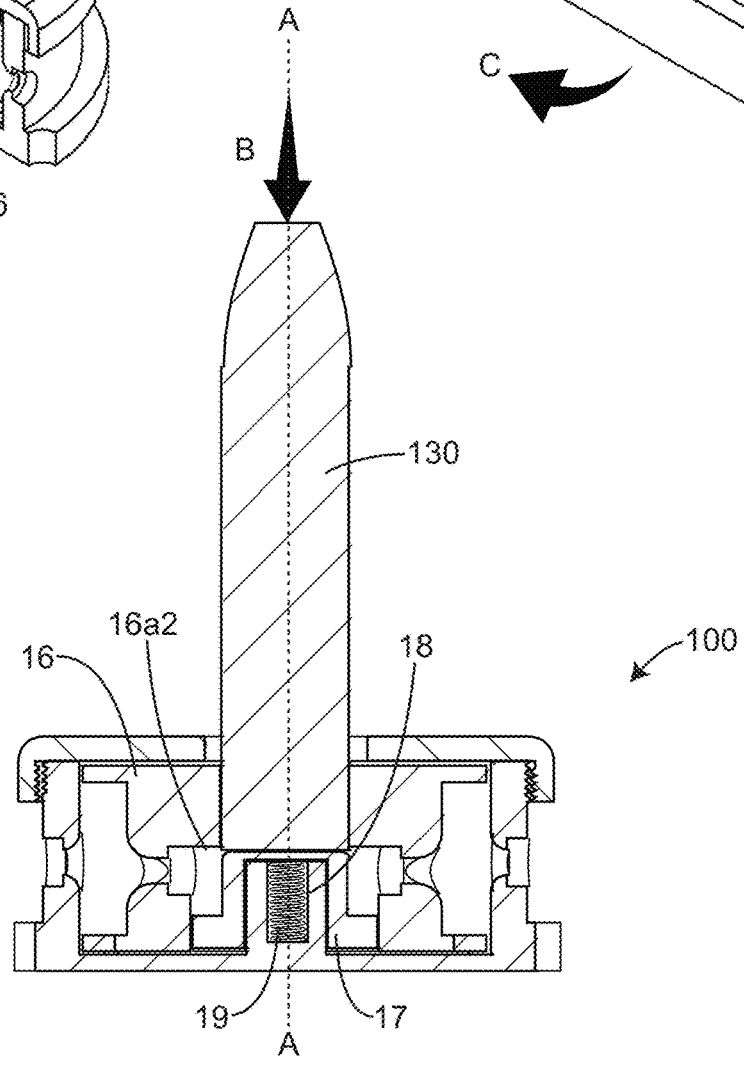
FIG. 13 is an elevation view of the device and tool of FIG. 12 after the tool is rotated ninety degrees with respect to the position shown in FIG. 12.

As shown in FIG. 12, the retainer 17 is configured to be disengaged from the spool 16 by inserting a tool 130 under manual force through holes 14a and 16d into the bore 18a of the socket 18 in a direction parallel to the axis A-A to connect the tool 130 to the socket 18 to translate the retainer 17 axially along A-A in the downward direction of the arrow B shown in FIGS. 11, 12, and 13. Once the retainer 17 is displaced completely below the shoulder 16a2, the spool 16 is rotationally disengaged from the retainer 17 so that the spool 16 can be rotated relative to the housing 10 about A-A using the tool 130, as shown in FIG. 13. The spool 16 can be rotated in either of the directions shown by arrows C and D in FIG. 12.

When a user is finished rotating the spool 16 in either directions C or D, the user can align the bore 18a with the retainer 17 so that the tool 130 can be withdrawn from the bore 18a in a direction opposite arrow B in FIG. 13 while the retainer 17 seamlessly is reinserted into and engages the bore 18a to retain tension in the elongate member and prevent the elongate member from unwinding.

Figure 8:
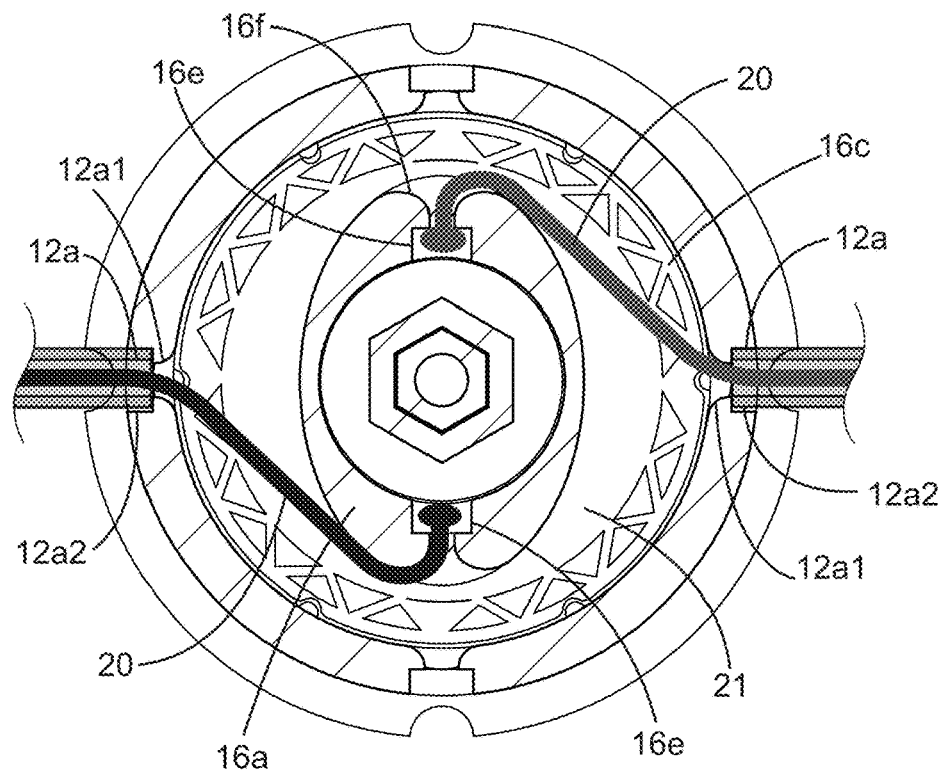
FIG. 8 is a view of the device in FIG. 7 with two elongate members connected to the axle of the spool before winding the elongate elements.
Figure 9:
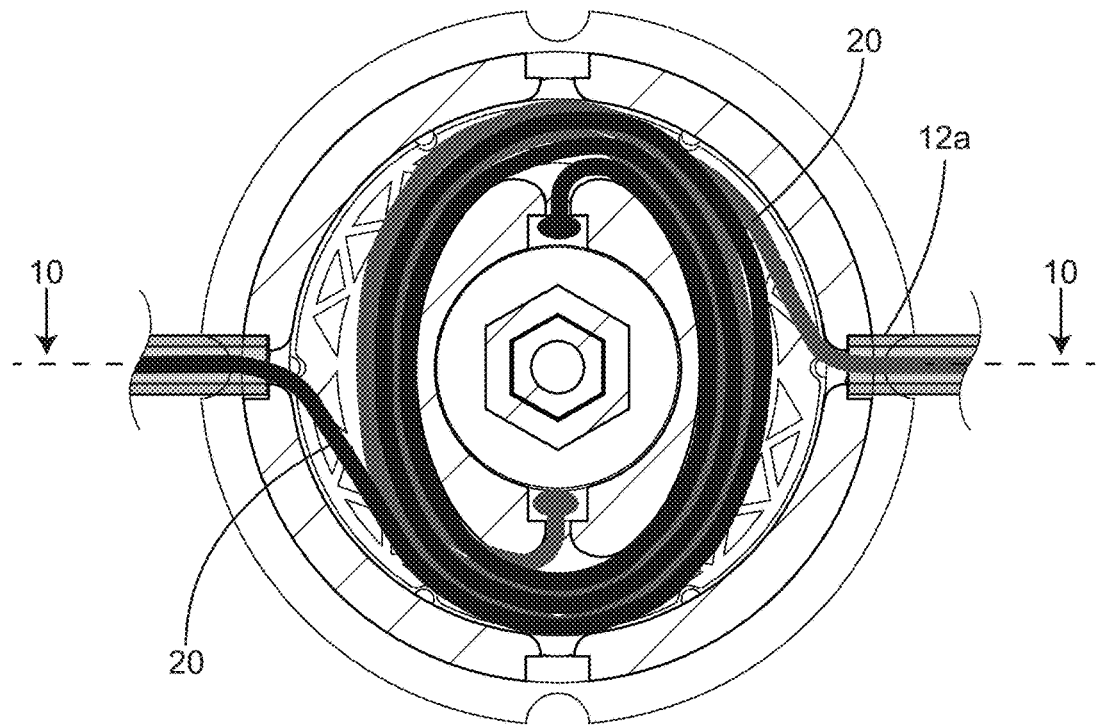
FIG. 9 shows the device of FIG. 8 after the spool is rotated a number of revolutions.

FIG. 8 shows ends of a tension line 20 connected to the axle 16a of the spool 16 and where the tension line 20 is not wound around the axle 16a of the spool 16. FIG. 9 shows the tension line 20 collected in the housing and wound around the axle 16a of the spool 16. FIG. 10 shows the device of FIG. 9 with the wound tension line 20 and with the retainer 17 in its engaged configuration. With the retainer 17 in the engaged configuration, the spool 16 is rotationally locked relative to the housing 10 so that any tension in the tension line 20 cannot cause the tension line 20 to be unwound by rotation of the spool 16 in an unwinding direction. However, as shown in FIG. 11, a user can reconfigure the retainer 17 by inserting the tool 130 to displace the retainer 17 from the bore 18a to disengage the retainer 17 from the spool 16, which can then permit the user to rotate the spool 16 to unwind the tension line 20 fully as shown in FIGS. 8 and 11.

Figure 7:
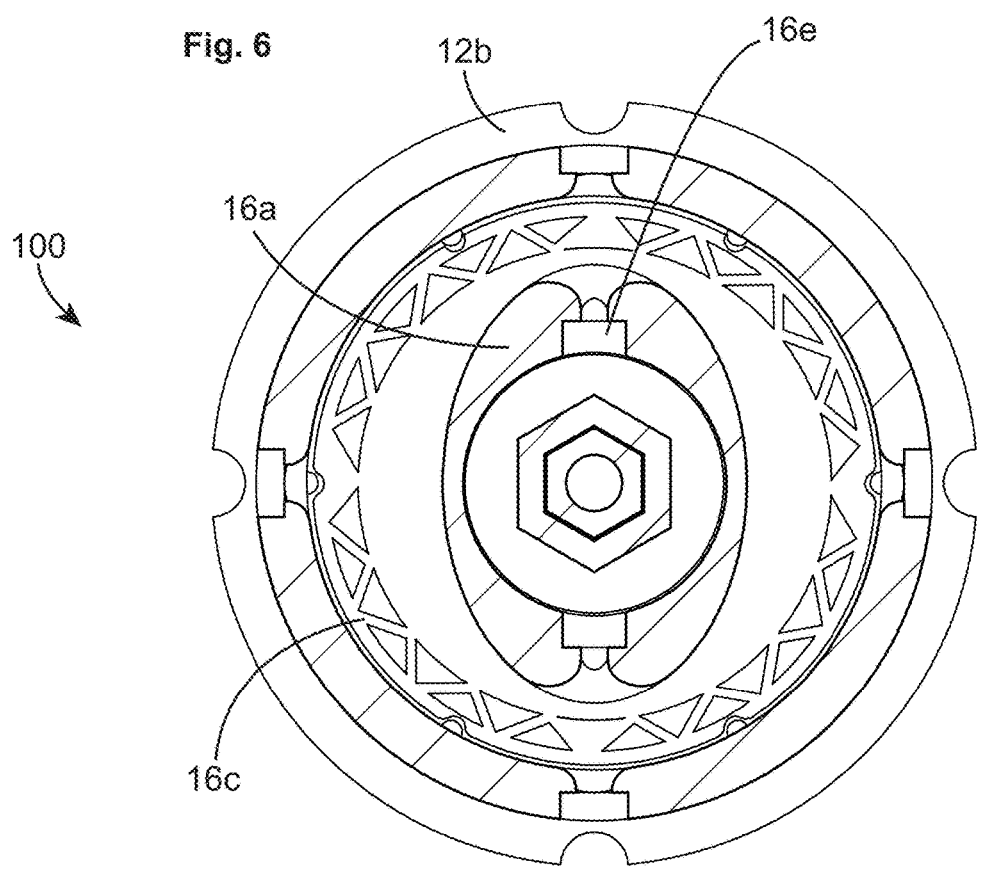
FIG. 7 is a view of the device of FIG. 1 along line 7-7 in FIG. 3.

The user can be guided in aligning the bore 18a into the engagement position with the retainer 17 as follows. The base 12 includes a plurality of circumferentially spaced protrusions 13. The lower flange 16c of the spool 16 defines a plurality of notches or grooves 16c1 that are configured to mate with the protrusions 13 when the retainer 17 is aligned with the bore 18a of the socket 18 (FIG. 7). When the user rotates the spool 16 with the tool 130, the engagement of the notches 16c1 and protrusions 13 provides haptic feedback to the user which can be felt in the hand of the user through the tool 130. The haptic feedback can be used as an indicator to the user that the retainer 17 is in the engaged configuration and that the tool 130 can be removed from the socket 18 without loss of tension in the tension line 20.

As shown most clearly in FIG. 7, the spool axle 16a has a generally oval cross-sectional shape. The oval shape increases the capstan effect or spool's ability to transfer and maintain tension forces. Also, the axle 16a defines diametrically opposed through holes 16e, each of which is surrounded by a rounded or filleted rim 16f for strain relief of the elongate member that are configured to extend through the holes. The holes 16e may be blind holes to retain a terminated end (e.g., an enlarged or flared end of the elongate member). In other embodiments, the elongate member may extend diametrically through the axle without terminating its ends at the axle 16a. Also, FIGS. 8 and 9 show the gradual bend of the elongate member 20 around the curved surface 16f that can provide a strain relief to prevent damage to the elongate member 20. The inner edges 12a1 (FIG. 8) of the holes 12a may also be rounded to protect the elongate member from abrasion and wear.

FIGS. 8 and 9 also show a collection volume 21 and a pathway between the spool 16 and the inner surface of the housing 10. The collection volume 21 is defined as the space between the spool 16 and the interior surfaces of the housing 10. As shown in FIGS. 8 and 9, as the tension line 20 is collected, the collection volume 21 is filled with the tension line. Eventually, if the entire collection volume 21 is filled with the tension line 20, the spool 16 cannot rotate any farther to collect additional tension line 20.

In FIGS. 10 and 11 the adjustment device 100 is seated or otherwise embedded in a material 22, which can be part of an article or may itself be a mounting member of the device 100 that can be attached to an article 102, as shown in FIG. 10. The material 22 may be molded around the housing 10. In the example shown, a portion of the base 12 below the cap 14 is surrounded by the material 22. Two cable routing passageways 23 are integrated into the material 22 and are in communication with the holes 12a. The passageways 23 are lined with a cable housing 24. Each cable housing 24 has an inner end (relative to the axis A-A) that is received in a bore 12a2 formed in the outer side of the base 12. Each bore 12a2 aligns with a corresponding hole 12a. The passageways and cable housings 23 and 24 extend outwardly (with respect to axis A-A) to outer ends from which the elongate member extends without being surrounded by the material 22 or cable housings 24.

Figure 14:
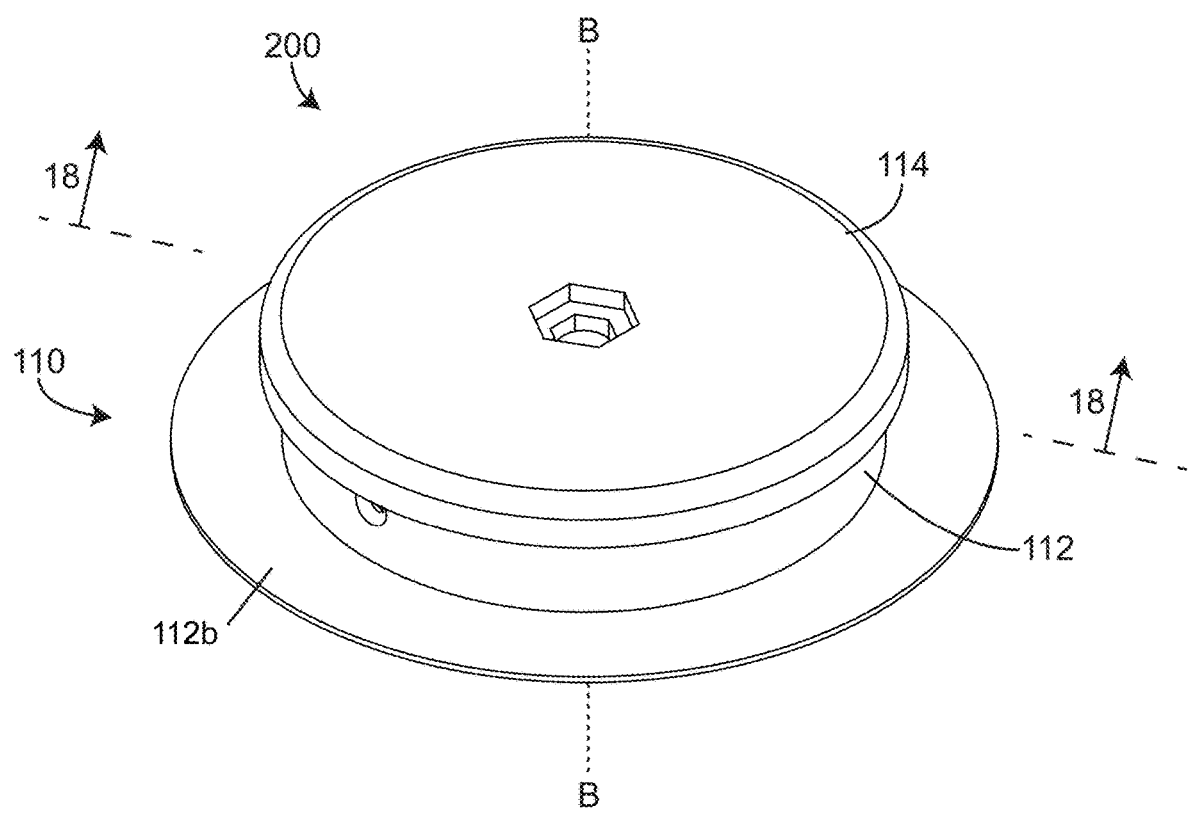
FIG. 14 is a top and side perspective view of another embodiment of an adjustment device.
Figure 15:
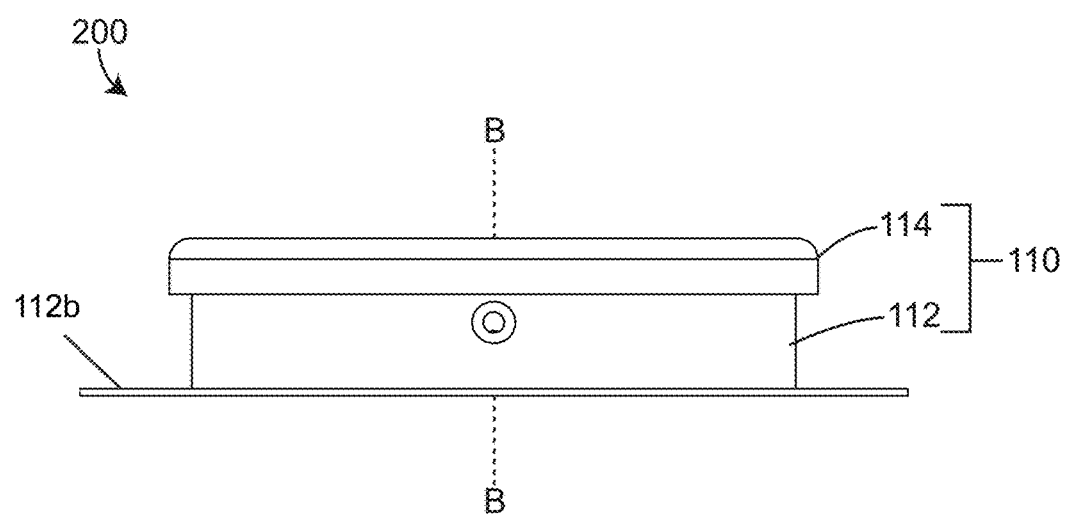
FIG. 15 is a side elevation view of the adjustment device of FIG. 14.
Figures 16, 17:
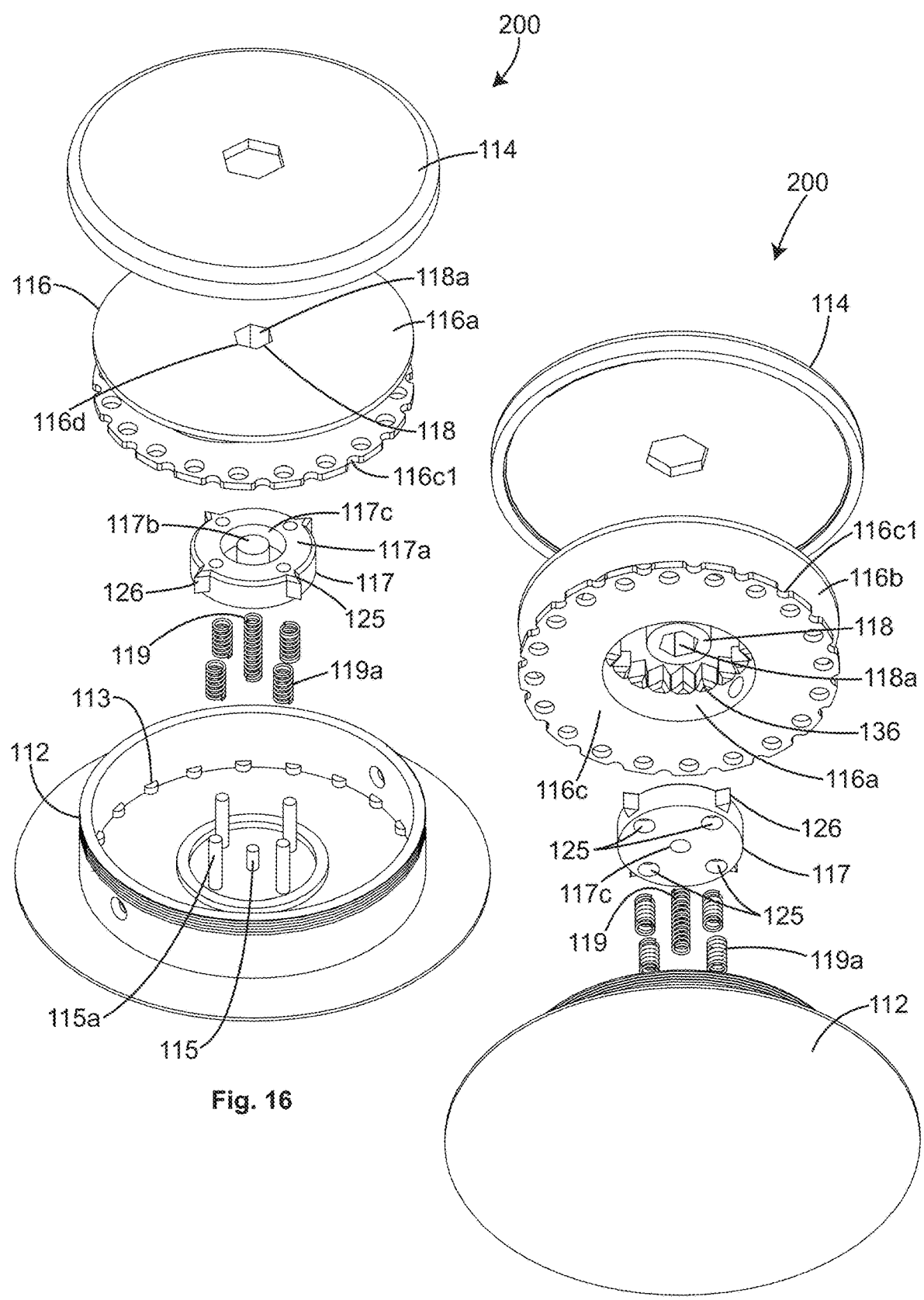
FIG. 16 is an exploded view of the adjustment device of FIG. 14 viewed from a top and side of the device.
FIG. 17 is an exploded view of the adjustment device of FIG. 14 viewed from a bottom and side of the device.

FIGS. 14 to 19 show details of a second embodiment of an adjustment device 200. In FIGS. 14 to 19 elements corresponding to those of device 100 are shown incremented by "100". The main differences between device 100 and device 200 lie in the construction of the spool 116, retainer 117, and posts 115, between the base 112 and the cover 114. The spool 116 includes a socket 118 with a central bore 118a. As shown in detail in FIG. 17, a plurality of teeth 136 extend along an inner surface of the axle 116a around the socket 118. As shown in FIGS. 14 and 15, the base 112 includes a stitch flange 112b.

Figure 18:
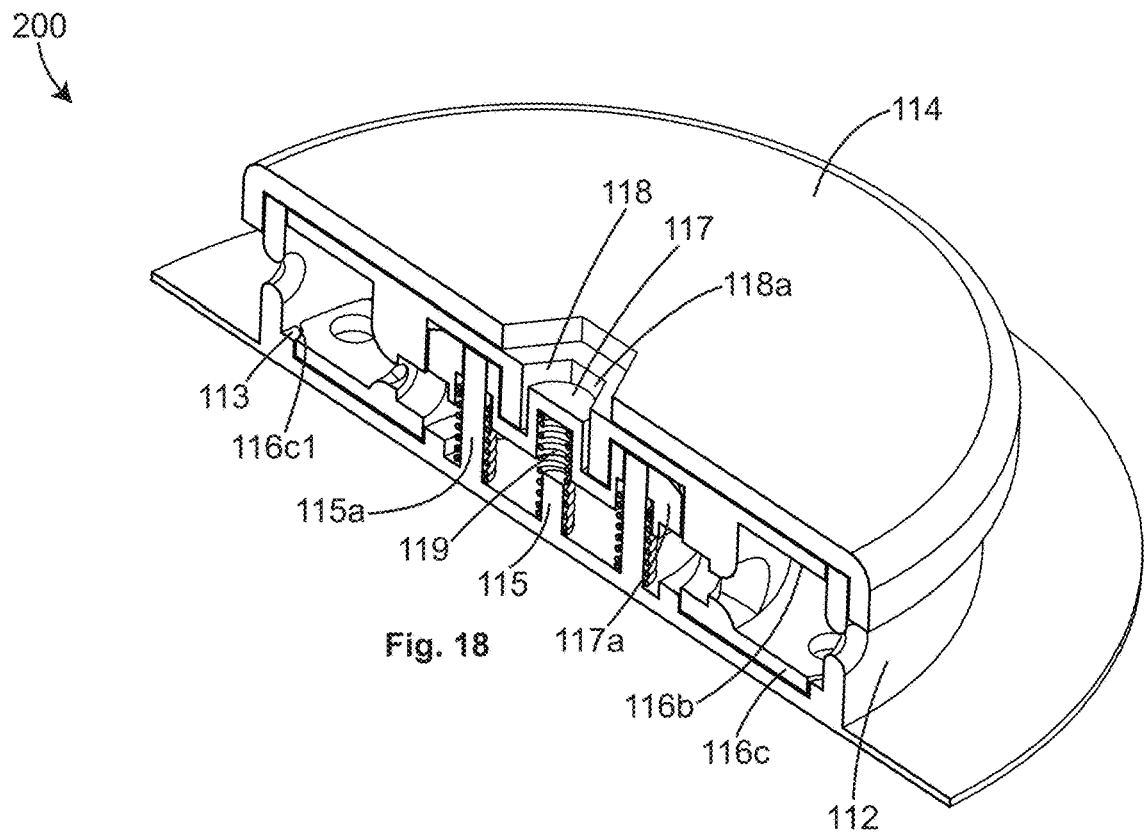
FIG. 18 is a view of the device of FIG. 14 along line 18-18 when the retainer is in a first engaged position with the spool.

The retainer 117 is shown as a central hub 117b surrounded by an annular rim 117a. Four radially extending teeth 126 extend from the annular rim 117a. The rim 117a is spaced radially from the hub 117b by an annular groove 117c that is configured to receive a lower end of the socket 118 when the retainer 117 is engaged with the spool 116. The teeth 126 are spaced 90 degrees around a perimeter of the rim 117b. The teeth 126 are configured to engage the teeth 136 of the spool 116 when the retainer 117 is in an engaged configuration with the spool 116, as shown in FIG. 18.

The retainer 117 has a central blind hole 117c that is configured to retain a biasing member 119, which urges the retainer axially along B-B towards the socket 118. A central post 115 extends along axis B-B and is configured to support spring 119 and be received in the blind hole 117c.

The retainer 117 defines four axially extending through holes 125 that are configured to receive and slide on four corresponding posts 115a arranged around central post 115. The posts 115a extend from the base 112 parallel to axis B-B (FIG. 15) and are arranged in a generally square pattern around the central post 115. Each post 115a extends through a corresponding spring 119a. Each spring 119a and 119 biases the retainer 117 upward towards the socket 118. The arrangement of the four posts 115a prevent relative rotation between the retainer 117 and the base 112. The four posts 115a are longer than the central post 115b. The retainer 117 is configured to slide axially (parallel to B-B) along posts 115a and 115b between an engaged position and a disengaged position. The springs 119a and 119b urge the retainer 117 upward towards the teeth of the spool. The teeth of the retainer are configured to engage the teeth of the spool when the notches 116c1 on the lower flange 116c of the spool mate with protrusions 113 of the base 112. When such alignment occurs, the retainer 117 can engage the teeth 136 of the spool 116, as shown in FIG. 18. In an engaged configuration, the teeth 126 of the retainer 117 are coupled to the teeth 136 of the spool 116, the retainer 117 is coupled to the posts 115a, and the spool 116 is rotationally locked and cannot rotate relative to the housing 110 about axis B-B.

Figure 19:
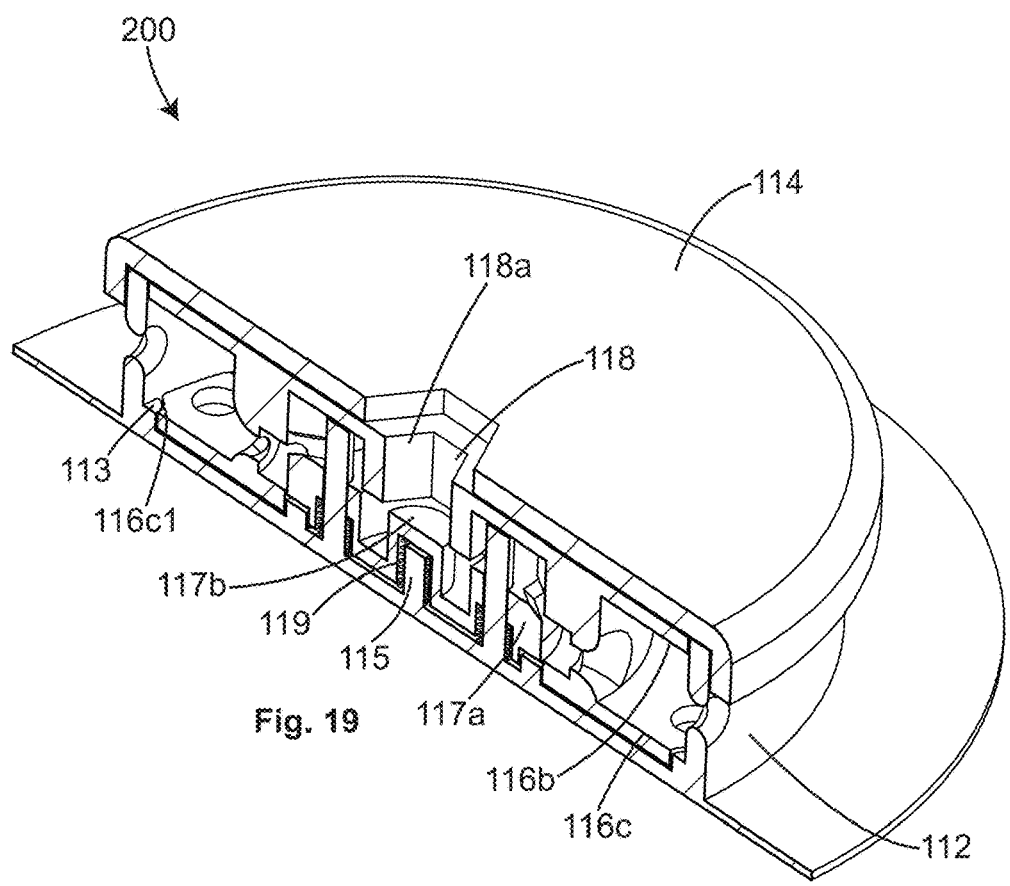
FIG. 19 is a view of the device of FIG. 14 along line 18-18 when the retainer is in a second disengaged position with the spool.

Upon insertion of a tool, such as tool 130, into the bore 118a of the socket 118, the retainer 117 can be translated along axis B-B down and out of engagement with the teeth 136 of the spool 116, as shown in FIG. 19. Once the teeth 126 of the retainer 117 are disengaged from the teeth 136 of the spool 116, the spool 116 can be rotated in either rotational direction about axis B-B, and perpendicular to the base of the housing, by applying a rotational force to the tool.

The spool 116 has a lower flange 116c having a plurality of notches 116c1. Twenty notches 116c1 are shown in the example embodiment that are spaced equally 18 degrees apart; thus, the spool 116 can be rotated in increments of 18 degrees. As such, the spool has defined stops that incrementally limit the smallest degree by which it can be rotated before the tool can be removed. Different increments can be similarly implemented by changing the rotational spacing of the notches 116c1. Alternatively, the stops can be eliminated from the device.

Figure 20:
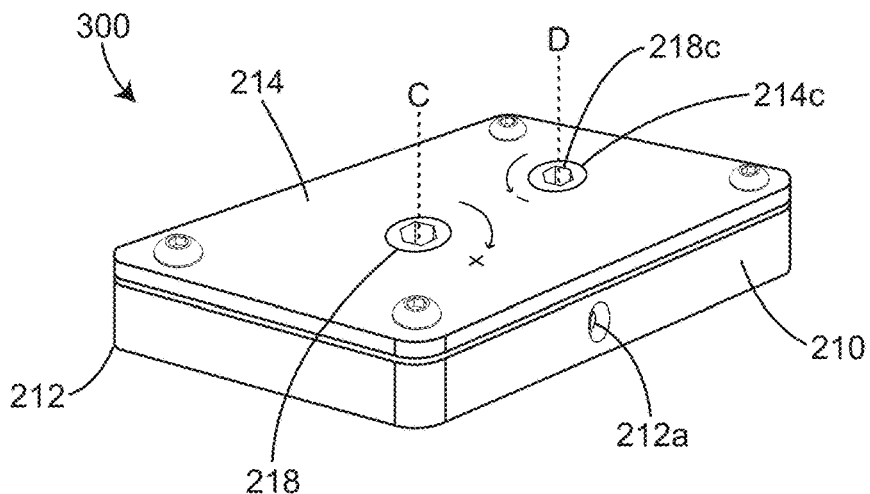
FIG. 20 is a top and side perspective view of another embodiment of an adjustment device.
Figure 21:
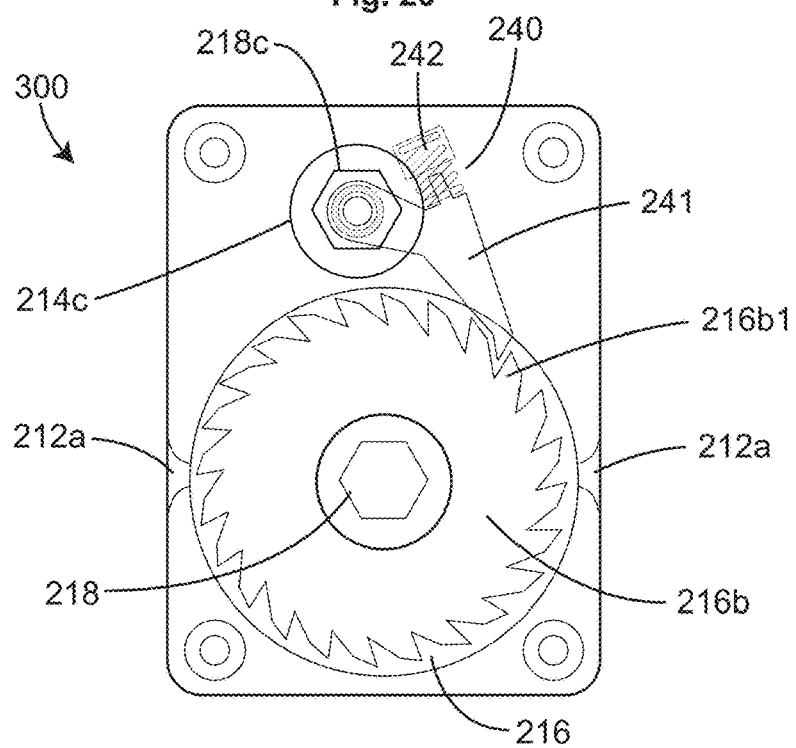
FIG. 21 is a top view of the adjustment device of FIG. 20 with the cover shown as being transparent to show details within the housing.
Figure 22:
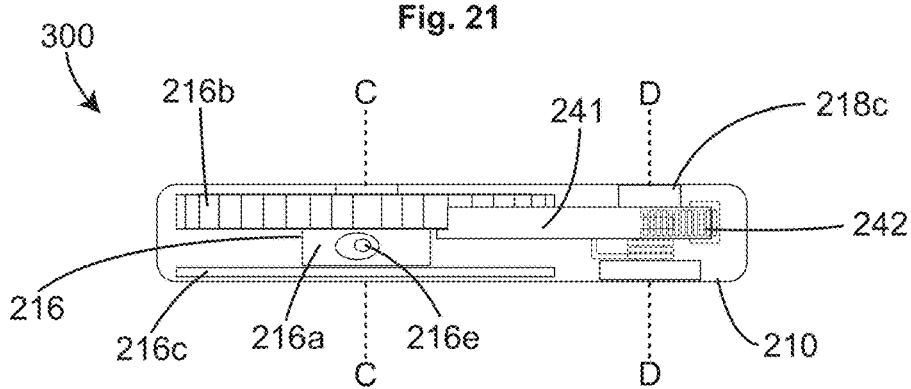
FIG. 22 is a side elevation view of the device of FIG. 20 with the cover shown as being transparent to show details within the housing.
Figure 21A:
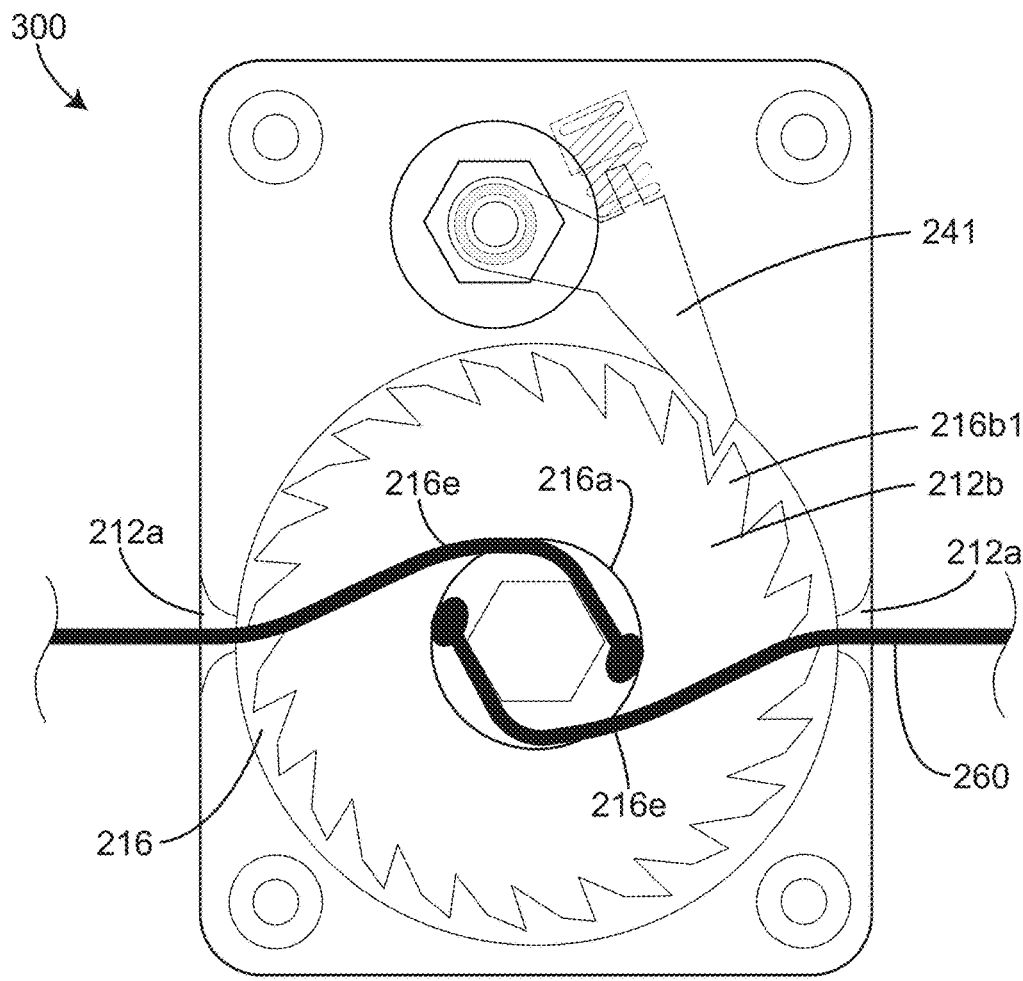
FIG. 21A shows the device in FIG. 21 connected to a flexible elongate tension line forming a fit system or tension line system in accordance with an aspect of the disclosure.
Figure 22A:
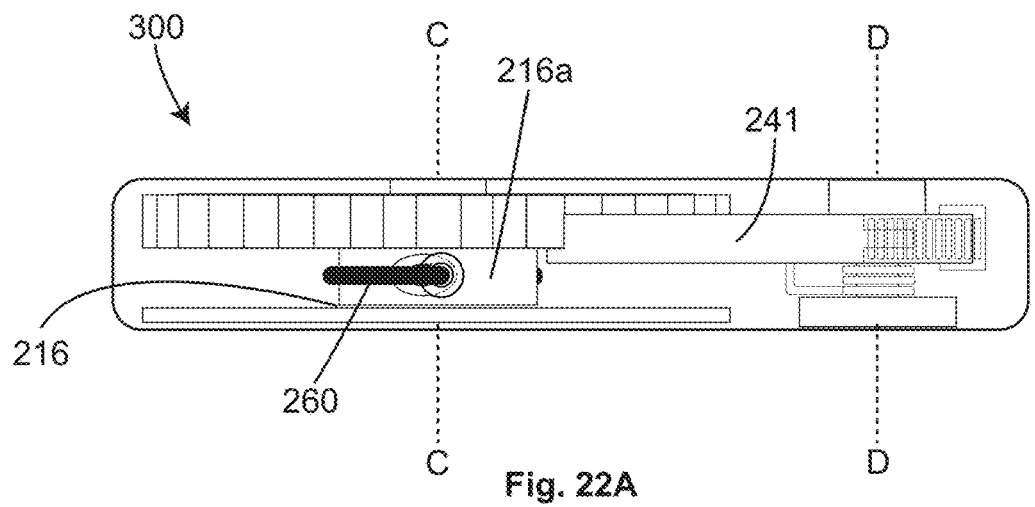
FIG. 22A shows the device in FIG. 22 with the tension line in FIG. 21A.

FIGS. 20 to 22 show details of a third embodiment of a tool operated adjustment device 300. In FIGS. 20 to 22, elements corresponding to those of device 200 are incremented by 100. The device 300 includes the same structure as the device 200 with the following exceptions. The device 300 includes a spool 216 with an upper flange 216b that has sloped gear teeth 216b1 along its outer perimeter. The spool 216 has an axle 216a that extends along axis C-C. The spool 216 is configured to rotate about axis C-C. Also, the device 300 includes a housing 210 with a cover 214 that defines an opening 214a that leads to a tool socket 218 for receiving a tool for winding the spool 216. As shown in FIGS. 21A and 22A, the spool 216 has diametrically opposed holes 216e to connect to tension line 260 routed through openings 212a in the base 212 of the housing 210. The device 300, however, does not include a retainer, like retainer 117, to rotationally lock the spool relative to the housing.

Instead, the device 300 includes a ratcheting pawl mechanism 240 that is housed in the housing 210 and is pivotally coupled to the housing about an axis D-D, which is spaced from axis C-C of the axle 216a. The mechanism 240 is operably configurable between a first configuration in which the mechanism 240 permits one way rotation of the spool 216 in a first direction (clockwise in FIG. 21) and blocks rotation of the spool 216 in a second direction (counterclockwise in FIG. 21), and a second configuration in which the mechanism 240 permits the spool 216 to rotate freely in both the first and second directions. The ratcheting pawl mechanism 240 is thus capable of maintaining tension in the tension line 260 when the tool is withdrawn from the socket 218.

The ratcheting pawl mechanism 240 includes a pawl 241 pivotally coupled to and supported by the housing 210. The pawl 241 is resiliently biased (i.e., with a spring 242) in an engagement configuration in which the pawl 241 is engaged with the teeth 216b1 of the gear 216b to permit rotation of the gear 216b, and thus the entire spool 216, in the first rotational direction (clockwise in FIG. 21), while preventing rotation of the spool 216 in the second rotational direction (counterclockwise in FIG. 21).

The pawl 241 is connected to a socket 218c that is accessible through an aligned hole 214c in the cover 214 of the housing 210. The socket 218c is configured to receive a tool, which is preferably the same tool used in socket 218. The socket 218c is rotationally fixed to the pawl 241 so that rotation of the socket 218c using the tool can cause corresponding rotation of the pawl 241 about its axis of rotation D-D. In the example shown in FIG. 21, a user wishing to disengage the pawl 241 from the gear 216b, such as for reducing tension in a tension line wound around an axle 216a of the spool 216, can insert a tool into the second socket 218c and rotate the tool counterclockwise in FIG. 21. Once the pawl 241 is disengaged, either the inherent tension in the tension line 260 will cause extension of the tension line 260 to reduce tension and rotated the spool 216 in the second direction, or the user can use a second tool in the socket 218 to rotate the spool 216 in the second direction. The user can choose to loosen the tension line 260 by turning the tool in the second socket 218c in the counterclockwise direction briefly then can turn the tool back in the clockwise direction to re-engage the pawl 241 with the teeth 216b1 for partial or incremental release. Alternatively, the user can turn the tool in the counterclockwise direction and leave it turned away until tension is fully released.

Turning now to FIGS. 23A-23C, another embodiment of a tool operated adjustment device 2000 is shown. The device 2000 includes a housing with a spool 2016 having an axle 2016a, as well as a spring-biased pawl 2041, as previously described with respect to device 300. Distinctions in adjustment device 2000 from device 300 include the following. The device 2000 includes a drive gear 2070 mounted on a parallel axle 2074 to axle 2016a, and the spool 2016 is rotationally fixed relative to a driven gear 2072 meshing with the drive gear 2070. The drive gear 2070 includes a control port 2018 for receiving the tool. When the pawl is released (discussed below) and the tool is rotated, the drive gear drives rotation of the driven gear and the spool.

In this exemplar embodiment shown, the drive gear 2070 has twice as many gear teeth as the driven gear such that the drive gear can drive the rotation of the spool in a 2:1 ratio. Any other suitable ratio can be provided between the gears. Alternatively, the drive gear 2070 can have fewer teeth to provide gear reduction and resulting finer adjustment of the driven gear. Such gear transmissions described in this embodiment are intended for application within any of the device within the scope of adjustment devices described herein.

In addition, in distinction from adjustment device 300, the spring-biased pawl of device 2000 engages the drive gear 2070. The pawl 2041 is manually releasable by rotating a portion of the pawl or knob 2076 connected thereto extending through the upper end of the cover 2014 such that only a single tool is required to operate the device. Such pawl release mechanism may be similarly used in association with device 300. The pawl 2041 is operably configurable between a first configuration in which the mechanism permits one way rotation of the spool 2016 in a first direction and blocks rotation of the spool 2016 in a second direction, a second configuration in which the mechanism permits one way rotation of the spool 2016 in the opposite direction as the first configuration and blocks rotation of the spool 2016 in the opposite direction as the first configuration, and a third configuration in which the mechanism permits the spool 2016 to rotate freely in both the first and second directions.

Figure 24A:
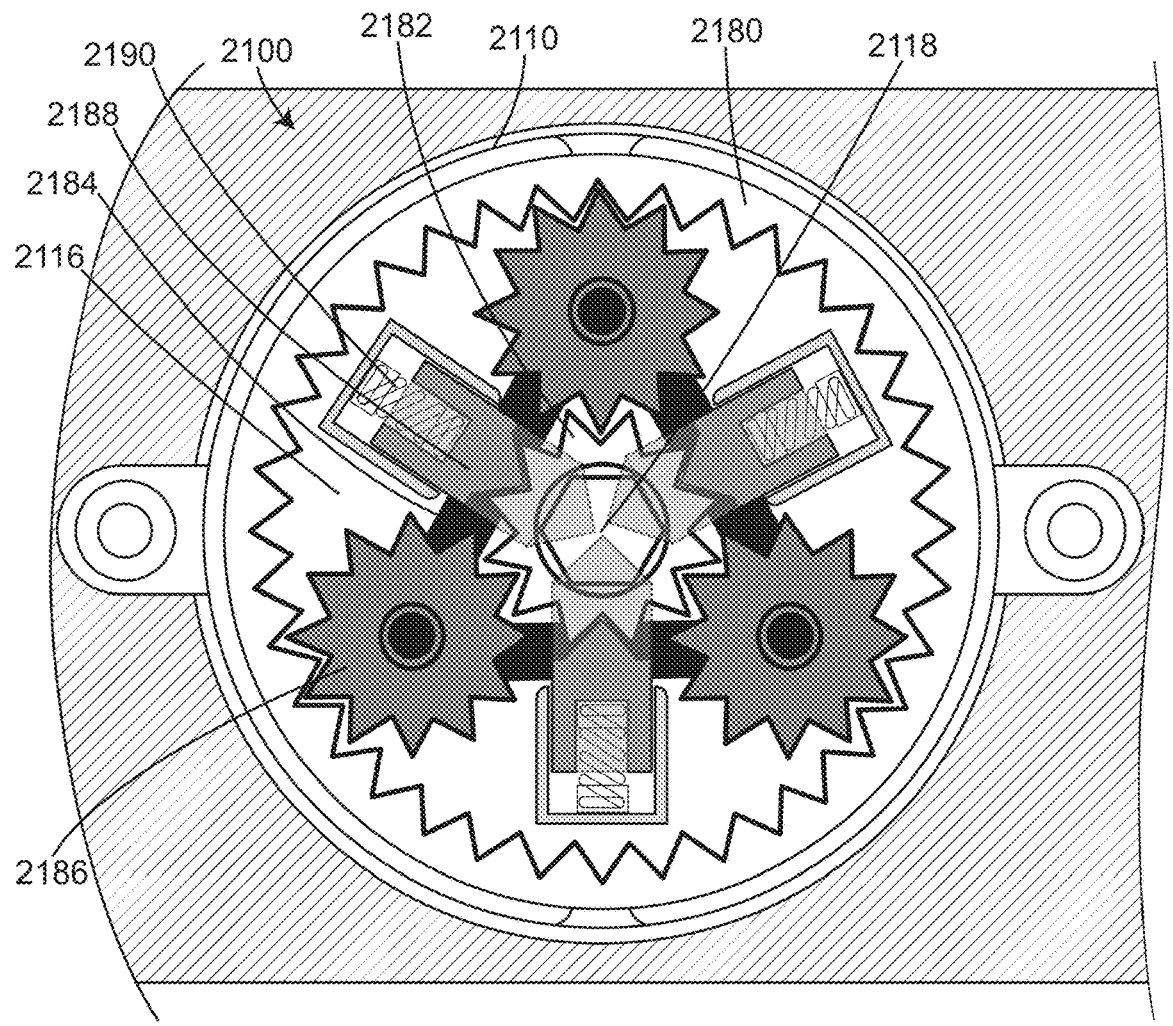
FIG. 24A is a schematic transparent top view of a top view of another embodiment of an adjustment device, shown attached to an article.
Figure 24B:
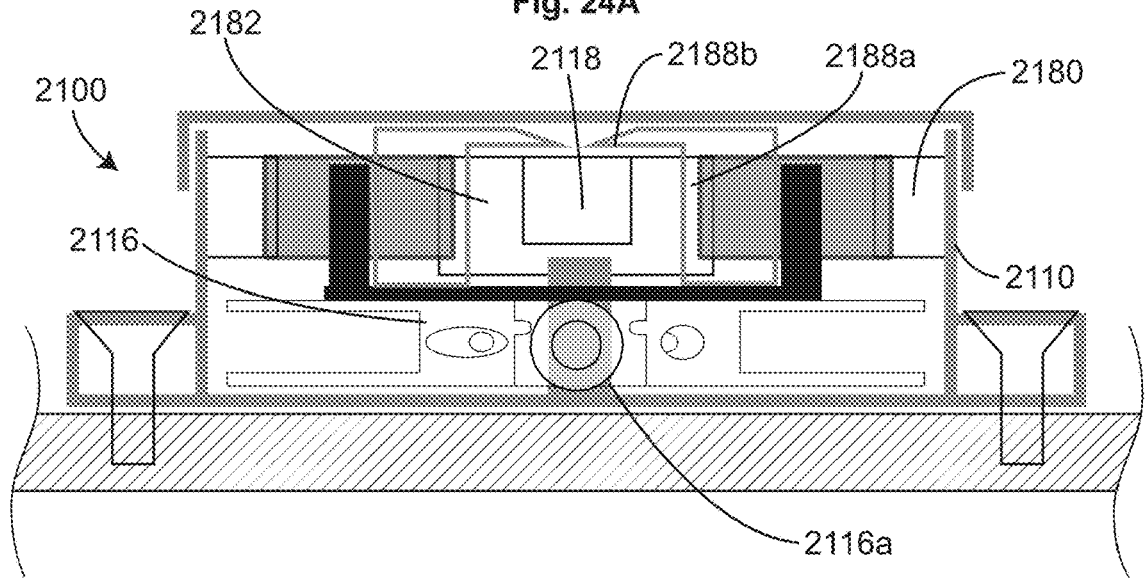
FIG. 24B is a diametric cross section view through the adjustment device of FIG. 24A, shown attached to an article.

Referring now to FIGS. 24A and 24B, another embodiment of a tool operated adjustment device 2100 is shown. The device 2100 includes a housing 2110 with a spool 2116 provided with an axle 2116a. The housing 2110 includes an interior ring of gear teeth 2180. A central star gear 2182 is coaxially situated over the spool 2116. A central control port 2118 is provided in the upper end of the housing 2110 and into the star gear 2182. A carrier plate 2184 is rotationally coupled with the spool 2116. A set of three planet gears 2186 are rotatably mounted on pins on the carrier plate 2184 in an equidistantly spaced relationship. The planet gears 2186 are engaged with the gear teeth 2180 of the housing and the star gear 2182. Three pawls 2188 are radially arranged on the retainer plate 2184 between the planetary gears 2186 and include a first portion 2188a for engagement with the star gear 2182 and second portion 2188b defining a camming ramp that extends within the control port 2118. The pawls 2188 are provided with a compression spring 2190 to bias the first portion 2188a to interfere with the star gear 2182 and prevent rotation of the planetary gears 2186 when no tool is present in the control port 2118. When the tool is inserted into the control port 2118, the tool forces against the camming ramps 2188b of the pawls to displace the second portion of the pawls away out of interference with the star gear 2182 so that the planetary gears 2186 can rotate and allow the spool 2116 to wind within the housing 2114. The planetary gear system provides mechanical advantage to the system. The planetary gear system described in this embodiment is intended for application within any device within the scope of adjustment devices described herein.

FIGS. 25 to 31 shows details of a fourth embodiment of a tool operated adjustment device 400. The adjustment device 400 is configured for use with a tension line strap (not shown). The device 400 includes a generally cylindrical housing 410 that extends along a central longitudinal axis E-E from a first base end 410a to a second upper end 410b.

The housing 410 defines two diametrically opposite elongated tension line slots 412 through which tension line straps can extend into and out of the housing 410.

Figure 30:
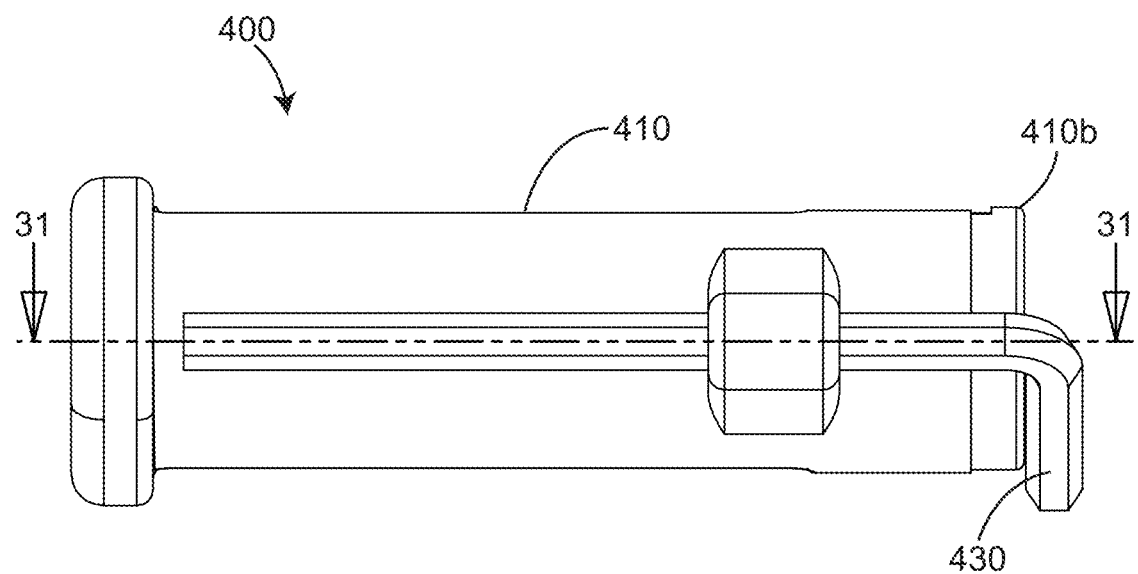
FIG. 30 is a side elevation view of the device of FIGS. 25 and 26 with a release button shows pushed in a release position.

A tool socket 414 is located at a first end 410*a* of the housing for rotating a spool 424 (FIGS. 28 and 29) (aligned with the slots 412) housed inside the housing 410. The first end 410*a* of the housing 410 is connected to a retaining ring with a threaded connection. The retaining ring 413 retains the tool socket element 414 at the first end 410*a* of the housing 410. A release button 416 is located at the second end 410*b* of the housing 410 that is opposite the first end 410*a* of the housing 410. The button 416 is configured to translate axially relative to the housing 410 along axis E-E, but the button 416 cannot rotate relative to the housing 410 due to the interlocking shape of the button 416 and the hole in the second end 410*b* of the housing 410 that the button 416 extends through. The release button 416 is biased outwardly with respect to the second end 410*b* of the housing 410. A cover 418 is pivotally connected to the second end 410*b* of the housing 410 and is configured to rotate about axis E-E parallel to central longitudinal axis E-E. When the button is not in use, the cover can be rotated over the button to conceal and protect the button from inadvertent actuation. When the button 416 is to be used, the cover 418 can be rotated about axis E-E to reveal the button, as shown in FIGS. 24 and 30.

The body 410 includes a tool holder 420 that extends from an elongate outer side of the housing 410. The tool holder 420 retains a tool 422 that is receivable in the tool socket 414. The tool 422 shown is a hex key.

Figure 26:
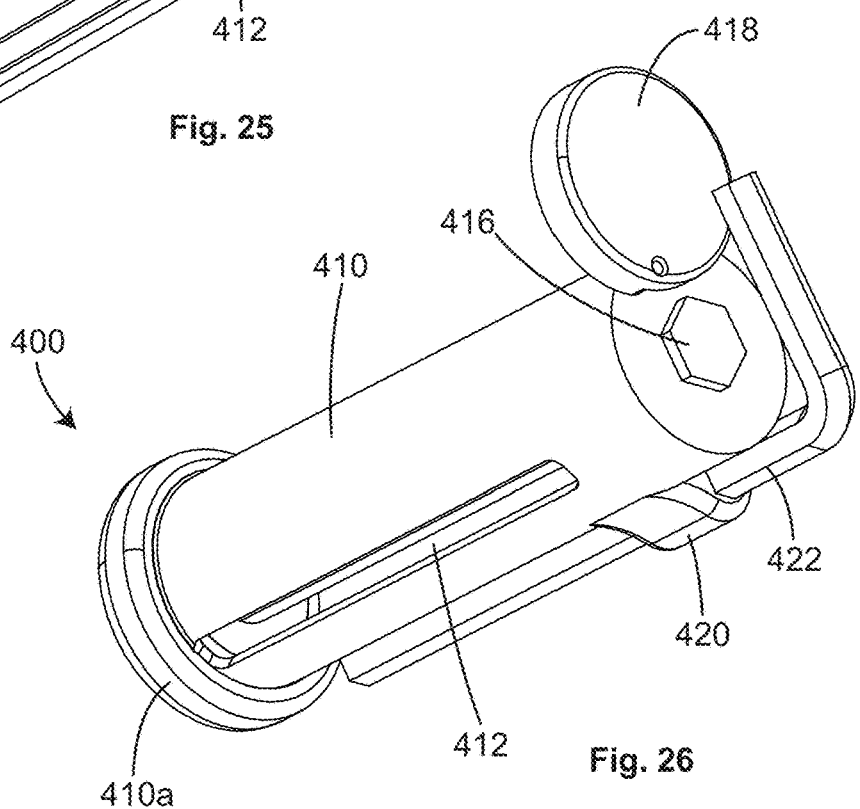
FIG. 26 is a rear, bottom, and side perspective view of the adjustment device of FIG. 25.
Figure 27:
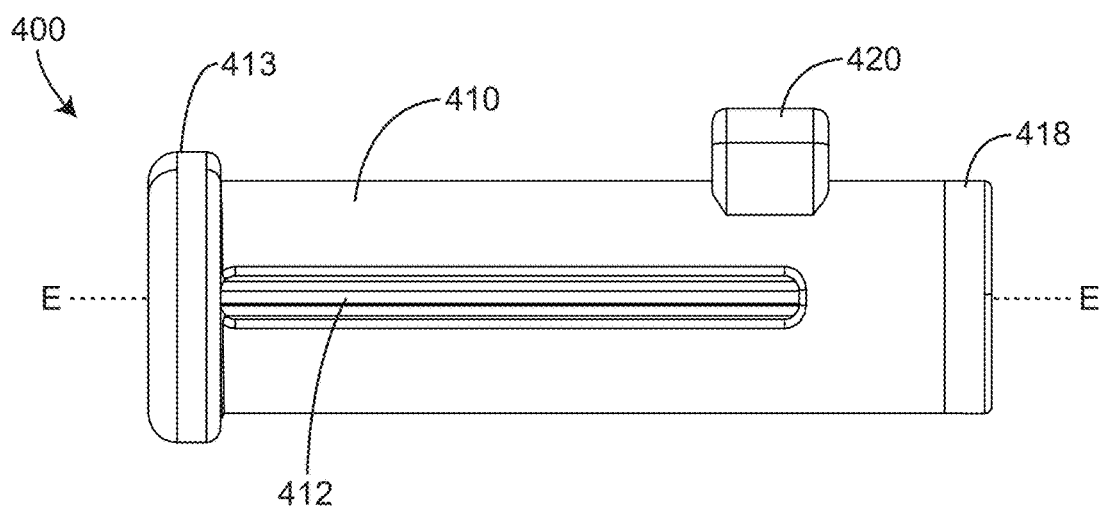
FIG. 27 is a side elevation view of the device of FIG. 26.

FIGS. 26, 27, and 29 show additional details of the spool 424 and ratcheting release mechanism 426 housed inside the housing 410. The spool 424 includes a first flange 415, a second flange 417, and two elongated members 419 rigidly connected at their ends to the first and second flanges 415, 417. The tool socket 414 is rotationally fixed to the first flange 415 of the spool 424. In the embodiment, the first flange 415 is integrally formed with the tool socket 414, though this is not a requirement. The flanges 415 and 417 connect to the elongated members 419 so that there is an elongated gap 419*a* between the elongated members to receive and retain a tension line strap. The elongated members 419 have an overall oval profile for at least the same reasons as the oval profile of the axle 16*a* of device 100 described herein. The entire spool 424 is configured to rotated in unison about axis E-E.

The second flange 417 of the spool is configured to connect to the ratcheting release mechanism 426. Specifically, notches 417*a* are formed along a peripheral edge of the second flange 417. The notches are configured to engage pins 421 that rotationally couple the second flange 417 to the ratcheting release mechanism 426 as described in greater detail below.

Figure 25:
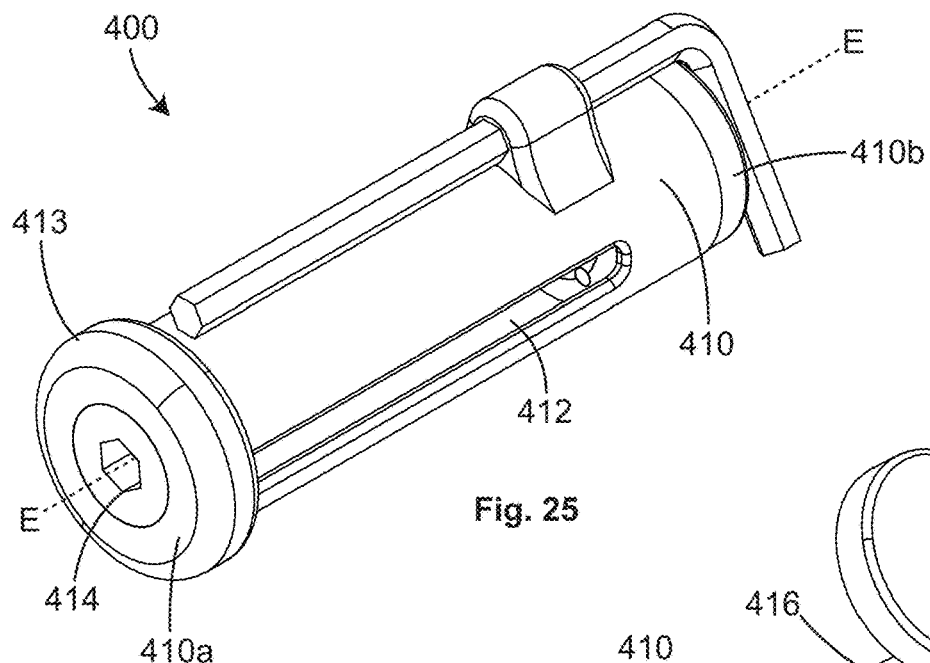
FIG. 25 is a front, top, and side perspective view of another embodiment of an adjustment device.

The ratcheting release mechanism 426 includes a shaft coupler 423, a ratcheting disc 425, the release button 416, a spring 427, and a spring retainer 429. The shaft coupler 423 is an annular member having an inner cylindrical surface defining an interior space and an outer cylindrical surface that is configured to rotate in unison with the spool 424 about inner surface of the housing 410. As shown in greater detail in FIG. 31, the second flange 417 of the spool 424 is received and seated in an inner side (relative to central axis F-F) of the interior space of the shaft coupler 423. The second flange 417 is pivotally fixed to the shaft coupler 423 with the pins 421 so that the entire spool 424 and shaft coupler 423 rotate about axis E-E in unison (FIGS. 25 and 27).

The spring 427, spring retainer 429, and ratcheting disc 425 are also disposed in the interior space of the coupler 423. The spring 427 is positioned between the second flange 417 of the spool 424 and the spring retainer 429. The ratchet disc 425 is positioned between the spring retainer 429 and the push button 416. The push button has pins 416*a* that extend through the ratchet disc 425 and spring retainer 429 to rotationally fix them all to one another so they all remain rotationally fixed together and thus remain rotationally fixed relative to the housing 410 due to the fact that the button 416 is rotationally fixed relative to the housing 410.

Figure 31:
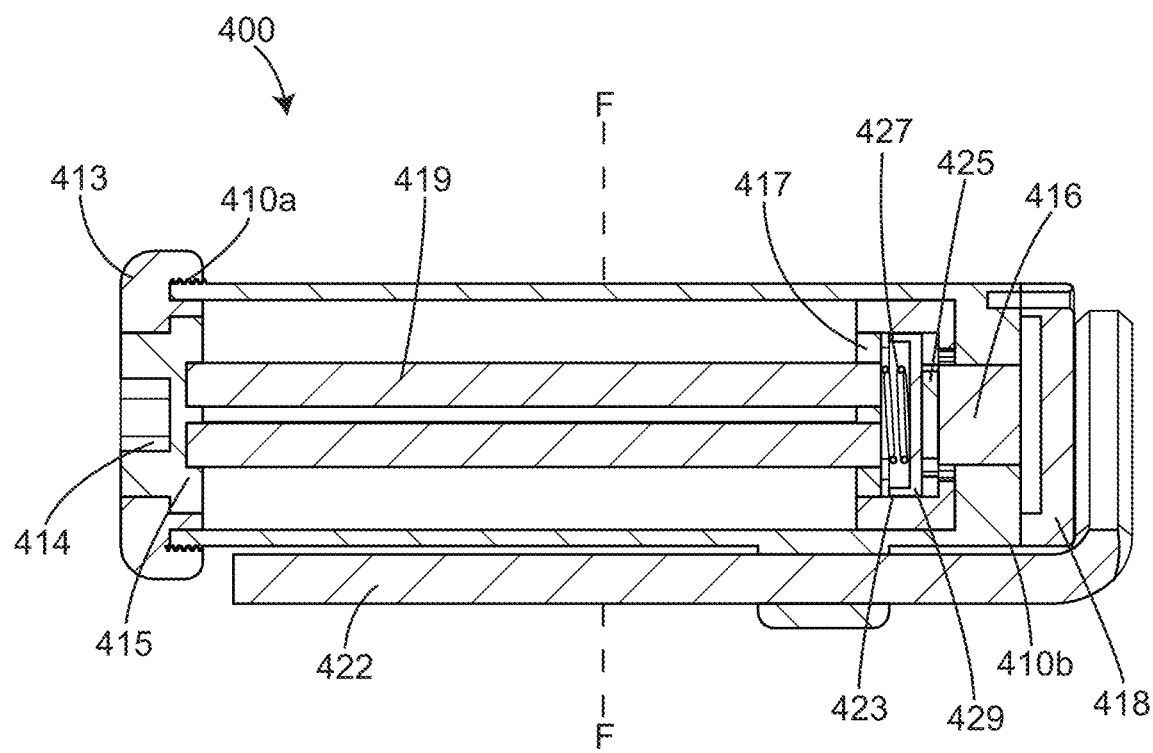
FIG. 31 shows a view of the device of FIGS. 25 and 26 along line 31-31 in FIG. 30.
Figure 32:
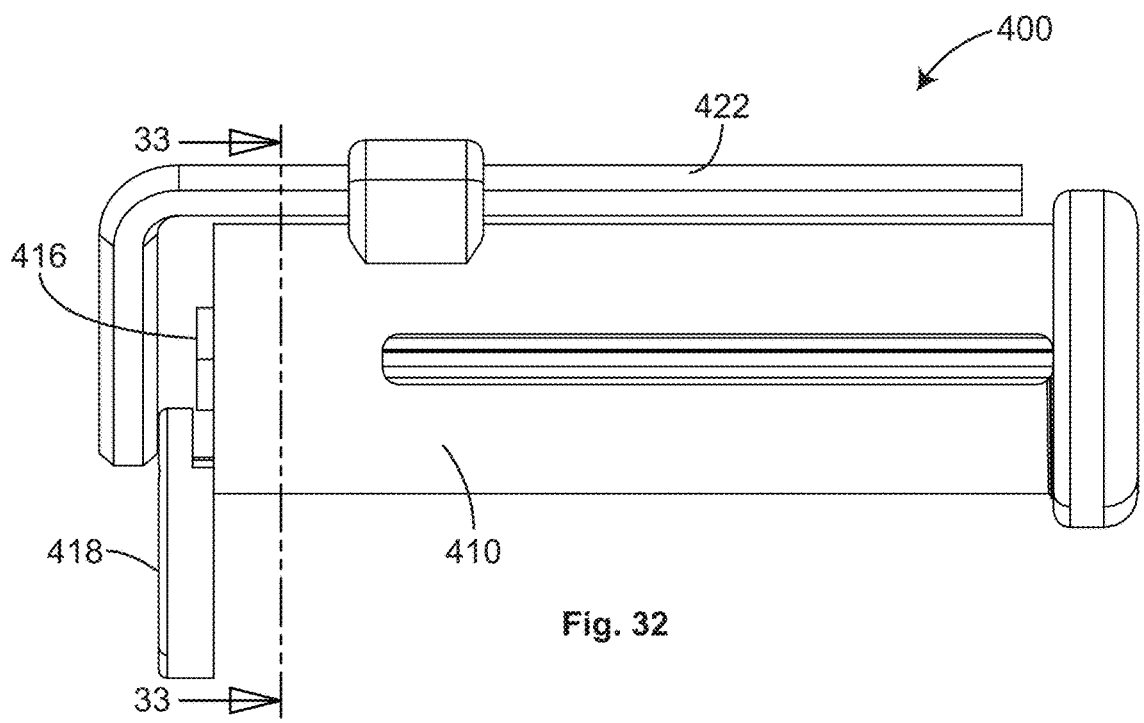
FIG. 32 is a side elevation view of the device of FIGS. 25 and 26 with the release button shown in an extended, unreleased position.
Figure 33:
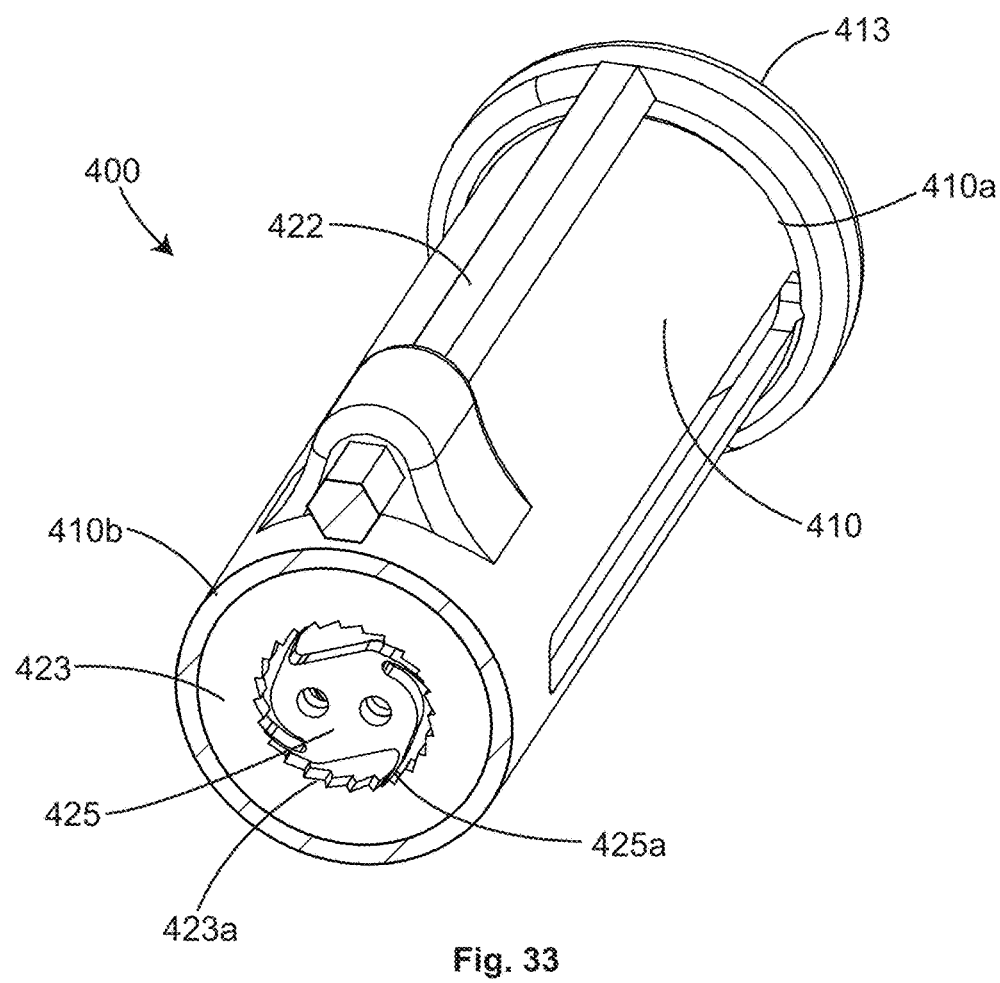
FIG. 33 is a perspective view of the device of FIGS. 25 and 26, having a section taken along line 33-33 in FIG. 32 to show ratchet disk engaged with inner teeth of a shaft coupler.

The ratchet disc 425, spring retainer 429, and push button 416 are configured to translate along axis E-E within the interior space of the shaft coupler 423. The spring 427 biases the ratchet disc 425, spring retainer 429, and push button 416 outward (relative to axis F-F). The inner cylindrical surface of the outer side (relative to the axis F-F) of the coupler 423 has inner teeth 423*a* that are configured to engage ratchet pawls 425*a* of the ratchet disc 425 when the push button 416 is in a first configuration in which the button extends outward from the second end 410*b* of the housing 410, as shown in FIGS. 32 and 33. FIG. 33 shows ratchet disc 425 engaged with the inner teeth 423*a* of the shaft coupler 423. When the button 416 is pressed inward toward axis F-F, as shown in FIGS. 30 and 31, the ratchet disc 425 is translated inwardly against the bias of the spring 427 (which is compressed), which disengages the ratchet pawls 425*a* from the inner teeth 423*a* of the shaft coupler 423. When the pawls 425*a* of the ratchet disc 425 are disengaged from the inner teeth 423*a*, the user can rotate the spool 424 in either the first or the second direction about the axis E-E directly using the tool 422 in the tool socket 414. Also, if tension has been built up in a tension line connected to the spool 424, pressing on the release button 416 will cause the spool 424 to unwind in the second rotational direction about axis E-E to reduce tension in the tension line.

The pawls 425*a* of the ratchet disc 425, when engaged with the inner teeth 423*a* of the coupler 423, permit the spool 424 to rotate in a first rotational direction about axis E-E when the socket 414 is rotated using the tool 422, while preventing the spool 424 from rotating in a second rotational direction opposite the first direction. When the tool is released or withdrawn from the tool socket 414, the pawls 425*a* retain tension in the tension line. The tension can be released by disengaging the pawls 425*a* from the inner teeth 423*a* of the shaft coupler 423 by pushing on the release button 416.

Turning now to FIGS. 34A-34C, a modification to the fourth embodiment is provided which facilitates collecting tension line at the exterior of the housing; i.e., to effectively make the housing of the adjustment device into a secondary spool. (The inner ratcheting assembly is the same as in adjustment device 400 and will not be further described here.) The modification adjustment device 400' includes the following. As shown in FIGS. 34A-C, the adjustment device 400' bolts together, defining lateral bosses 460' on diametrically opposing sides of the housing 410'. Gear teeth 462' are provided fixed to one end of the exterior of the housing 410'. A removable cap 464' is provided that covers and exposes the gear teeth 462'.

Figure 34D:
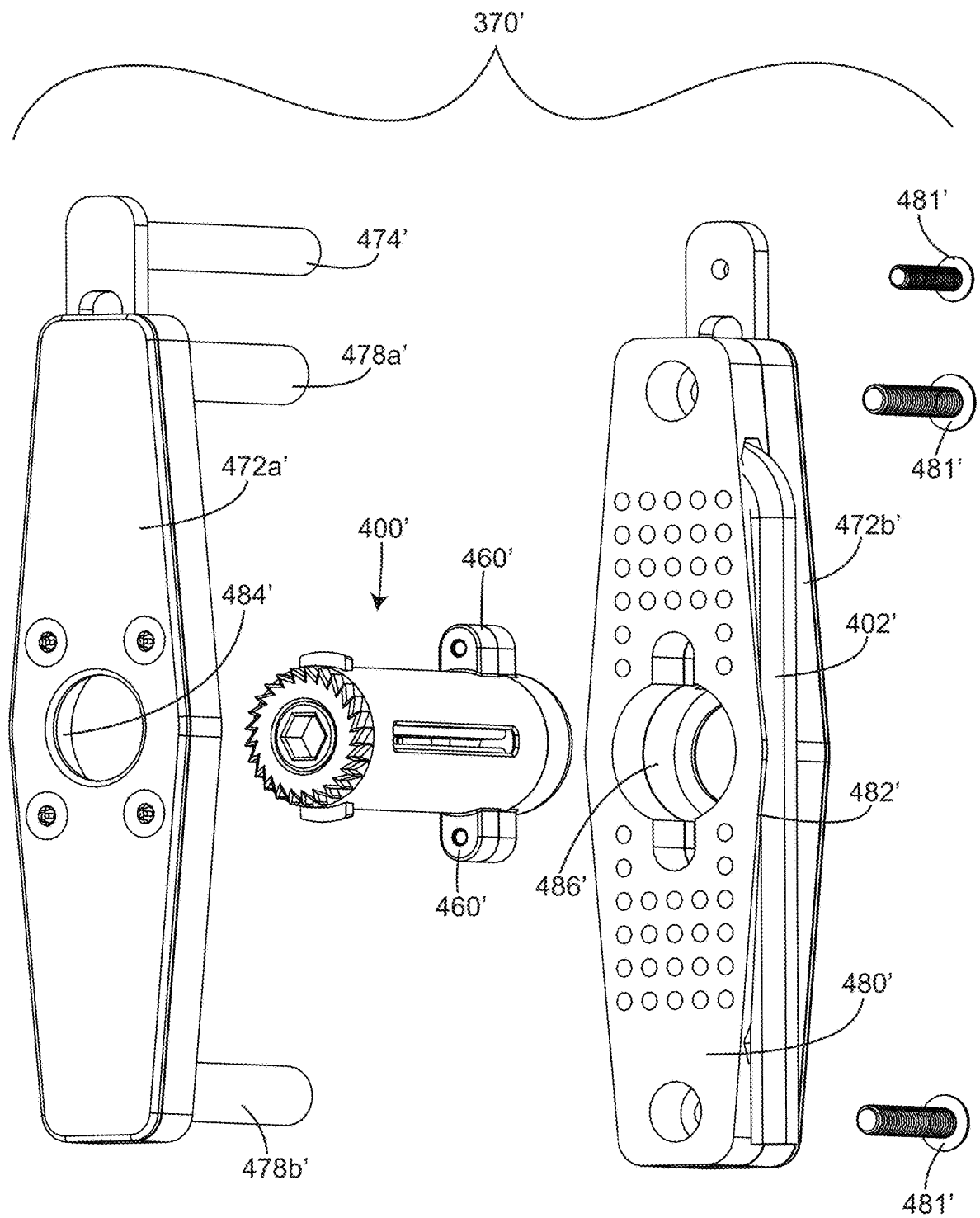
FIG. 34D is an assembly view of the adjustment device of FIG. 34A with a supplemental ratcheting assembly.
Figure 34F:
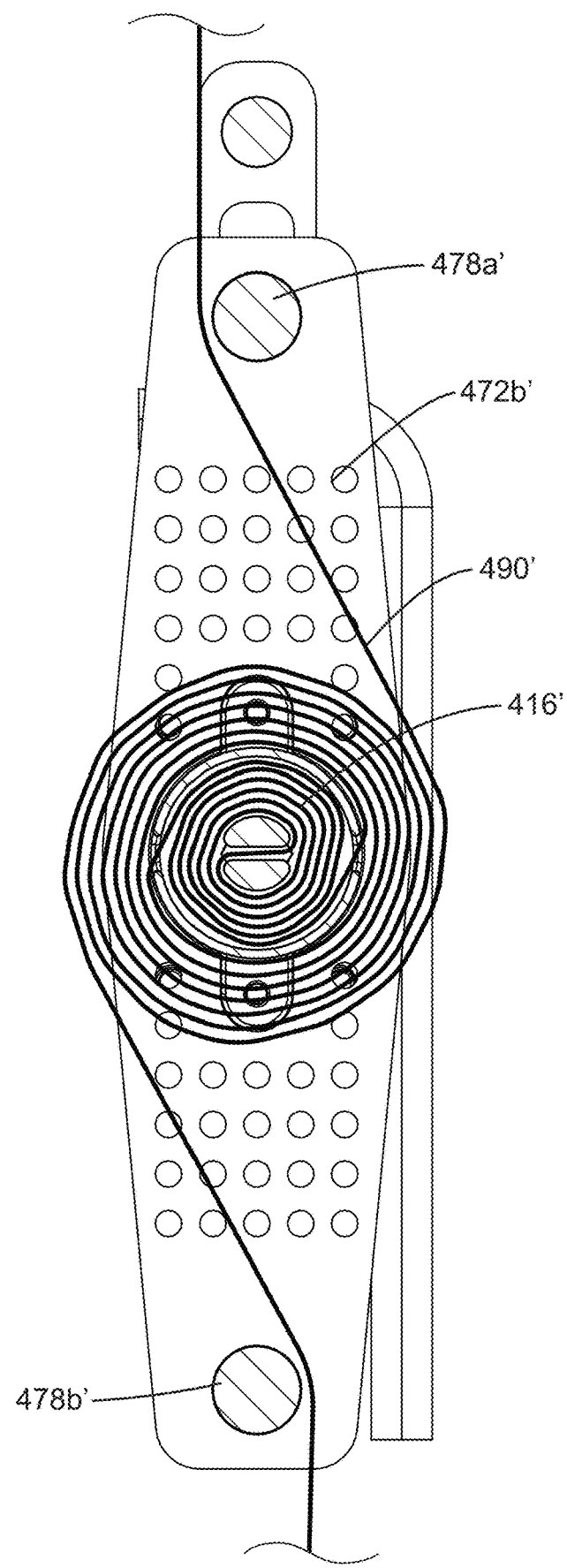
FIG. 34F is a section view through line 34F-34F in FIG. 34E and showing the adjustment device winding an elongate flexible member.
Figure 35:
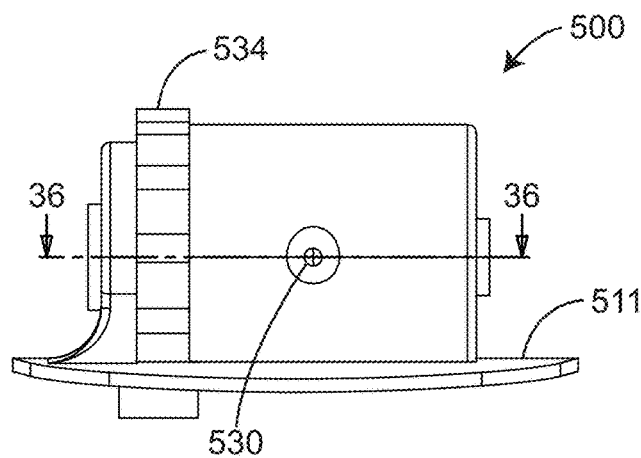
FIG. 35 is a side elevation view of another embodiment of an adjustment device.
Figure 37:
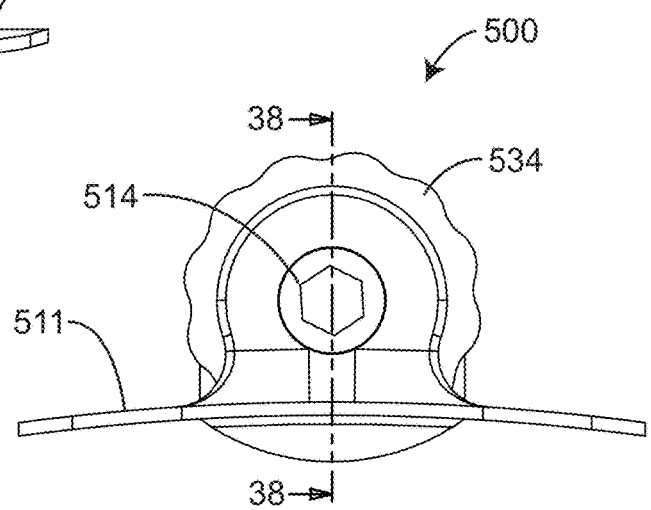
FIG. 37 is a front elevation view of the device of FIG. 35.
Figure 36:
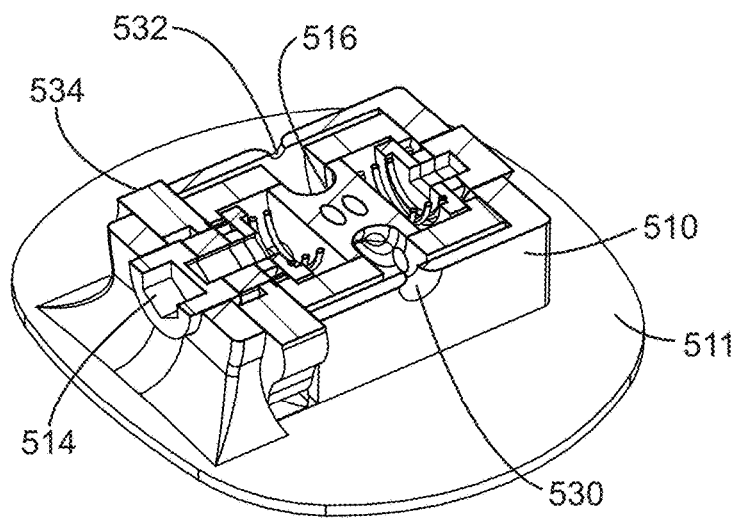
FIG. 36 is a section view of the device in FIG. 35 taken along line 36-36 in FIG. 35.
Figure 38:
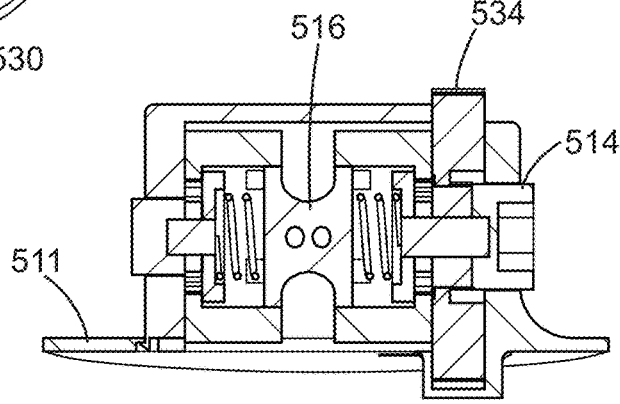
FIG. 38 is a section view of the device of FIG. 35 taken along line 38-38 in FIG. 37.

Referring to FIGS. 34D-34F, a removable outer ratcheting assembly 470' is provided for coupling with the adjustment device 400'. The ratcheting assembly 470' includes first and second ratchet plates 472*a*' and 472*b*', a release handle 474', a spring 476', first and second pivot bars 478*a*' and 478*b*', and optionally a spacer 480' with snap-fit receiver 482' for a tool 402'. The adjustment device is assembled into recesses 484', 486' within the ratchet plates 472' and spacer 480', with the bosses 460' registering in the recesses and fixing rotation of the device relative to the plates. The ratchet plates 472a', 472b' and handle 474' are assembled about the adjustment device 400' with screws 481'. The release handle 474' extends in a u-shape into ratchet plates and includes a pawl 488' at one end. The pawl 488' is biased by the spring 476' to interfere with the gear teeth 462'. Referring to FIG. 34F, while the pawl 488' is engaged, as the inner ratcheting assembly is activated with the tool 402' inserter and rotated within control port 418' (FIG. 34E), the flexible elongate member 490' is wound first about the interior spool 416'; then, once the interior spool is full, the elongate flexible member 490' is wound about the exterior of the housing. The pivot bars 478a, 478b prevent unwinding of the flexible elongate member 490'. Pulling on the release handle 474' relative to the ratchet plates 424a' and 472b releases the pawl 488' from interference with the gear teeth 462' so that the ratchet assembly can rotate relative to the adjustment device and allow unwinding of the flexible elongate member 490'.

FIGS. 35 to 38 show details of a fifth embodiment of a tool operated adjustment device 500. The device 500 has substantially corresponding structure to device 400. One difference between device 500 and device 400 lies in the fact that the spool 516 of the device 500 is constructed to wind a tension line lace or cable rather than a strap. Thus, a smaller spool 516 is utilized. In addition, the housing 510 and entry/exit ports 530, 532 are correspondingly smaller as well, and a stitch flange 511 is provided to the housing for integration of the device into an article, such as soft goods or a textile-based application.

An additional feature of device 500 includes a dial 534 rotationally fixed relative to the spool 516 and accessible from outside the housing. The dial 534 allows a user to collect slack or loose cable or lace before a tool is inserted into the control port 514. The dial 534 offers minimal mechanical advantage, but allows the user to slide a finger, palm, or other surface across the dial to collect the loose lace then use the tool to increase the tension under the mechanical advantage of the tool (and/or any gears that may be integrated into the device, as described above).

Prior art FIG. 39A illustrates that prior art tensioning device that include an integrated line tensioner are bulky devices and protrude when applied to wearable articles on the human body. The larger profile of the prior art systems 610 and 611 can concentrate an impact force on the portion of the body to which the systems 610 and 611 are attached if a user falls or is impacted in that area of the user's body. In addition, the larger size can be aesthetically displeasing or unsuitable for certain wearable applications. By way of comparison, the adjustment devices 620 shown in FIG. 39B have a lower profile. This is permitted, at least in part, because they use a separable tool rather than a line tensioner having an integrated-force applier; thus, they can be made smaller in size and better integrated with wearable articles. Further, in the event of a fall, force on the wearer is minimized as a result of the smaller size. In addition, by requiring use of a separate tool for tension and/or release, they are optimized to prevent inadvertent adjustment.

FIGS. 40-66 show various uses of adjustment devices into various exemplar articles. Such articles include wearable articles, in which the adjustment device operates to facilitate the fit of the article; sporting articles requiring application of tension, and utility articles requiring application of tension. It will be appreciated that adjustment device 620 of the systems 640 may take the form of any of the embodiments of an adjustment device described herein and is not limited to the schematics shown in FIGS. 40-66. Furthermore, it is appreciated that the fields and applications shown and briefly described herein are not intended to be exhaustive or limiting but are merely examples.

Figures 40, 41, 42:
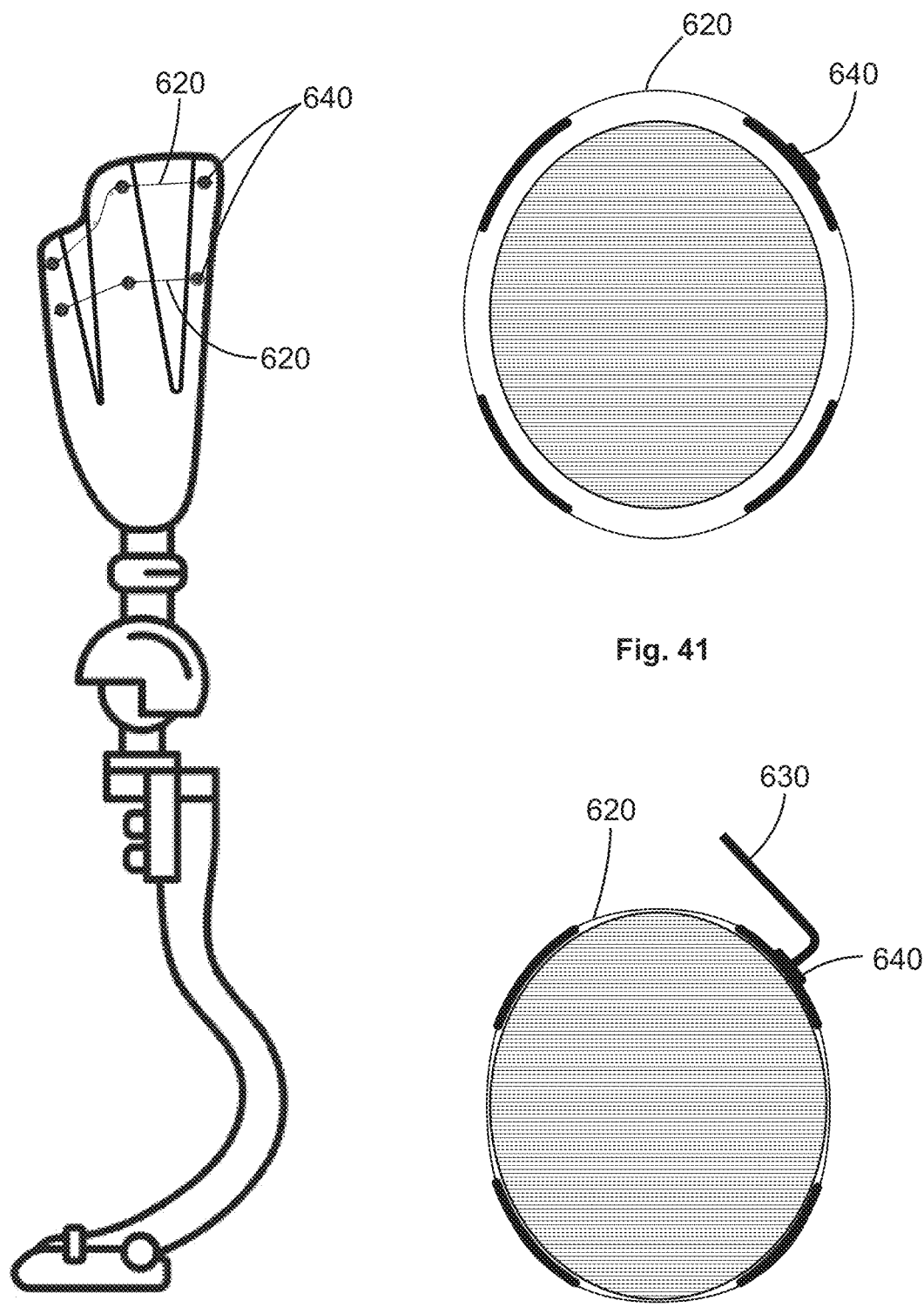
FIGS. 40-66 shows schematic representations of fit systems and line tensioning systems in accordance with the disclosure used in various fields of use.

FIGS. 40-42 shows fit systems 620 applied to a prosthetic socket 700. For the socket shown in FIGS. 40-42, an adjustment device 640 is coupled to the socket to apply or release tension on a cable 645 extending about all or a portion of a circumference of a prosthetic socket. For example, the device may be adjusted to tension the cable 645 to draw struts 648a, 648b, 648c, 648d of the socket radially inward or release tension to allow the struts to flex radially outward. Similarly, fit systems 620 could be applied to a prosthetic socket 700 to draw two sections or regions of the prosthetic socket 700 closer together or allow them to flex apart. Applying or relieving tension in the tension lines can enlarge or reduce the opening of the prosthetic or change the distribution of forces to adjust the fit of the prosthetic to a user. As shown in FIGS. 41 and 42, each system 620 shown in FIG. 40 includes one adjustment device 640 connected to the cable 645 banded about the prosthetic socket 700. As shown in FIG. 42, a tool 630 is required to adjust tension to prevent inadvertent adjustment or limit adjustment to a prosthetist.

Figure 43:
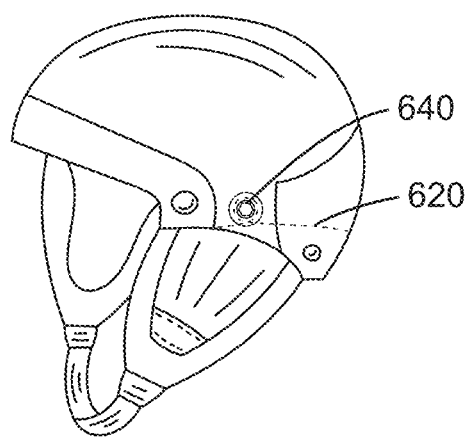

Referring to FIG. 43, the adjustment device of the fit system may be mounted to the shell of the helmet 710 or may be left free to be positioned along the strap 650b' at an intermediate position between the sides of the helmet.

Figure 44:
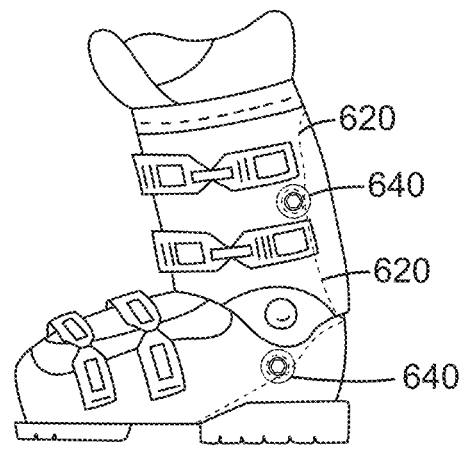
Figure 45:
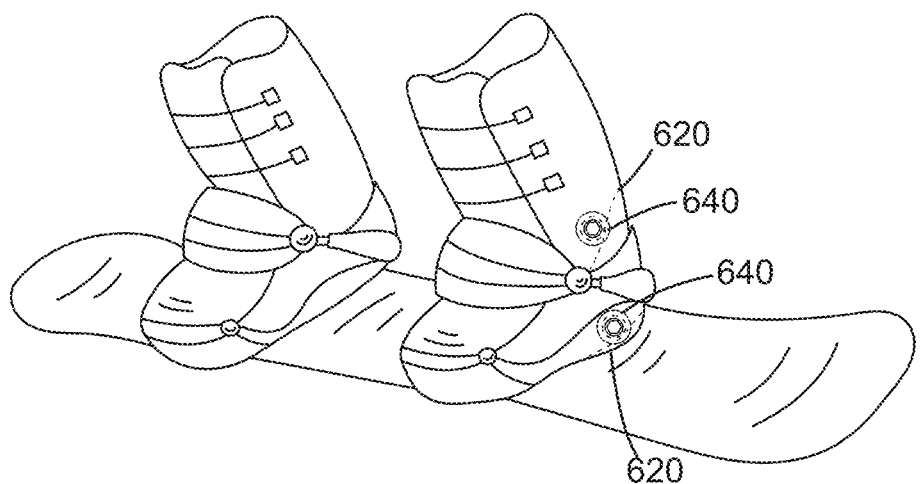
Figure 46:
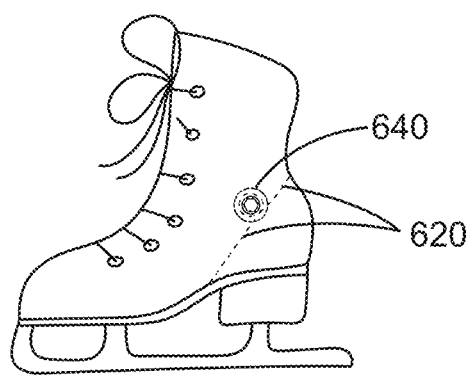

Turning to FIG. 44, multiple fit systems 620 are connected to a ski boot 720. The straps are banded around a leg portion and a foot portion of the boot and the adjustment devices of the straps may be mounted directly to the leg and foot portions of the boot. FIG. 45 shows fit systems 620 connected to snowboard boots 730. Straps of the systems 620 are banded about the leg portion of the snowboard boots with the adjustment device 640 mounted directly to the boot. Also, straps of the fit system 620 are shown connected to the snowboard and include adjustment devices 640 mounted to the snowboard straps which can be used to adjust the connection of the snowboard boots to the snowboard. FIG. 46 shows a fit system 620 connected to a skate 740, specifically an ice skate. The adjustment device 640 of the fit system 620 is mounted directly to the skate while the tension line is banded about the skate.

Figure 47:
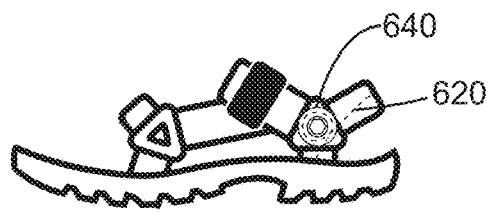
Figure 48:
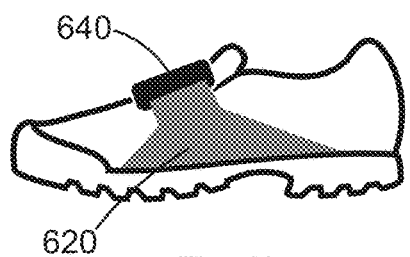
Figure 49:
Figure 50:
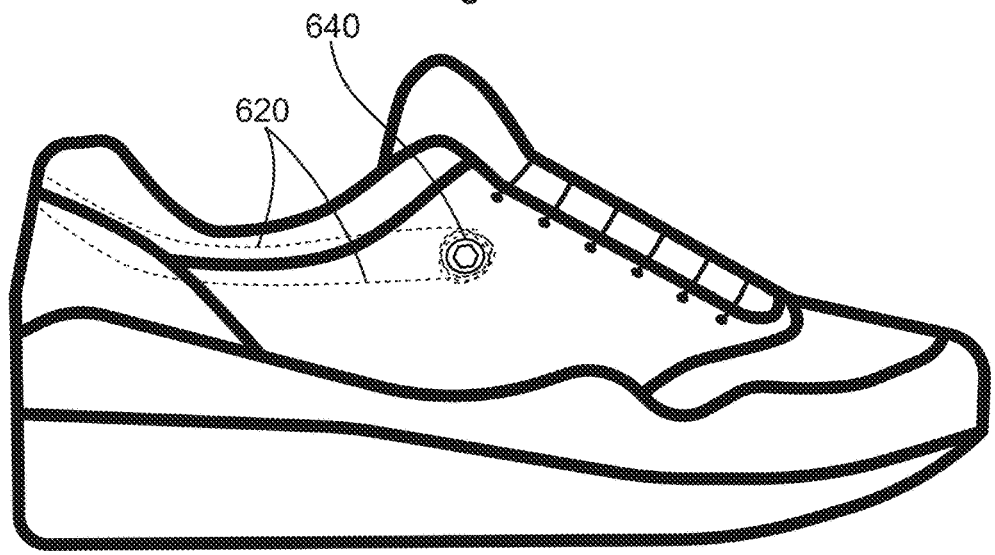

FIG. 47 shows an embodiment of a fit system 620 connected to a sandal 750. The adjustment device 640 of the fit system 620 is mounted to one of the sandal straps while the tension line takes the place of a sandal closure strap. FIG. 48 shows a fit system 620 connected to a shoe 760. The adjustment device 640 of the system 620 is mounted to the shoe and the strap extends across the tongue of the shoe. FIG. 49 shows a fit system 620 connected to a boot 770, where the fit system is arranged identically to the system shown in FIG. 46 used with a skate 740. FIG. 50 shows a fit system 620 with an adjustment device that is embedded into an upper of a shoe 780 with laces partially concealed by the upper (shown in broken lines) and laces that are visible across a tongue of the shoe.

Figure 51:
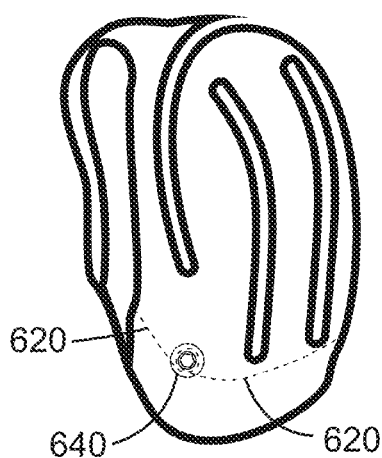
Figure 52:
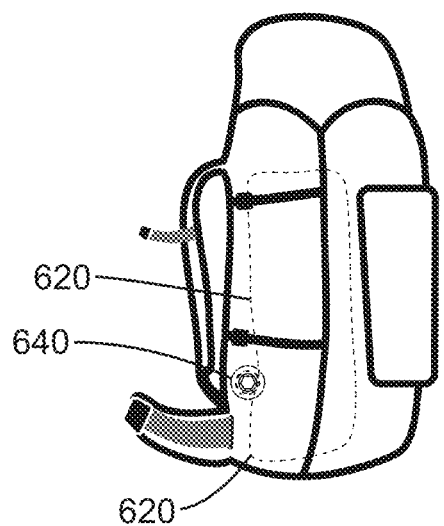

FIG. 51 shows an embodiment of a fit system 620 used for an adjustable strap of a day pack 790 application. The tension line of the system 620 is connected to the day pack and the adjustment device 640 is not directly mounted to the day pack, but is spaced therefrom. FIG. 52 shows a fit system 620 used for an adjustable strap of a bag or backpack 800 (e.g., a camping backpack). The tension line of the system 620 is connected to the backpack and the adjustment device 640 is not directly mounted to the backpack but is spaced therefrom.

Figure 53:
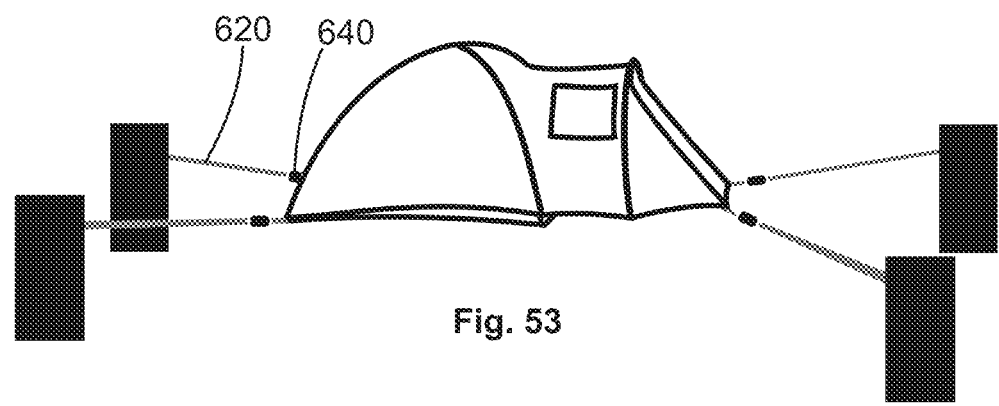
Figure 54:
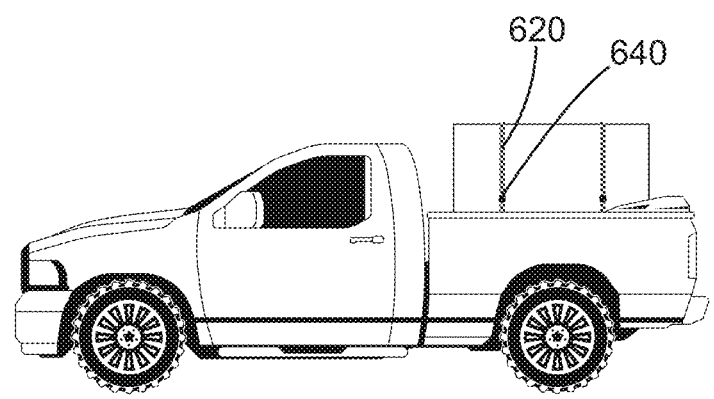

FIGS. 53 and 54 show uses of line tensioning systems 620. FIG. 53 shows fit systems 620 used as straps of a suspended tent 810. Each strap is connected to a corresponding adjustment device 640. Each strap is configured to connect at one end to a tent and an opposite end to another structure (such as a tree) to suspend the tent above the ground. The line tensioning systems 620 may also be used for other suspension applications, such as mountaineering, rock-climbing, and rappelling. Similarly, the line tensioning system 620 may be used to tension sporting nets, such as for tennis, badminton, volleyball, table tennis, etc., and may be provided with the equipment therefor. FIG. 54 shows line tensioning systems 620 used as cargo tie down straps 820 connected to a truck bed. The line tensioning systems described herein can also be used as closures in carry-alls, suitcases, duffel bags, sport bags, and thus may be incorporated into such articles in accord with the intended scope herein.

Figure 55:
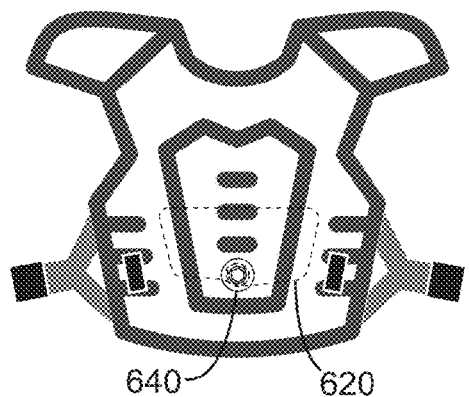
Figure 56:
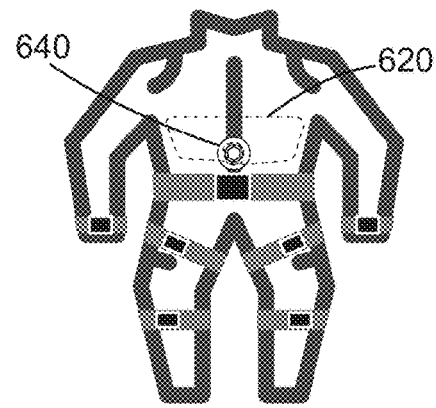
Figure 57:
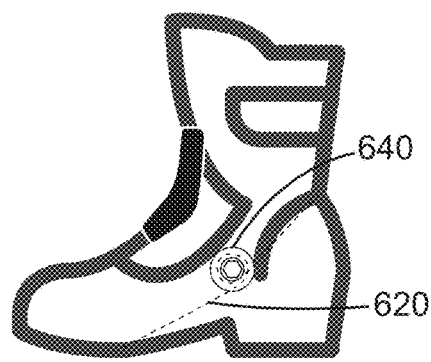
Figure 58:
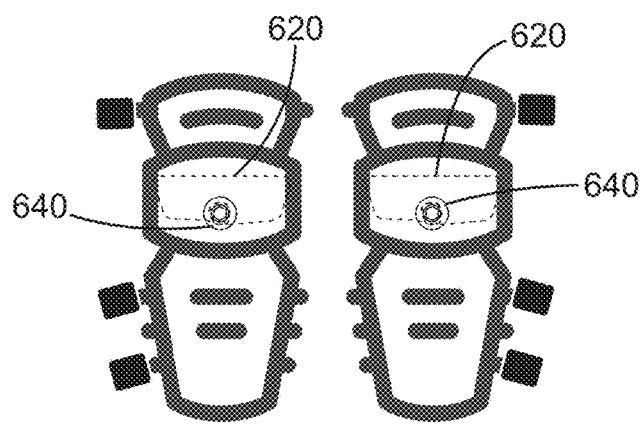
Figure 59:
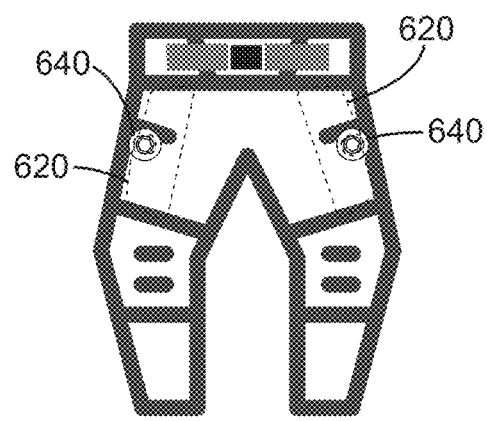

FIGS. 55-59 show fit systems 620 applied to protectable wearable articles utilized in the field of motorsports. Specifically, FIG. 55 shows fit systems 620 applied to a protective vest 900 that can be used to adjust the fit of the vest to a user. FIG. 56 shows fit systems 620 applied to a protective suit 910. The fit systems can be used to adjust the fit of the protective suit to a user's body at the locations shown in FIG. 56. FIG. 57 shows a fit system 620 applied to a motorcycle boot 920. As shown in FIG. 57, two straps are banded about the boot: one strap banded about a leg portion of the boot and one strap banded about the foot. Separate adjustment devices 640 may be provided for each strap to independently tension each strap. FIG. 58 shows fit systems 620 applied to protective knee pads 930 where the strap is configured to be banded about the knee of a user and the adjustment device 640 can be used to adjust the fit of the straps. FIG. 59 shows a fit system 620 applied to protective pants 940 for adjusting the waist of the pants to fit a waist of a user.

Figure 60:
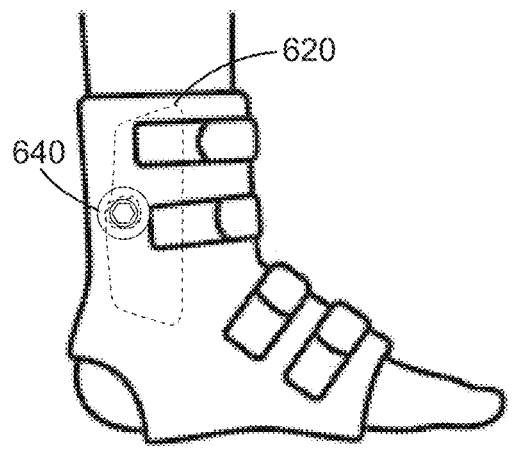
Figure 61:
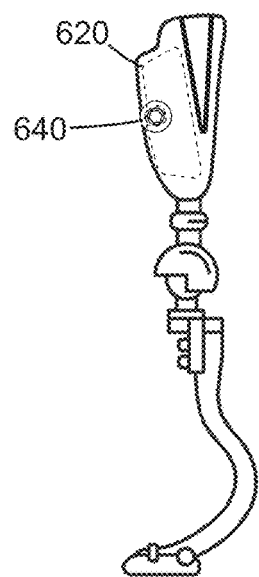
Figure 62:
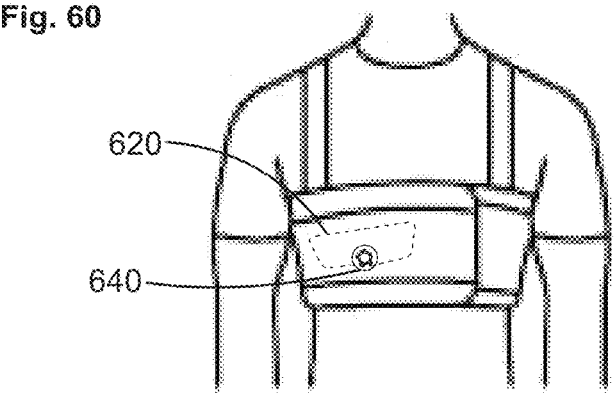
Figure 63:
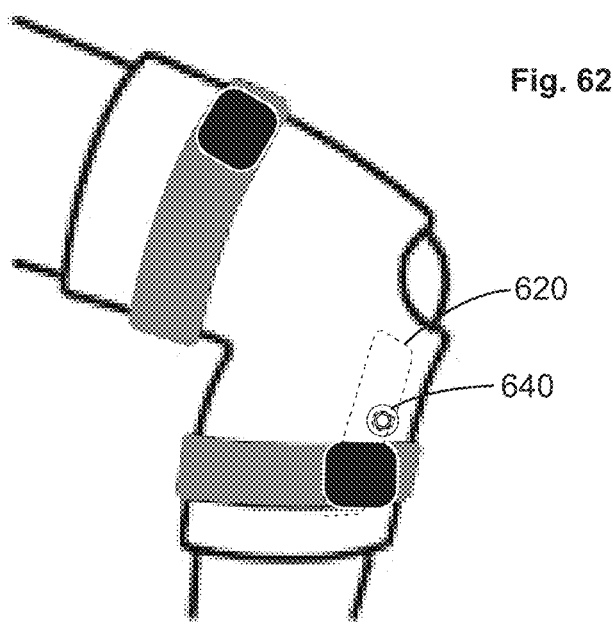
Figure 64:
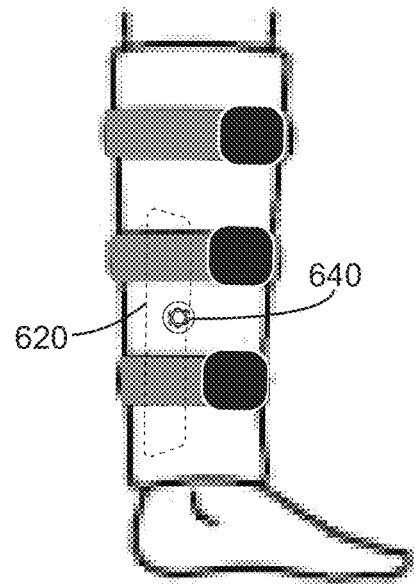

FIG. 60 shows fit systems 620 applied to a prosthesis 1000 where the tension lines are straps banded about the socket of prosthesis. FIGS. 61-64 show various uses of the fits systems 620 in the field of orthotics (braces) for bracing bones and joints. FIG. 61 shows a fit system 620 utilized in an ankle orthosis 1010. As shown in FIG. 61, one strap is banded about a leg portion of the brace and one strap is banded about a foot portion of the brace. The adjustment device 640 of the fit system 620 is mounted to the device and controls tension in the two straps. FIG. 62 shows a fit system 620 applied to a back brace 1020 for thoracic lumbar sacral orthosis (TLSO) application. The strap of the system 620 is banded about the back and torso of the user and the adjustment device 640 is positioned over a user's chest for access to the user. FIG. 63 shows fit systems 620 applied to a knee brace 1030 or knee orthosis. One fit system is banded about the leg above the knee, while another fit system is banded about the leg below the knee. The adjustment devices 640 of the fit systems 620 can adjust tension in the straps to fit the straps to the user's leg. FIG. 64 shows fit systems 620 applied to a post-operative knee brace 1040 or knee immobilizer. The fit systems 620 are shown banded about the user's lower leg.

Figure 65:
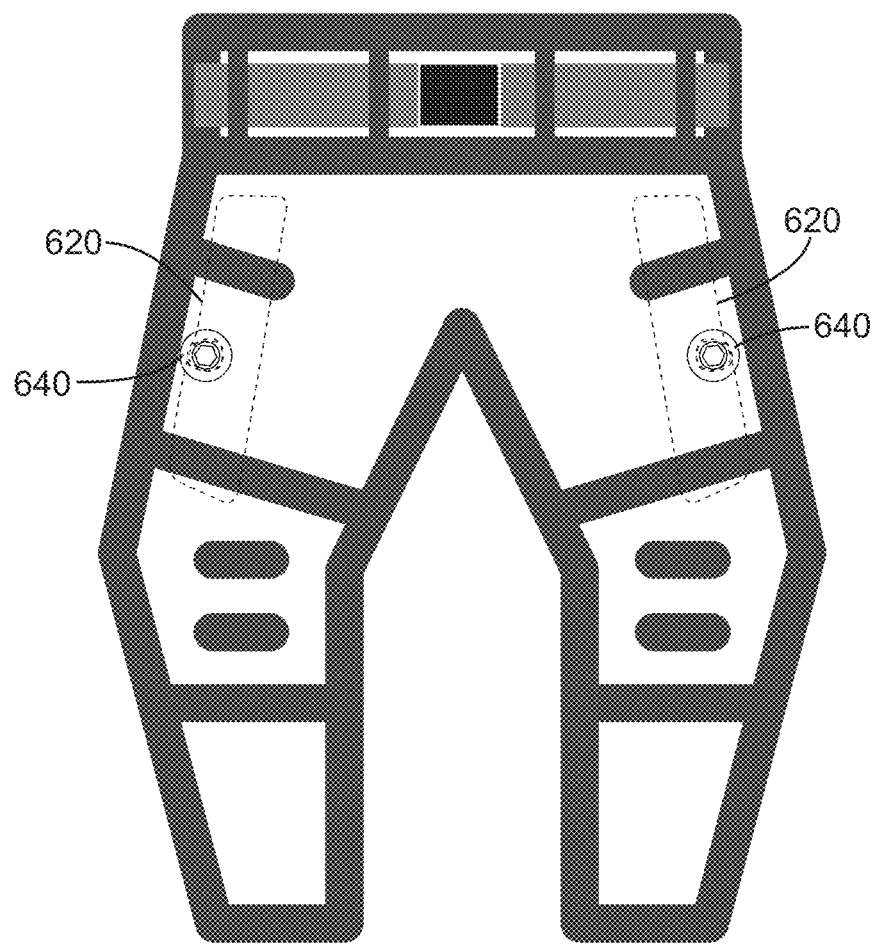
Figure 66:
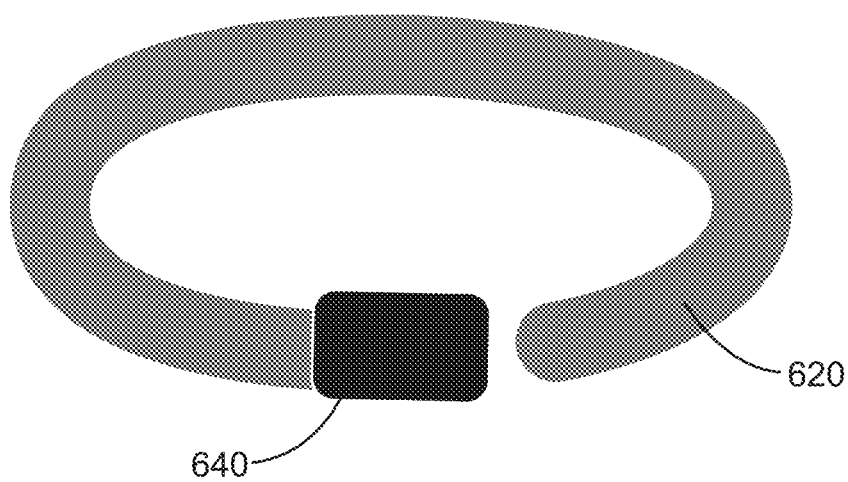

FIGS. 65 and 66 show fit systems 620 utilized in the field of clothing accessories and clothing. As shown in FIG. 65, the fit system 620 is used as a belt for a pair of pants, which may be integrated into the pants 1100. For example, the adjustment device 640 may be mounted to the pants with the strap of the fit system 620 banded about the waist of the pants. FIG. 66 shows the fit system 620 in the form of a belt 1110. Where the fit system 620 is worn about the body, it is preferred to incorporate a tension limiter. However, in certain applications where the fit system 620 is intended to apply tension around the body, such as a tourniquet, it will be appreciated that the tension device of the fit system 620 would omit a tension limiter.

There have been described and illustrated herein several embodiments of a tension device, fit systems using the tension device, and a method of using the tension devices and fit systems. While particular embodiments of the invention have been described, it is not intended that the invention be limited thereto, as it is intended that the invention be as broad in scope as the art will allow and that the specification be read likewise. Thus, with respect to any embodiment, where a hex-shaped control port or similar structure has been described and corresponding hex-shaped tool for insertion therein and operation on the adjustment device, it is appreciated and intended that the control port or similar structure and working end of the tool can be any cooperative shapes that permit application of a torque. Thus, by way of example only, they can both have cross-sectional shapes that are polygonal, both have interfering but different cross-sectional polygonal shapes, or even have shapes with a combination of curves and/or at flat, provided that both the port and tool are not completely circular. Further, while particular tension line types have been disclosed, it will be appreciated that other tension line types may be used as well. For all of the embodiments, the line tensioning systems may be made from a plastic, metal, or a combination plastic and metal components. In addition, while particular types of plastics have been disclosed for parts of the embodiments, it will be understood that other suitable types of plastics can be used. For example, and not by way of limitation, acrylic and polycarbonate may be used. Moreover, while particular configurations have been disclosed in reference to housings for the tension devices, it will be appreciated that other configurations could be used as well. It will therefore be appreciated by those skilled in the art that, yet other modifications could be made to the provided invention without deviating from its scope as claimed.

What is claimed is:

1. A tool-operated adjustment device for use with at least one tension line, the adjustment device comprising:
    a housing supporting a rotatable spool that is operably coupled to the at least one tension line, wherein the spool is configured to rotate about a first axis in a first rotational direction to wind the at least one tension line around the spool, and wherein the spool is further configured to rotate about the first axis in a second rotational direction opposite the first rotational direction to unwind the at least one tension line from the spool, the housing including a base having a lower surface extending in a plane and a cover coupled to the base and surrounding the spool;
    a first socket pivotally coupled to the housing and configured to rotate, and the first socket releasably coupled to the spool to drive rotation of the spool in the first rotational direction, wherein the first socket is configured to removably connect and disconnect to a first tool configured to rotate the first socket when connected to the first socket; and
    a release mechanism that is configured to selectively release the spool relative to the housing such that the spool is free to rotate relative to the housing in either the first rotational direction or the second rotational direction in response to manual forces applied to the release mechanism.

2. The adjustment device according to claim 1, wherein the release mechanism is configured to release the spool in response to a manual force applied in a direction parallel to the first axis.

3. The adjustment device according to claim 1, wherein the release mechanism is configured to release the spool in response to a force applied by the first tool in response to connection of the first tool to the first socket.

4. The adjustment device according to claim 1, wherein the first axis is perpendicular to the plane of the lower surface of the base.

5. The adjustment device according to claim 1, wherein the socket rotates about an axis parallel to the first axis.

6. The adjustment device according to claim 1, wherein the socket rotates coaxial with the first axis.

7. The adjustment device according to claim 1, further comprising:
a ratcheting adjustment mechanism supported by the housing,
wherein the ratcheting adjustment mechanism includes a first engagement member that is selectively coupled to the spool, wherein the first engagement member has a coupled configuration that permits the spool to rotate in the first rotational direction while preventing the spool from rotating in the second rotational direction, and wherein the first engagement member has a decoupled configuration that mechanically decouples the first engagement member from the spool.

8. The adjustment device according to claim 7, wherein the ratcheting adjustment mechanism further includes a second engagement member that is operably coupled between the first socket and the spool, wherein the second engagement member has a coupled configuration that mechanically couples the first socket to the spool such that pivoting motion of the first socket drives the spool in the first rotational direction and prevents the spool from rotating in the second rotational direction, and wherein the second engagement member has a decoupled configuration that mechanically decouples the first socket from the spool,
wherein the release mechanism is configured to selectively release the spool by simultaneously configuring the first and second engagement members into their respective decoupled configurations.

9. The adjustment device according to claim 8, wherein the first socket is configured to translate relative to the housing and the spool in a first longitudinal direction parallel to the first axis to configure the second engagement member into its decoupled configuration;
wherein the release mechanism includes a biasing member between the spool and the first socket that is configured to bias the first socket in a second longitudinal direction opposite the first longitudinal direction.

10. The adjustment device according to claim 1, wherein the release mechanism is configured for engagement with the first socket in a first configuration and is configured to be disengaged with the first socket in a second configuration, wherein in the first configuration the spool is prevented from rotating in either the first or second rotational directions and in the second configuration the spool is free to rotate in the first or second rotational directions.

11. The adjustment device according to claim 10, wherein the release mechanism includes a retainer configured for extension into the first socket in the first configuration and configured for displacement out of the first socket in the second configuration.

12. The adjustment device according to claim 11, wherein the retainer is configured to be displaced out of the socket in response to insertion of the first tool into the first socket and is configured to extend into the socket in response to withdrawal of the first tool from the first socket.

13. The adjustment device according to claim 7, wherein the first engagement member is pivotally coupled to the housing and configured to rotate about an axis displaced from the first axis and the rotation of the first socket.

14. The adjustment device according to claim 13, wherein the first engagement member is pivotally coupled to a second socket separate and distinct from the first socket, wherein the second socket is configured to receive a tool to rotate the second socket and the first engagement member to configure the first engagement member into its decoupled configuration.

15. The adjustment device according to claim 1, wherein the spool has an axle having an oval profile.

16. The adjustment device according to claim 1, wherein the base has a mounting flange for mounting the adjustment device to a substrate and wherein the mounting flange is configured to be sewn to the substrate.

17. The adjustment device according to claim 1, further comprising:
a rotary dial rotationally fixed to the first tool socket and configured for rotation about the first axis, the rotary dial configured to be rotated manually without the first tool.

18. A system comprising:
an adjustment device according to claim 1; and
at least one flexible elongate tension line connected to the spool.

19. The system according to claim 18, wherein:
the tension line is a flat strap, a cable, or a lace.

20. A method of winding a tension line comprising:
providing a tool-operated adjustment device according to claim 1;
connecting the first tool to the first socket;
pivoting the first tool to drive the spool in the first rotational direction; and
disconnecting the first tool from the first socket.

21. The method according to claim 20, further comprising:
pivoting the first tool to drive the spool in the second rotational direction.

22. The method according to claim 20, further comprising:
applying manual forces to the release mechanism to release the spool to permit the spool to rotate in the second rotational direction.

* * * * *